US012649772B2

(12) United States Patent
Maynard et al.

(10) Patent No.: US 12,649,772 B2
(45) Date of Patent: Jun. 9, 2026

(54) HIGH AFFINITY ENGINEERED T-CELL RECEPTORS TARGETING CMV INFECTED CELLS

(71) Applicant: BOARD OF REGENTS, THE UNIVERSITY OF TEXAS SYSTEM, Austin, TX (US)

(72) Inventors: Jennifer A. Maynard, Austin, TX (US); Ellen Wagner, Larkspur, CO (US); Ahlam N. Qerqez, Cedar Park, TX (US); Annalee Nguyen, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1196 days.

(21) Appl. No.: 17/430,319

(22) PCT Filed: Feb. 12, 2020

(86) PCT No.: PCT/US2020/017940
§ 371 (c)(1),
(2) Date: Aug. 11, 2021

(87) PCT Pub. No.: WO2020/167957
PCT Pub. Date: Aug. 20, 2020

(65) Prior Publication Data
US 2022/0144916 A1     May 12, 2022

Related U.S. Application Data

(60) Provisional application No. 62/804,642, filed on Feb. 12, 2019.

(51) Int. Cl.
| | |
|---|---|
| A61K 40/32 | (2025.01) |
| A61K 38/17 | (2006.01) |
| A61K 40/11 | (2025.01) |
| A61K 40/46 | (2025.01) |
| A61K 45/06 | (2006.01) |
| A61K 47/64 | (2017.01) |
| C07K 14/705 | (2006.01) |
| C07K 16/28 | (2006.01) |
| G01N 33/569 | (2006.01) |
| A61K 38/00 | (2006.01) |

(52) U.S. Cl.
CPC ........ *C07K 14/7051* (2013.01); *A61K 38/177* (2013.01); *A61K 40/11* (2025.01); *A61K 40/32* (2025.01); *A61K 40/46* (2025.01); *A61K 45/06* (2013.01); *A61K 47/6425* (2017.08); *C07K 16/2809* (2013.01); *G01N 33/56983* (2013.01); *A61K 38/00* (2013.01); *C07K 2317/53* (2013.01); *C07K 2319/30* (2013.01); *G01N 2333/045* (2013.01)

(58) Field of Classification Search
CPC .............. A61K 39/4632; A61K 39/464; C07K 14/7051
See application file for complete search history.

(56) References Cited

U.S. PATENT DOCUMENTS

| | | | |
|---|---|---|---|
| 7,919,270 | B2 | 4/2011 | Kunaparaju et al. |
| 8,802,820 | B2 | 8/2014 | Chamberlain et al. |
| 2002/0136724 | A1 | 9/2002 | Mohler |
| 2002/0150891 | A1 | 10/2002 | Hood et al. |
| 2016/0297886 | A1 | 10/2016 | Georgiou et al. |
| 2017/0166622 | A1 | 6/2017 | Baeuerle et al. |
| 2018/0118852 | A1 | 5/2018 | Deshpande et al. |
| 2018/0208657 | A1 | 7/2018 | Jung et al. |

FOREIGN PATENT DOCUMENTS

| | | |
|---|---|---|
| WO | WO 2006/125962 | 11/2006 |
| WO | WO 2011/091078 | 7/2011 |
| WO | WO 2015/017548 | 2/2015 |

OTHER PUBLICATIONS

Cole et al., J. Biol. Chem., 2014, vol. 289(2):628-638.*
Aggen et al., Identification and engineering of human variable regions that allow expression of stable single-chain T cell receptors. *Protein Eng Des Sel* 24, 361-372, 2011.
Boulter et al., Stable, soluble T-cell receptor molecules for crystallization and therapeutics. *Protein Eng* 16(9): 707-711, 2003.
Cole et al., Increased Peptide Contacts Govern High Affinity Binding of a Modified TCR Whilst Maintaining a Native pMHC Docking Mode. *Front Immunol* 4, 168, 2013.
Gunnarsen et al., Chaperone-assisted thermostability engineering of a soluble T cell receptor using phage display. *Scientific reports* 3, 1162, 2013.
Kuball et al., "Increasing functional avidity of TCR-redirected T cells by removing defined N-glycosylation sites in the TCR constant domain," *Journal of Experimental Medicine*, 206(2):463-475, 2009.
Li et al., Directed evolution of human T-cell receptors with picomolar affinities by phage display. *Nat Biotechnol* 23, 349-354, 2005.
Maynard et al., High-level bacterial secretion of single-chain αβ T-cell receptors. *Journal of Immunological Methods* 306, 51-67, 2005.

(Continued)

*Primary Examiner* — Xiaozhen Xie
(74) *Attorney, Agent, or Firm* — pH IP Law

(57) ABSTRACT

Provided herein are engineered T-celi receptors (TCRs) having nanomoiar affinity for the immuno-dominant pp65 peptide residing between residues 495-503 (NLV) in complex with HLA-A2*02:01. The TCRs may be membrane-hound TCRs, soluble TCRs, chimeric TCRs, or chimeric antigen receptors. Also provided are methods of using the engineered TCRs to treat diseases, monitor disease progression, monitor vaccine efficacy, and detecting NLV/A2 presentation on the surface of cells.

20 Claims, 28 Drawing Sheets
(23 of 28 Drawing Sheet(s) Filed in Color)
Specification includes a Sequence Listing.

(56) References Cited

OTHER PUBLICATIONS

PCT International Search Report and Written Opinion issued in International Application No. PCT/US2020/017940, dated May 27, 2020.

Saulquin et al., A global appraisal of immunodominant CD8 T cell responses to Epstein-Barr virus and cytomegalovirus by bulk screening. *Eur J Immunol* 30, 2531-2539,2000.

Sprague et al., The human Cytomegalovirus Fc Receptor gp68 Binds the Fc CH2-CH3 Interface of Immunoglobulin G, *Journal of Virology*, 82(7):3490-3499, 2008.

Trautmann et al., Selection of T cell clones expressing high-affinity public TCRs within Human cytomegalovirus-specific CD8 T cell responses. *J Immunol* 175, 6123-6132, 2005.

Wagner et al., "Human cytomegalovirus-specific T-cell receptor engineered for high affinity and soluble expression using mammalian cell display," *Journal of Biological Chemistry*, 294(15):5790-5804, 2019.

Wang et al., T cell receptor αβ diversity inversely correlates with pathogen-specific antibody levels in human cytomegalovirus infection. *Sci Transl Med* 4, 128ra142, 2012.

Wills et al., The human cytotoxic T-lymphocyte (CTL) response to cytomegalovirus is dominated by structural protein pp65: frequency, specificity, and T-cell receptor usage of pp65-specific CTL. *J Virol* 70, 7569-7579.,1996.

Yang et al., Elimination of Latently HIV-infected Cells from Antiretroviral Therapy-suppressed Subjects by Engineered Immune-mobilizing T-cell Receptors. *Mol Ther* 24, 1913-1925, 2016.

* cited by examiner

CDR3α C A R N T G N Q

CDR3β A S S P V T G G I Y G Y T

FIG. 14A-C

| | CDRα1 | | | | | CDRα3 | | | | | | |
|---|---|---|---|---|---|---|---|---|---|---|---|---|
| IMGT # | 28 | 29 | 36 | 37 | 38 | 104 | 105 | 106 | 107 | 108 | 109 | 114 | 115 |
| WT | S | N | F | Y | A | C | A | R | N | T | G | N | Q |
| a2b8 | * | * | * | * | * | * | * | * | * | Y | * | * | H |
| R2G | L | D | * | W | * | * | * | * | * | Y | * | * | H |
| 2S-16 | * | * | * | W | * | * | * | * | * | Y | * | * | * |
| 2S-20 | * | * | * | W | * | * | * | * | * | Y | * | * | P |

| | | | CDRβ3 | | | | | | | | | |
|---|---|---|---|---|---|---|---|---|---|---|---|---|
| IMGT # | 105 | 106 | 107 | 108 | 109 | 110 | 111 | 112 | 113 | 114 | 115 | 116 | 117 |
| WT | A | S | S | P | V | T | G | G | I | Y | G | Y | T |
| a2b8 | * | * | * | L | * | * | * | * | V | * | L | * | * |
| R2G | * | * | * | L | * | * | * | * | V | * | L | * | * |
| 2S-16 | * | * | * | L | * | * | * | S | V | * | L | * | * |
| 2S-20 | * | * | * | W | * | * | * | * | V | * | * | * | * |

FIG. 16B

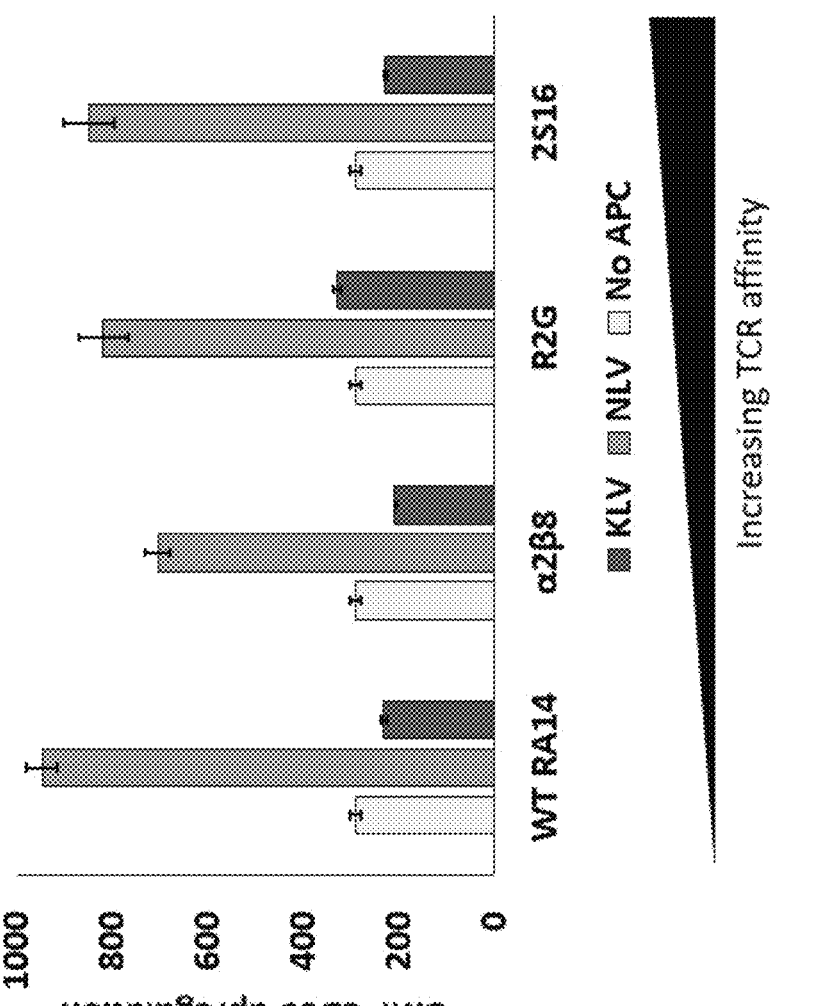
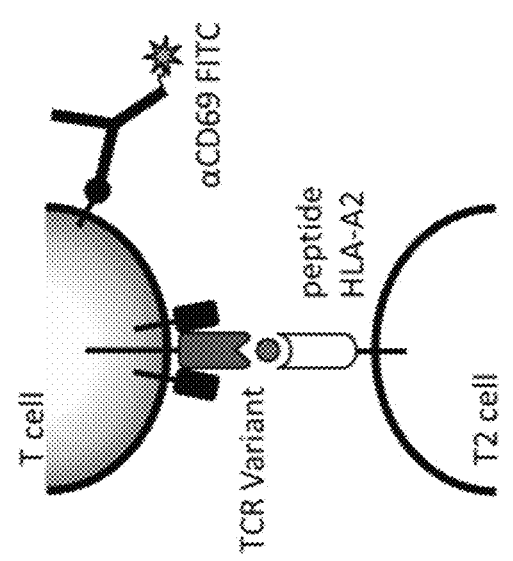
FIG. 19

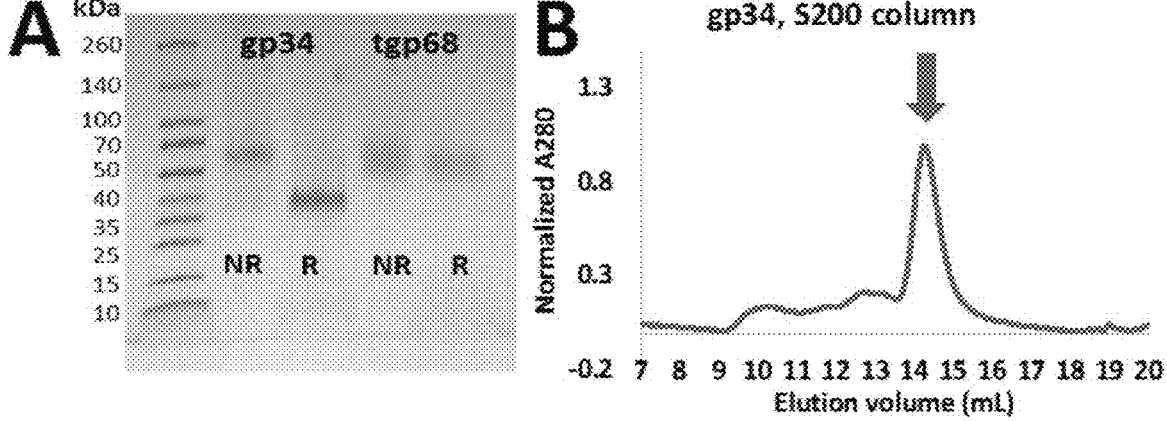
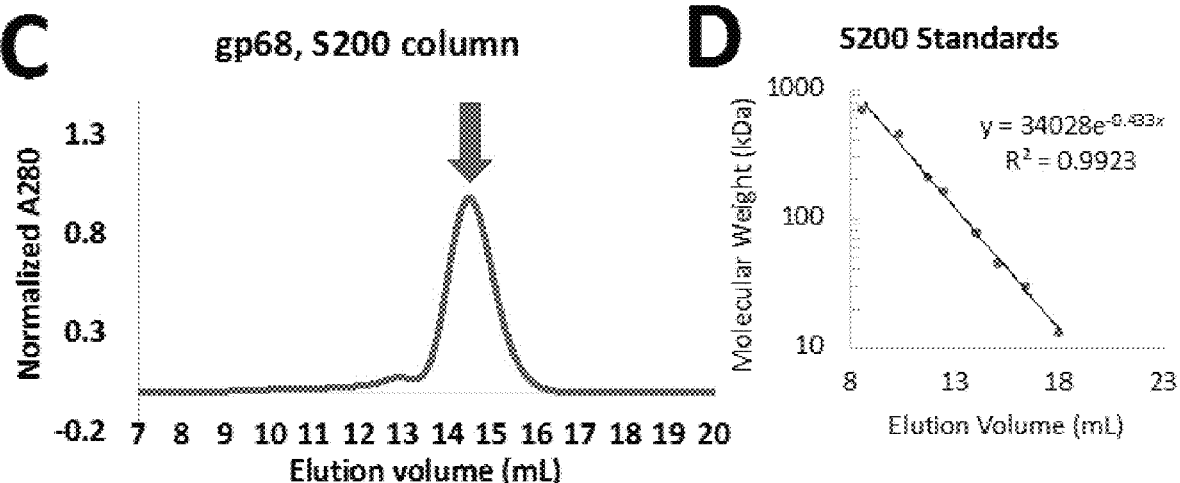
FIG. 20A-D

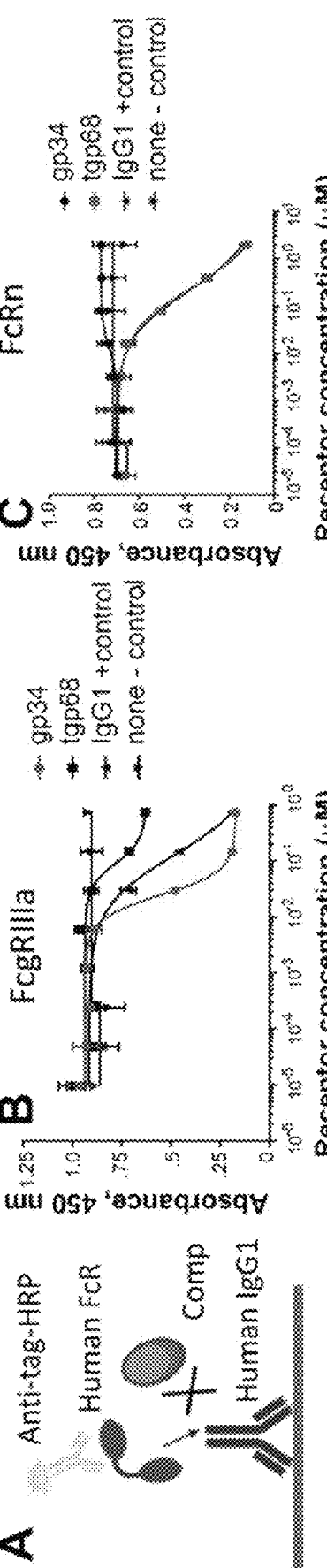
FIG. 21A-C

A.    WT Human IgG1: sequence alignment from residue 220 to 353 (no changes outside this region)

```
WTIgG1   CDKTHTCPPCPAPELLGGPSVFLFPPKPKDTLMISRTPEVTCVVVDVSHEDPEVKFNWYVDGV
3S-4     CDKTHTCPPCPAPELLGGPSVFLFPPKPKDTLMISRTPEVTCVVVDVSHEDPEVKFNWYVDGV
3S-7     CDKTHTCPPCPAPELLGGPSVFLFPPKPKDTLMISRTPEVTCVVVDVSHEDPEVKFNWYVDGV
3S-12    CDKTHTCPPCPAPELLGGPSVFLFPPKPKDTLMISRTPEVTCVVVDVSHEDPEVKFNWYVDGV
3S-13    CDKTHTCPPCPAPELLGGPSVFLFPPKPKDTLMISRTPEVTCVVVDVSHEDPEVKFNWYVDGV
3S-14    CDKTHTCPPCPAPELLGGPSVFLFPPKPKDTLMISRTPEVTCVVVDVSHEDPEVKFNWYVDGV
4-3      CDKTHTCPPCPAPELLGGPSVFLFPPKPKDTLMISRTPEVTCVVVDVSLEDPEVKFNWYVDGV
4-7      CDKTHTCPPCPAPELLGGPSVFLFPPKPKDTLMISRTPEVTCVVVDVSLEDPEVKFNWYVDGV
YTE      CDKTHTCPPCPAPELLGGPSVFLFPPKPKDTLMISRTPEVTCVVVDVSHEDPEVKFNWYVDGV

WTIgG1   EVHNAKTKPREEQYNSTYRVVSVLTVLHQDWLNGKEYKCKVSNKALPAPIEKTISKAKGQPREPQVYTLPP (SEQ ID NO: 53)
3S-4     EVHNAKTKPREEQYNSTYRVVSVLTVLHQDWLNGKEYKCKVSNKALPAPIEKTIFKAKGQPREPQVYTLPP (SEQ ID NO: 54)
3S-7     EVHNAKTKPREEQYNSTYRVVSVLTVLHQDWLNGKEYKCKVSNKALPAPIEKTIFKAEGQPREPQVYTLPP (SEQ ID NO: 55)
3S-12    EVHNAKTKPREEQYNSTYRVVSVLTVLHQDWLNGKEYKCKVSNKALPAPIEKTIFKAKGQPREPQVILPP  (SEQ ID NO: 56)
3S-13    EVHNAKTKPREEQYNSTYRVVSVLTVLHQDWLNGKEYKCRVSNKALPAPIETISKAKGQPREPQVYTLPP  (SEQ ID NO: 57)
3S-14    EVHNAKTKPREEQYNSTYRVVSVLTVLHQDWLNGKEYKCKVSNKALPAPIEKTISIAKGQPREPQVYTLPP (SEQ ID NO: 58)
4-3      EVHNAKTKPREEQYNSTYRVVSVLTVLHQDWLNGKEYKCKVSNKALPAPIEETISKAKGQPREPQVYTLPP (SEQ ID NO: 59)
4-7      EVHNAKTKPREKQYNSTYRVVSVLTVLHLDWLNGKEYKCKVSNKALPAPIEETISKAKGQPREPQVYTLPP (SEQ ID NO: 69)
YTE      EVHNAKTKPREEQYNSTYRVVSVLTVLHQDWLNGKEYKCKVSNKALPAPIEKTISKAKGQPREPQVYTLPP (SEQ ID NO: 70)
```

B.

gp34 escape variants:

3S-4: S337F 3S-7: S337F, G341E 3S-12: S337F, E345K, T350I 3S-13: K334E, K338I 3S-14: S337F, T350I 4-3: H268L, K334E 4-7: H268L, E294K, Q313L, K334E gp68 escape variants

YTE: M252Y, S254T, T256E

FIG. 23A-B

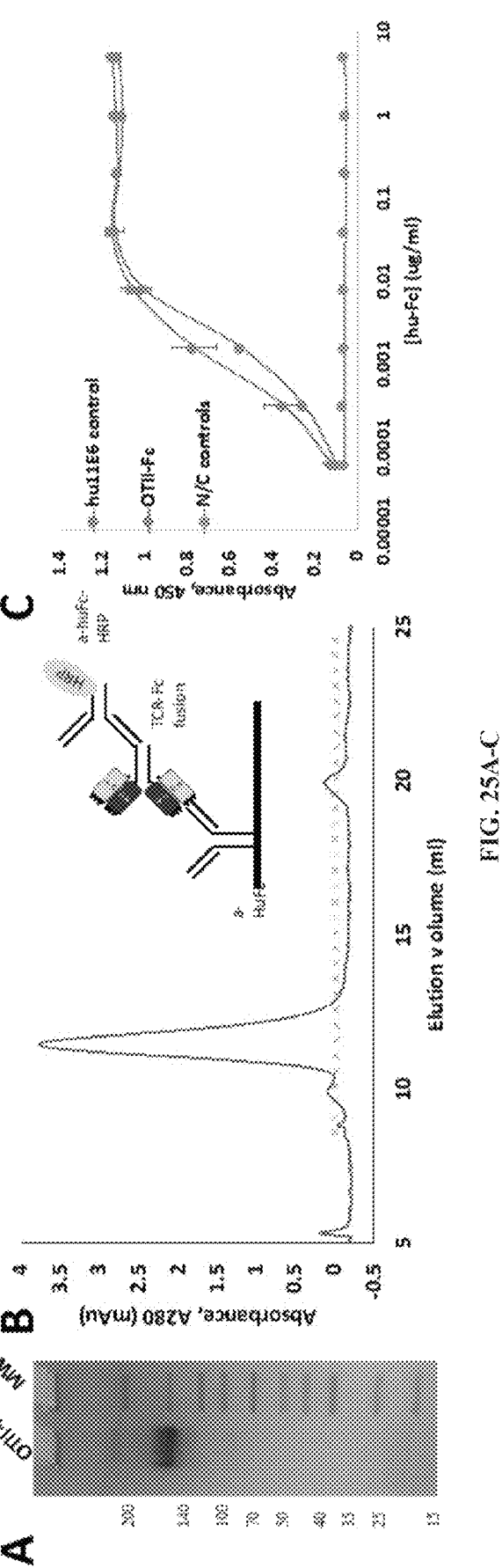
FIG. 25A-C

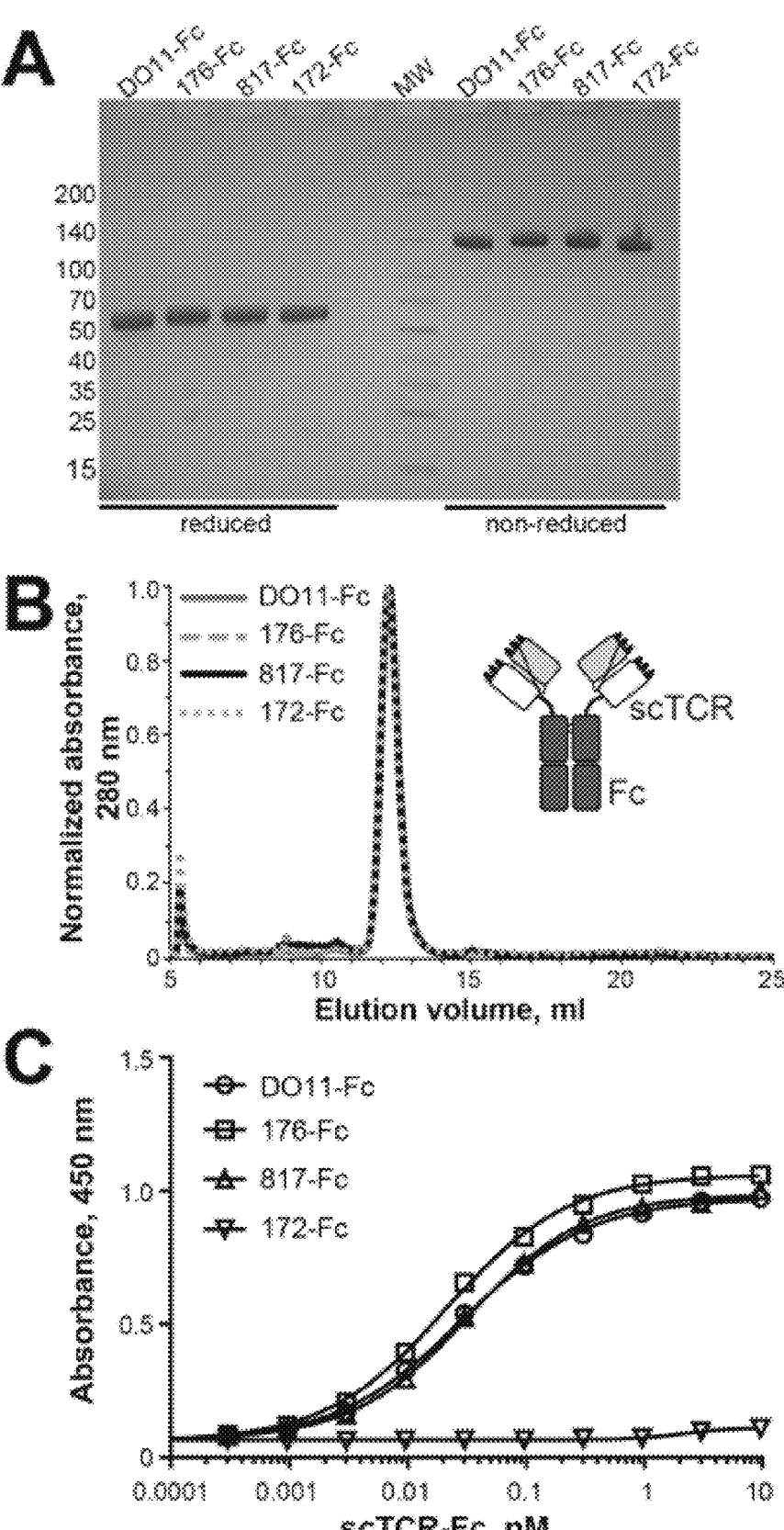
FIG. 26A-C

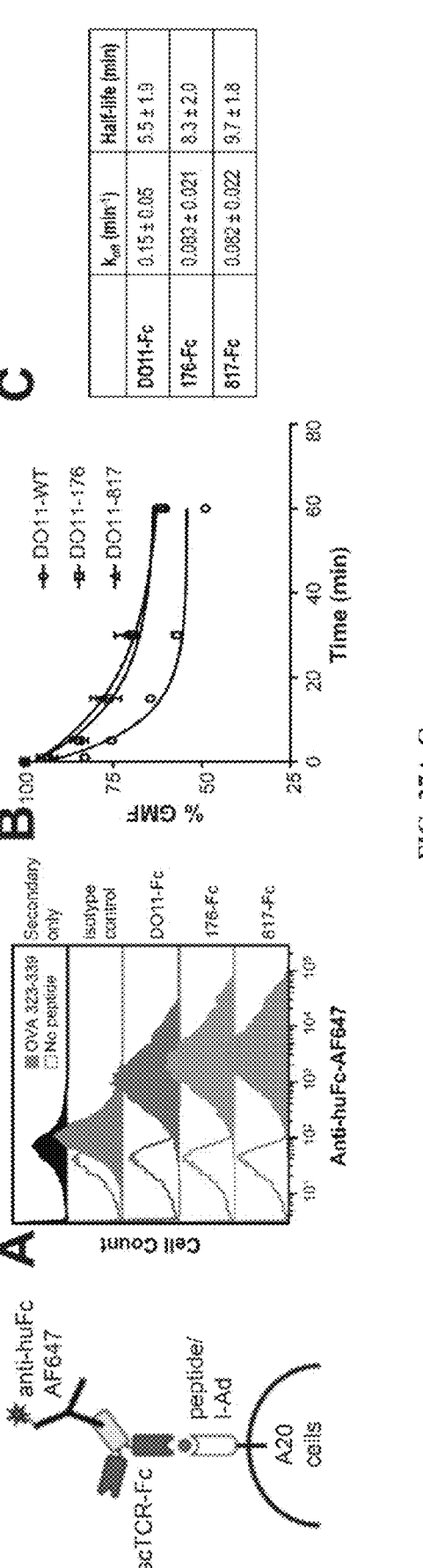
FIG. 27A–C

SEQUENCE LISTING

<160> NUMBER OF SEQ ID NOS: 76

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Cys Ala Arg Asn Ser Gly Asn Pro
1               5

<210> SEQ ID NO 2
<211> LENGTH: 8

```
<212> TYPE: PRT
<213> ORGANISM: Artificial sequence
<220> FEATURE:
<223> OTHER INFORMATION: Synthetic peptide

<400> SEQUENCE: 2

Cys Ala Arg Asn Tyr Gly Asn His
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Cys Ala Arg Asn Tyr Ile Asn Thr
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Cys Ala Arg Ser Phe Gly Asn Pro
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic peptide

<400> SEQUENCE: 5

Cys Ala Arg Ser Val Gly Asn Ser
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Cys Ala Arg Leu Leu Ala Asn Leu
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic peptide

<400> SEQUENCE: 7

Cys Ala Arg Gly Ser Trp Asn Gln
1               5

<210> SEQ ID NO 8
<211> LENGTH: 13
<212> TYPE: PRT
```

```
<213> ORGANISM: Artificial sequence
<220> FEATURE:
<223> OTHER INFORMATION: Synthetic peptide

<400> SEQUENCE: 8

Ala Ala Ala Pro Val Thr Gly Gly Val Tyr Leu Tyr Thr
1               5                   10

<210> SEQ ID NO 9
<211> LENGTH: 13
<212> TYPE: PRT
<213> ORGANISM: Artificial sequence
<220> FEATURE:
<223> OTHER INFORMATION: Synthetic peptide

<400> SEQUENCE: 9

Ala Ser Ser Arg Val Thr Gly Gly Val Tyr Leu Tyr Thr
1               5                   10

<210> SEQ ID NO 10
<211> LENGTH: 13
<212> TYPE: PRT
<213> ORGANISM: Artificial sequence
<220> FEATURE:
<223> OTHER INFORMATION: Synthetic peptide

<400> SEQUENCE: 10

Ala Ser Ser Pro Ile Thr Gly Ser Thr Tyr Ile Tyr Thr
1               5                   10

<210> SEQ ID NO 11
<211> LENGTH: 13
<212> TYPE: PRT
<213> ORGANISM: Artificial sequence
<220> FEATURE:
<223> OTHER INFORMATION: Synthetic peptide

<400> SEQUENCE: 11

Ala Ser Ser Pro Ile Thr Gly Ala Pro Tyr Leu Tyr Thr
1               5                   10

<210> SEQ ID NO 12
<211> LENGTH: 13
<212> TYPE: PRT
<213> ORGANISM: Artificial sequence
<220> FEATURE:
<223> OTHER INFORMATION: Synthetic peptide

<400> SEQUENCE: 12

Ala Ser Ser Pro Val Thr Gly Ser Ser Tyr Gly Tyr Thr
1               5                   10

<210> SEQ ID NO 13
<211> LENGTH: 13
<212> TYPE: PRT
<213> ORGANISM: Artificial sequence
<220> FEATURE:
<223> OTHER INFORMATION: Synthetic peptide

<400> SEQUENCE: 13

Ala Ser Ser Trp Ile Thr Gly Ser Ile Tyr Thr Tyr Thr
1               5                   10

<210> SEQ ID NO 14
<211> LENGTH: 13
<212> TYPE: PRT
<213> ORGANISM: Artificial sequence
```

-continued

```
<220> FEATURE:
<223> OTHER INFORMATION: Synthetic peptide

<400> SEQUENCE: 14

Ala Ser Ser Pro Val Thr Gly Ser Ser Tyr Trp Tyr Thr
1               5                   10

<210> SEQ ID NO 15
<211> LENGTH: 13
<212> TYPE: PRT
<213> ORGANISM: Artificial sequence
<220> FEATURE:
<223> OTHER INFORMATION: Synthetic peptide

<400> SEQUENCE: 15

Ala Ser Ser Leu Val Thr Gly Gly Val Tyr Leu Tyr Thr
1               5                   10

<210> SEQ ID NO 16
<211> LENGTH: 13
<212> TYPE: PRT
<213> ORGANISM: Artificial sequence
<220> FEATURE:
<223> OTHER INFORMATION: Synthetic peptide

<400> SEQUENCE: 16

Ala Ser Ser Leu Val Thr Gly Ile Pro Tyr Leu Tyr Thr
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic peptide

<400> SEQUENCE: 17

Ala Ser Ser Arg Val Thr Gly Ser Val Tyr Gly Tyr Thr
1               5                   10

<210> SEQ ID NO 18
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 18

Ile Leu Asn Val Glu Gln Ser Pro Gln Ser Leu His Val Gln Glu Gly
1               5                   10                  15

Asp Ser Thr Asn Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Arg Asn Thr Gly Asn
                85                  90                  95

Gln Phe Tyr Phe Gly Thr Gly Thr Ser Leu Thr Val Ile Pro
            100                 105                 110
```

<210> SEQ ID NO 19
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 19

```
Ile Leu Asn Val Glu Gln Ser Pro Gln Ser Leu His Val Gln Glu Gly
1               5                   10                  15

Asp Ser Thr Gln Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Arg Asn Ser Gly Asn
                85                  90                  95

Pro Phe Tyr Phe Gly Thr Gly Thr Ser Leu Thr Val Ile Pro
            100                 105                 110
```

<210> SEQ ID NO 20
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 20

```
Ile Leu Asn Val Glu Gln Ser Pro Gln Ser Leu His Val Gln Glu Gly
1               5                   10                  15

Asp Ser Thr Gln Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Arg Asn Tyr Gly Asn
                85                  90                  95

His Phe Tyr Phe Gly Thr Gly Thr Ser Leu Thr Val Ile Pro
            100                 105                 110
```

<210> SEQ ID NO 21
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 21

```
Ile Leu Asn Val Glu Gln Ser Pro Gln Ser Leu His Val Gln Glu Gly
1               5                   10                  15

Asp Ser Thr Gln Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45
```

-continued

```
Val Met Thr Leu Asn Gly Asp Glu Lys Lys Lys Gly Arg Ile Ser Ala
    50              55              60

Thr Leu Asn Thr Lys Glu Gly Tyr Ser Tyr Leu Tyr Ile Lys Gly Ser
65              70              75              80

Gln Pro Glu Asp Ser Ala Thr Tyr Leu Cys Ala Arg Asn Tyr Ile Asn
                85              90              95

Thr Phe Tyr Phe Gly Thr Gly Thr Ser Leu Thr Val Ile Pro
            100             105             110

<210> SEQ ID NO 22
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 22

Ile Leu Asn Val Glu Gln Ser Pro Gln Ser Leu His Val Gln Glu Gly
1               5               10              15

Asp Ser Thr Gln Phe Thr Cys Ser Phe Pro Ser Ser Asn Phe Tyr Ala
            20              25              30

Leu His Trp Tyr Arg Trp Glu Thr Ala Lys Ser Pro Glu Ala Leu Phe
        35              40              45

Val Met Thr Leu Asn Gly Asp Glu Lys Lys Lys Gly Arg Ile Ser Ala
    50              55              60

Thr Leu Asn Thr Lys Glu Gly Tyr Ser Tyr Leu Tyr Ile Lys Gly Ser
65              70              75              80

Gln Pro Glu Asp Ser Ala Thr Tyr Leu Cys Ala Arg Ser Phe Gly Asn
                85              90              95

Pro Phe Tyr Phe Gly Thr Gly Thr Ser Leu Thr Val Ile Pro
            100             105             110

<210> SEQ ID NO 23
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 23

Ile Leu Asn Val Glu Gln Ser Pro Gln Ser Leu His Val Gln Glu Gly
1               5               10              15

Asp Ser Thr Gln Phe Thr Cys Ser Phe Pro Ser Ser Asn Phe Tyr Ala
            20              25              30

Leu His Trp Tyr Arg Trp Glu Thr Ala Lys Ser Pro Glu Ala Leu Phe
        35              40              45

Val Met Thr Leu Asn Gly Asp Glu Lys Lys Lys Gly Arg Ile Ser Ala
    50              55              60

Thr Leu Asn Thr Lys Glu Gly Tyr Ser Tyr Leu Tyr Ile Lys Gly Ser
65              70              75              80

Gln Pro Glu Asp Ser Ala Thr Tyr Leu Cys Ala Arg Ser Val Gly Asn
                85              90              95

Ser Phe Tyr Phe Gly Thr Gly Thr Ser Leu Thr Val Ile Pro
            100             105             110

<210> SEQ ID NO 24
<211> LENGTH: 110
<212> TYPE: PRT
```

-continued

```
<213> ORGANISM: Artificial sequence
<220> FEATURE:
<223> OTHER INFORMATION: Synthetic polypeptide

<400> SEQUENCE: 24

Ile Leu Asn Val Glu Gln Ser Pro Gln Ser Leu His Val Gln Glu Gly
1               5                   10                  15

Asp Ser Thr Gln Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Arg Leu Leu Ala Asn
                85                  90                  95

Leu Phe Tyr Phe Gly Thr Gly Thr Ser Leu Thr Val Ile Pro
            100                 105                 110

<210> SEQ ID NO 25
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 25

Ile Leu Asn Val Glu Gln Ser Pro Gln Ser Leu His Val Gln Glu Gly
1               5                   10                  15

Asp Ser Thr Gln Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Arg Gly Ser Trp Asn
                85                  90                  95

Gln Phe Tyr Phe Gly Thr Gly Thr Ser Leu Thr Val Ile Pro
            100                 105                 110

<210> SEQ ID NO 26
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 26

Ile Leu Asn Val Glu Gln Ser Pro Gln Ser Leu His Val Gln Glu Gly
1               5                   10                  15

Asp Ser Thr Gln Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60
```

-continued

```
Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Arg Gly Ser Trp Asn
                85                  90                  95

Gln Phe Tyr Phe Gly Thr Gly Thr Ser Leu Thr Val Ile Pro
                100                 105                 110
```

```
<210> SEQ ID NO 27
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 27

Ala Gly Val Thr Gln Thr Pro Lys Phe Gln Val Leu Lys Thr Gly Gln
1                   5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Pro Val Thr
                85                  90                  95

Gly Gly Ile Tyr Gly Tyr Thr Phe Gly Ser Gly Thr Arg Leu Thr Val
                100                 105                 110

Val Glu
```

```
<210> SEQ ID NO 28
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 28

Ala Gly Val Thr Gln Thr Pro Lys Phe Gln Val Leu Lys Thr Gly Gln
1                   5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Gln
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Pro Val Thr
                85                  90                  95

Gly Gly Val Tyr Leu Tyr Thr Phe Gly Ser Gly Thr Arg Leu Thr Val
                100                 105                 110

Val Glu
```

```
<210> SEQ ID NO 29
<211> LENGTH: 114
```

-continued

```
<212> TYPE: PRT
<213> ORGANISM: Artificial sequence
<220> FEATURE:
<223> OTHER INFORMATION: Synthetic polypeptide

<400> SEQUENCE: 29

Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Gln
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Arg Val Thr
                85                  90                  95

Gly Gly Val Tyr Leu Tyr Thr Phe Gly Ser Gly Thr Arg Leu Thr Val
            100                 105                 110

Val Glu

<210> SEQ ID NO 30
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 30

Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Gln
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Pro Ile Thr
                85                  90                  95

Gly Ser Thr Tyr Ile Tyr Thr Phe Gly Ser Gly Thr Arg Leu Thr Val
            100                 105                 110

Val Glu

<210> SEQ ID NO 31
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 31

Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30
```

```
Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Gln
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Pro Ile Thr
                85                  90                  95

Gly Ala Pro Tyr Leu Tyr Thr Phe Gly Ser Gly Thr Arg Leu Thr Val
            100                 105                 110

Val Glu

<210> SEQ ID NO 32
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 32

Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Gln
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Pro Val Thr
                85                  90                  95

Gly Ser Ser Tyr Gly Tyr Thr Phe Gly Ser Gly Thr Arg Leu Thr Val
            100                 105                 110

Val Glu

<210> SEQ ID NO 33
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 33

Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Gln
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Trp Ile Thr
                85                  90                  95

Gly Ser Ile Tyr Thr Tyr Thr Phe Gly Ser Gly Thr Arg Leu Thr Val
```

-continued

```
              100                105                110

Val Glu

<210> SEQ ID NO 34
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 34

Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Gln
        50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Pro Val Thr
                85                  90                  95

Gly Ser Ser Tyr Trp Tyr Thr Phe Gly Ser Gly Thr Arg Leu Thr Val
            100                 105                 110

Val Glu

<210> SEQ ID NO 35
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 35

Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Gln
        50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Leu Val Thr
                85                  90                  95

Gly Gly Val Tyr Leu Tyr Thr Phe Gly Ser Gly Thr Arg Leu Thr Val
            100                 105                 110

Val Glu

<210> SEQ ID NO 36
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 36
```

-continued

```
Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
            35                  40                  45

Val Gly Ala Gly Ile Thr Asp Gln Gly Glu Val Pro Asn Gly Tyr Gln
        50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Leu Val Thr
                85                  90                  95

Gly Ile Pro Tyr Leu Tyr Thr Phe Gly Ser Gly Thr Arg Leu Thr Val
            100                 105                 110

Val Glu
```

<210> SEQ ID NO 37
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 37

```
Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
            35                  40                  45

Val Gly Ala Gly Ile Thr Asp Gln Gly Glu Val Pro Asn Gly Tyr Gln
        50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Arg Val Thr
                85                  90                  95

Gly Ser Val Tyr Gly Tyr Thr Phe Gly Ser Gly Thr Arg Leu Thr Val
            100                 105                 110

Val Glu
```

<210> SEQ ID NO 38
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 38

```
Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
            35                  40                  45

Val Gly Ala Gly Ile Thr Asp Gln Gly Glu Val Pro Asn Gly Tyr Gln
        50                  55                  60
```

-continued

```
Val Ser Arg Ser Thr Thr Glu Asp Phe Pro Leu Arg Leu Leu Ser Ala
65              70              75              80

Ala Pro Ser Gln Thr Ser Val Tyr Phe Cys Ala Ser Ser Leu Val Thr
                85              90              95

Gly Gly Val Tyr Leu Tyr Thr Phe Gly Ser Gly Thr Arg Leu Thr Val
            100             105             110

Val Glu

<210> SEQ ID NO 39
<211> LENGTH: 8
<212> TYPE: PRT
<213> ORGANISM: Artificial sequence
<220> FEATURE:
<223> OTHER INFORMATION: Synthetic peptide

<400> SEQUENCE: 39

Cys Ala Arg Asn Thr Gly Asn Gln
1               5

<210> SEQ ID NO 40
<211> LENGTH: 13
<212> TYPE: PRT
<213> ORGANISM: Artificial sequence
<220> FEATURE:
<223> OTHER INFORMATION: Synthetic peptide

<400> SEQUENCE: 40

Ala Ser Ser Pro Val Thr Gly Gly Ile Tyr Gly Tyr Thr
1               5               10

<210> SEQ ID NO 41
<211> LENGTH: 9
<212> TYPE: PRT
<213> ORGANISM: Artificial sequence
<220> FEATURE:
<223> OTHER INFORMATION: Synthetic peptide

<400> SEQUENCE: 41

Asn Leu Val Pro Met Val Ala Thr Val
1               5

<210> SEQ ID NO 42
<211> LENGTH: 10
<212> TYPE: PRT
<213> ORGANISM: Artificial sequence
<220> FEATURE:
<223> OTHER INFORMATION: Synthetic peptide

<400> SEQUENCE: 42

Lys Leu Val Ala Leu Gly Ile Asn Ala Val
1               5               10

<210> SEQ ID NO 43
<211> LENGTH: 25
<212> TYPE: PRT
<213> ORGANISM: Artificial sequence
<220> FEATURE:
<223> OTHER INFORMATION: Synthetic peptide

<400> SEQUENCE: 43

Arg Arg Lys Arg Gly Ser Gly Glu Gly Arg Gly Ser Leu Leu Thr Cys
1               5               10              15

Gly Asp Val Glu Glu Asn Pro Gly Pro
            20              25
```

```
<210> SEQ ID NO 44
<211> LENGTH: 15
<212> TYPE: PRT
<213> ORGANISM: Artificial sequence
<220> FEATURE:
<223> OTHER INFORMATION: Synthetic peptide

<400> SEQUENCE: 44

Asn Asn Ser Asn Asn Ser Asn Asn Ser Ala Ala Cys Asn Asn Ser
1               5                   10                  15

<210> SEQ ID NO 45
<211> LENGTH: 24
<212> TYPE: PRT
<213> ORGANISM: Artificial sequence
<220> FEATURE:
<223> OTHER INFORMATION: Synthetic peptide

<400> SEQUENCE: 45

Asn Asx Ser Val Asx Cys Ala Cys Cys Val Asx Cys Val Asx Cys Val
1               5                   10                  15

Asx Cys Thr Ala Cys Asn Asx Ser
            20

<210> SEQ ID NO 46
<211> LENGTH: 6
<212> TYPE: PRT
<213> ORGANISM: Homo sapiens

<400> SEQUENCE: 46

Val Glu Pro Lys Ser Cys
1               5

<210> SEQ ID NO 47
<211> LENGTH: 21
<212> TYPE: PRT
<213> ORGANISM: Artificial sequence
<220> FEATURE:
<223> OTHER INFORMATION: Synthetic peptide

<400> SEQUENCE: 47

Met Lys Thr Tyr Ala Pro Thr Leu Phe Met Phe Leu Trp Leu Gln Leu
1               5                   10                  15

Asp Gly Met Ser Gln
            20

<210> SEQ ID NO 48
<211> LENGTH: 18
<212> TYPE: PRT
<213> ORGANISM: Artificial sequence
<220> FEATURE:
<223> OTHER INFORMATION: Synthetic peptide

<400> SEQUENCE: 48

Met Gly Ser Arg Leu Phe Phe Val Leu Ser Ser Leu Leu Cys Ser Lys
1               5                   10                  15

His Met

<210> SEQ ID NO 49
<211> LENGTH: 8
<212> TYPE: PRT
<213> ORGANISM: Artificial sequence
<220> FEATURE:
<223> OTHER INFORMATION: Synthetic peptide
<220> FEATURE:
```

```
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 49

Cys Ala Arg Xaa Xaa Xaa Asn Xaa
1               5

<210> SEQ ID NO 50
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 50

Ala Ser Ser Xaa Xaa Thr Xaa Xaa Xaa Tyr Xaa Tyr Thr
1               5                   10

<210> SEQ ID NO 51
<211> LENGTH: 9
<212> TYPE: PRT
<213> ORGANISM: Artificial sequence
<220> FEATURE:
<223> OTHER INFORMATION: Synthetic peptide

<400> SEQUENCE: 51

Gly Ile Leu Gly Phe Val Phe Thr Leu
1               5

<210> SEQ ID NO 52
<211> LENGTH: 9
<212> TYPE: PRT
<213> ORGANISM: Artificial sequence
<220> FEATURE:
<223> OTHER INFORMATION: Synthetic peptide

<400> SEQUENCE: 52

Asn His Glu Tyr Ser Asn Phe Tyr Ala
1               5

<210> SEQ ID NO 53
<211> LENGTH: 134
<212> TYPE: PRT
<213> ORGANISM: Homo sapiens

<400> SEQUENCE: 53

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
```

-continued

```
             35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
                115                 120                 125

Val Tyr Thr Leu Pro Pro
    130

<210> SEQ ID NO 54
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 54

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
                100                 105                 110

Ile Glu Lys Thr Ile Phe Lys Ala Lys Gly Gln Pro Arg Glu Pro Gln
            115                 120                 125

Val Tyr Thr Leu Pro Pro
    130

<210> SEQ ID NO 55
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 55

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
    50                  55                  60
```

```
Val His Asn Ala Lys Thr Lys Pro Arg Glu Glu Gln Tyr Asn Ser Thr
65              70              75              80

Tyr Arg Val Val Ser Val Leu Thr Val Leu His Gln Asp Trp Leu Asn
            85              90              95

Gly Lys Glu Tyr Lys Cys Lys Val Ser Asn Lys Ala Leu Pro Ala Pro
            100             105             110

Ile Glu Lys Thr Ile Phe Lys Ala Lys Glu Gln Pro Arg Glu Pro Gln
        115             120             125

Val Tyr Thr Leu Pro Pro
    130

<210> SEQ ID NO 56
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 56

Cys Asp Lys Thr His Thr Cys Pro Pro Cys Pro Ala Pro Glu Leu Leu
1               5               10              15

Gly Gly Pro Ser Val Phe Leu Phe Pro Pro Lys Pro Lys Asp Thr Leu
            20              25              30

Met Ile Ser Arg Thr Pro Glu Val Thr Cys Val Val Val Asp Val Ser
            35              40              45

His Glu Asp Pro Glu Val Lys Phe Asn Trp Tyr Val Asp Gly Val Glu
    50              55              60

Val His Asn Ala Lys Thr Lys Pro Arg Glu Glu Gln Tyr Asn Ser Thr
65              70              75              80

Tyr Arg Val Val Ser Val Leu Thr Val Leu His Gln Asp Trp Leu Asn
            85              90              95

Gly Lys Glu Tyr Lys Cys Lys Val Ser Asn Lys Ala Leu Pro Ala Pro
            100             105             110

Ile Glu Lys Thr Ile Phe Lys Ala Lys Gly Gln Pro Arg Lys Pro Gln
        115             120             125

Val Tyr Ile Leu Pro Pro
    130

<210> SEQ ID NO 57
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 57

Cys Asp Lys Thr His Thr Cys Pro Pro Cys Pro Ala Pro Glu Leu Leu
1               5               10              15

Gly Gly Pro Ser Val Phe Leu Phe Pro Pro Lys Pro Lys Asp Thr Leu
            20              25              30

Met Ile Ser Arg Thr Pro Glu Val Thr Cys Val Val Val Asp Val Ser
            35              40              45

His Glu Asp Pro Glu Val Lys Phe Asn Trp Tyr Val Asp Gly Val Glu
    50              55              60

Val His Asn Ala Lys Thr Lys Pro Arg Glu Glu Gln Tyr Asn Ser Thr
65              70              75              80

Tyr Arg Val Val Ser Val Leu Thr Val Leu His Gln Asp Trp Leu Asn
            85              90              95
```

-continued

```
Gly Lys Glu Tyr Lys Cys Lys Val Ser Asn Lys Ala Leu Pro Ala Pro
            100                 105                 110

Ile Glu Glu Thr Ile Ser Ile Ala Lys Gly Gln Pro Arg Glu Pro Gln
        115                 120                 125

Val Tyr Thr Leu Pro Pro
    130

<210> SEQ ID NO 58
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 58

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Phe Lys Ala Lys Gly Gln Pro Arg Glu Pro Gln
        115                 120                 125

Val Tyr Ile Leu Pro Pro
    130

<210> SEQ ID NO 59
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 59

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Leu Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Glu Thr Ile Ser Lys Ala Lys Gly Gln Pro Arg Glu Pro Gln
```

```
            115               120               125
Val Tyr Thr Leu Pro Pro
    130

<210> SEQ ID NO 60
<211> LENGTH: 8
<212> TYPE: PRT
<213> ORGANISM: Artificial sequence
<220> FEATURE:
<223> OTHER INFORMATION: Synthetic peptide

<400> SEQUENCE: 60

Cys Ala Arg Asn Tyr Gly Asn Gln
1               5

<210> SEQ ID NO 61
<211> LENGTH: 8
<212> TYPE: PRT
<213> ORGANISM: Artificial sequence
<220> FEATURE:
<223> OTHER INFORMATION: Synthetic peptide

<400> SEQUENCE: 61

Cys Ala Arg Asn Tyr Gly Asn Pro
1               5

<210> SEQ ID NO 62
<211> LENGTH: 13
<212> TYPE: PRT
<213> ORGANISM: Artificial sequence
<220> FEATURE:
<223> OTHER INFORMATION: Synthetic peptide

<400> SEQUENCE: 62

Ala Ser Ser Leu Val Thr Gly Ser Val Tyr Leu Tyr Thr
1               5                   10

<210> SEQ ID NO 63
<211> LENGTH: 13
<212> TYPE: PRT
<213> ORGANISM: Artificial sequence
<220> FEATURE:
<223> OTHER INFORMATION: Synthetic peptide

<400> SEQUENCE: 63

Ala Ser Ser Trp Val Thr Gly Gly Val Tyr Leu Gly Thr
1               5                   10

<210> SEQ ID NO 64
<211> LENGTH: 5
<212> TYPE: PRT
<213> ORGANISM: Artificial sequence
<220> FEATURE:
<223> OTHER INFORMATION: Synthetic peptide

<400> SEQUENCE: 64

Ser Asn Phe Tyr Ala
1               5

<210> SEQ ID NO 65
<211> LENGTH: 5
<212> TYPE: PRT
<213> ORGANISM: Artificial sequence
<220> FEATURE:
<223> OTHER INFORMATION: Synthetic peptide

<400> SEQUENCE: 65
```

Leu Asp Phe Trp Ala
1               5

<210> SEQ ID NO 66
<211> LENGTH: 5
<212> TYPE: PRT
<213> ORGANISM: Artificial sequence
<220> FEATURE:
<223> OTHER INFORMATION: Synthetic peptide

<400> SEQUENCE: 66

Ser Asn Phe Trp Ala
1               5

<210> SEQ ID NO 67
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 67

Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
            35                  40                  45

Val Gly Ala Gly Ile Thr Asp Gln Gly Glu Val Pro Asn Gly Tyr Gln
        50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Leu Val Thr
                85                  90                  95

Gly Ser Val Tyr Leu Tyr Thr Phe Gly Ser Gly Thr Arg Leu Thr Val
            100                 105                 110

Val Glu

<210> SEQ ID NO 68
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 68

Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
            35                  40                  45

Val Gly Ala Gly Ile Thr Asp Gln Gly Glu Val Pro Asn Gly Tyr Gln
        50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Trp Val Thr
                85                  90                  95

Gly Gly Val Tyr Gly Tyr Thr Phe Gly Ser Gly Thr Arg Leu Thr Val

-continued

```
                 100             105             110

Val Glu

<210> SEQ ID NO 69
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 69

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Leu Glu Asp Pro Glu Val Lys Phe Asn Trp Tyr Val Asp Gly Val Glu
    50                  55                  60

Val His Asn Ala Lys Thr Lys Pro Arg Glu Lys Gln Tyr Asn Ser Thr
65                  70                  75                  80

Tyr Arg Val Val Ser Val Leu Thr Val Leu His Leu Asp Trp Leu Asn
                85                  90                  95

Gly Lys Glu Tyr Lys Cys Lys Val Ser Asn Lys Ala Leu Pro Ala Pro
            100                 105                 110

Ile Glu Glu Thr Ile Ser Lys Ala Lys Gly Gln Pro Arg Glu Pro Gln
        115                 120                 125

Val Tyr Thr Leu Pro Pro
    130

<210> SEQ ID NO 70
<211> LENGTH: 63
<212> TYPE: PRT
<213> ORGANISM: Artificial sequence
<220> FEATURE:
<223> OTHER INFORMATION: Synthetic polypeptide

<400> SEQUENCE: 70

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Tyr Ile Thr Arg Glu Pro Glu Val Thr Cys Val Val Val Asp Val Ser
        35                  40                  45

His Glu Asp Pro Glu Val Lys Phe Asn Trp Tyr Val Asp Gly Val
    50                  55                  60

<210> SEQ ID NO 71
<211> LENGTH: 4
<212> TYPE: PRT
<213> ORGANISM: Artificial sequence
<220> FEATURE:
<223> OTHER INFORMATION: Synthetic peptide

<400> SEQUENCE: 71

Arg Arg Lys Arg
1

<210> SEQ ID NO 72
<211> LENGTH: 4
```

```
<212> TYPE: PRT
<213> ORGANISM: Artificial sequence
<220> FEATURE:
<223> OTHER INFORMATION: Synthetic peptide

<400> SEQUENCE: 72

Ser Gly Ser Gly
1

<210> SEQ ID NO 73
<211> LENGTH: 6
<212> TYPE: PRT
<213> ORGANISM: Artificial sequence
<220> FEATURE:
<223> OTHER INFORMATION: Synthetic peptide

<400> SEQUENCE: 73

Ile Thr Gly Asn Gln Phe
1               5

<210> SEQ ID NO 74
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 74

Ile Leu Asn Val Glu Gln Ser Pro Gln Ser Leu His Val Gln Glu Gly
1               5                   10                  15

Asp Ser Thr Gln Phe Thr Cys Ser Phe Pro Ser Leu Asp Phe Trp Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Arg Asn Tyr Gly Asn
                85                  90                  95

His Phe Tyr Phe Gly Thr Gly Thr Ser Leu Thr Val Ile Pro
            100                 105                 110

<210> SEQ ID NO 75
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 75

Ile Leu Asn Val Glu Gln Ser Pro Gln Ser Leu His Val Gln Glu Gly
1               5                   10                  15

Asp Ser Thr Gln Phe Thr Cys Ser Phe Pro Ser Ser Asn Phe Trp Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80
```

-continued

```
Gln Pro Glu Asp Ser Ala Thr Tyr Leu Cys Ala Arg Asn Tyr Gly Asn
            85                  90                  95

Gln Phe Tyr Phe Gly Thr Gly Thr Ser Leu Thr Val Ile Pro
            100                 105                 110

<210> SEQ ID NO 76
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 76

Ile Leu Asn Val Glu Gln Ser Pro Gln Ser Leu His Val Gln Glu Gly
1               5                   10                  15

Asp Ser Thr Gln Phe Thr Cys Ser Phe Pro Ser Ser Asn Phe Trp Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Arg Asn Tyr Gly Asn
            85                  90                  95

Pro Phe Tyr Phe Gly Thr Gly Thr Ser Leu Thr Val Ile Pro
            100                 105                 110
```

1

HIGH AFFINITY ENGINEERED T-CELL RECEPTORS TARGETING CMV INFECTED CELLS

This application is a national phase application under 35 U.S.C. § 371 of International Application No. PCT/US2020/017940, filed Feb. 12, 2020, which claims the priority benefit of U.S. provisional Application No. 62/804,642, filed Feb. 12, 2019, the entirety of each of which is hereby incorporated by reference.

This invention was made with government support under Grant No. F32 GM111018 awarded by the National Institutes of Health and Grant No. DGE1610403 awarded by the National Science Foundation. The government has certain rights in the invention.

INCORPORATION OF SEQUENCE LISTING

This application contains a Sequence Listing .txt file, which has been submitted electronically and is hereby incorporated by reference in its entirety. Said .txt Sequence Listing, created on Jul. 1, 2025, is named UTSBP1216US_ST25.txt and is 47,970 bytes in size.

BACKGROUND OF THE INVENTION

1. Field of the Invention

The present invention relates generally to the field of medicine. More particularly, it concerns high affinity engineered T-cell receptors for detecting and targeting CMV infected cells.

2. Description of Related Art

Antibodies represent a large and growing class of successful therapeutics, by virtue of their abilities to tightly bind antigens that are secreted or expressed on a target cell surface. The structurally analogous T-cell receptor (TCR) provides access to a much wider array of intracellular and extracellular antigens that are presented on a cell surface as proteolyzed peptides in complex with major histocompatibility complex (MHC). Like antibodies, TCR binding sites are formed by six complementarity determining regions (CDRs), three on the alpha variable domain and three on the beta variable domain with the CDR3 loops dominating TCR-peptide interactions (Rossjohn et al., 2015). When a peptide-MHC complex is recognized by the TCR expressed on a T cell, TCR activation, cytokine release, and cell killing can follow.

There is considerable interest in using TCRs as therapeutics and reagents to monitor the presence of disease-related peptides. Engineered TCRs can be used in adoptive T-cell therapies to re-direct patient T cells to recognize a chosen target (Harris and Kranz, 2016), while soluble TCRs can be used as antibody-like reagents to bind specific peptide MHC complexes presented on a cell surface (Oates et al., 2015). Proof-of-concept for these approaches has been demonstrated with TCRs targeting the immunodominant Gag epitope SL9 from HIV. When transduced into patient T cells, high affinity TCRs were able to control viral replication (Varela-Rohena et al., 2008). When expressed as a soluble TCR linked to a CD3-specific single-chain antibody, the chimeric protein was able to redirect polyclonal CD8 T cells to kill CD4 T cells harboring reactivated HIV (Yang et al., 2016).

Viral infection by cytomegalovirus (CMV) is also controlled by cytotoxic T cells in healthy individuals but causes disease in the very young, very old, and immunocompromised, with no vaccine candidate nearing licensure (Plotkin and Boppana, 2018). CMV-specific cytotoxic T cells primarily target peptides from the pp65 tegument protein, with the immuno-dominant peptide residing between residues 495-503 (sequence NLVPMVATV (SEQ ID NO: 41), hereafter called NLV) (Wills et al., 1996; Saulquin et al., 2000) in complex with HLA-A2*02:01 (hereafter called A2), the most common allele in North America. Adoptive transfer of NLV-specific T cells is sufficient to control infection in allogeneic hematopoietic stem cell transplantation patients with CMV infection (Feuchtinger et al., 2010). Notably, NLV is presented on the infected cell surface early after infection, prior to de novo protein synthesis and in the presence of therapeutics blocking viral replication (Riddell et al., 1991).

Identification of a validated, CMV-specific peptide-MHC complex suggests opportunities to monitor NLV-presenting cells, if an appropriate peptide-specific TCR is available. While hundreds of TCRs can recognize an immunodominant peptide, the NLV/A2 response is dominated by "public" clones whose CDR3α and/or CDR3β sequences are shared among unrelated individuals (Trautmann et al., 2005; Wang et al., 2012). One of these, RA14, emerged as the dominant clone after rounds of immunosuppression and viral reactivation in a rheumatoid arthritis patient with asymptomatic CMV infection (Trautmann et al., 2005). The RA14 CDR3α contains the two most common public features observed in NLV-reactive TCRs: CDR3α sequence $x_nGNQF$ (where $x_n$ indicates a variable number of residues), observed in 14% of all sequences across multiple donors and CDR3Ο sequence SxnTGxnYGY, observed in 13% of all sequences (Wang et al., 2012). The RA14 TCR has been crystallized in complex with its ligand NLV/A2, revealing a typical TCR-pMHC binding interface characterized by high structural complementarity for the entire peptide(Trautmann et al., 2009).

While RA14 appears to be an excellent candidate to monitor NLV/A2 presence and may be suitable for adoptive therapy applications, there are several limitations to using TCRs as soluble, antibody-like reagents. First, TCR-ligand binding affinities are much weaker than antibodies: RA14 has been reported to have a 6-30 μM equilibrium affinity for NLV/A2 (Gras et al., 2009; Gakamsky et al., 2007), whereas antibody-ligand affinities are typically >1000-fold stronger (1-10 nM $K_d$). Second, despite considerable effort, soluble expression of TCRs continues to present challenges, with no generally successful strategies identified.

To address these shortcomings, TCRs have been engineered for increased stability, expression level, and affinity. This has been achieved using a single-chain format and yeast display (Shusta et al., 1999; Holler et al., 2000; Shusta et al., 2000), but engineering of each unique TCR appears required to enable incorporation of properly folded protein into these formats (Aggen et al., 2011). Phage display of the TCR extracellular regions with a stabilizing di-sulfide bond in between the constant domains (Boulter et al., 2003) has also been used to identify several very high affinity human TCR variants (Varela-Rohena et al., 2008; Li et al., 2005; Liddy et al., 2012). While successful, phage display lacks the eukaryotic protein folding machinery, which is likely required to allow expression of a greater range of TCRs and is not compatible with efficient FACS-based selection strategies. To produce soluble protein, single-chain or extracellular two-chain TCRs are most commonly refolded from bacterial inclusion bodies with varying levels of success (Aggen et al., 2011). Some TCR sequences are amenable to soluble expression in bacteria with chaperone co-expression (Wulfing and Pluckthun, 1994; Maynard et al., 2005; Gunnarsen et al., 2013), in yeast (Shusta et al., 1999), or in mammalian cells (Mosquera et al., 2005; Walseng et al., 2015; Foss et al., 2016) but these represent only a fraction of TCRs of interest. Taken together, considerable effort is required to convert a TCR into a recombinant protein that can be used in biochemical assays or therapeutic methods.

SUMMARY OF THE INVENTION

In a first embodiment, there is provided an engineered T-cell receptor (TCR) comprising an alpha chain CDR3 having the amino acid sequence of any one of SEQ ID NOs: 1-7 and/or a beta chain CDR3 having the amino acid sequence of any one of SEQ ID NOs: 8-17. In some aspects, the engineered TCR is HLA-A2 restricted. In further aspects, the engineered TCR is HLA-A2*02:01 restricted. In other aspects, the engineered TCR specifically recognizes a peptide comprising an amino acid sequence of NLVPM-VATV (SEQ ID NO: 41) in complex with HLA-A2*02:01. In certain aspects, the engineered TCR comprises an alpha chain CDR3 having the amino acid sequence of SEQ ID NO: 2 and a beta chain CDR3 having the amino acid sequence of SEQ ID NO: 15. In several aspects, the engineered TCR comprises an alpha chain variable region having at least 90%, 91%, 92%, 93%, 94%, 95%, 96%, 97%, 98%, or 99% identity to the amino acid sequence of any one of SEQ ID NOs: 18-24 and/or a beta chain variable region having at least 90% identity to the amino acid sequence of any one of SEQ ID NOs: 25-34.

In still further aspects, the engineered TCR comprises an alpha chain of any one of SEQ ID NOs: 18-24 and/or a beta chain of any one of SEQ ID NOs: 25-34. In specific aspects, the engineered TCR comprises an alpha chain of SEQ ID NO: 19 and a beta chain of SEQ ID NO: 32. In another aspect, the engineered TCR is further defined as a soluble TCR, wherein the soluble TCR does not comprise a transmembrane domain. In some aspects, the soluble TCR is linked to a CD3-specific antibody. In certain aspects, an extracellular domain of the TCR is fused to an antibody Fc domain. In several aspects, the alpha chain of the TCR extracellular domain is fused to the antibody Fc domain. In some particular aspects, the Fc domain is a human or mouse Fc domain. In another aspect, the engineered TCR further comprises an antibody hinge region.

In yet still further aspects, the engineered CAR is further defined as a chimeric antigen receptor. In another aspect, the engineered TCR further comprises a detectable label. In some aspects, the engineered TCR is covalently bound to a therapeutic agent. In some specific aspects, the therapeutic agent is an immunotoxin or a chemotherapeutic agent.

In an embodiment of the present disclosure, there is provided an engineered T-cell receptor (TCR) comprising an alpha chain CDR3 having the amino acid sequence of any one of SEQ ID NOs: 1-7 or 60-61 and/or a beta chain CDR3 having the amino acid sequence of any one of SEQ ID NOs: 8-17 or 62-63.

In some aspects, the engineered TCR is HLA-A2restricted, such as HLA-A2*02:01 restricted. In particular aspects, the engineered TCR specifically recognizes a peptide comprising an amino acid sequence of NLVPM-VATV (SEQ ID NO: 41) in complex with HLA-A2*02:01. In certain aspects, the engineered TCR comprises an alpha chain CDR3 having the amino acid sequence of SEQ ID NO: 2 and a beta chain CDR3 having the amino acid sequence of SEQ ID NO: 15. In some aspects, the engineered TCR comprises an alpha chain CDR3 having the amino acid sequence of SEQ ID NO: 60 and a beta chain CDR3 having the amino acid sequence of SEQ ID NO: 62. In particular aspects, the engineered TCR comprises an alpha chain CDR3 having the amino acid sequence of SEQ ID NO: 61 and a beta chain CDR3 having the amino acid sequence of SEQ ID NO: 63.

In some aspects, the engineered TCR comprises an alpha chain CDR1 of Table 1A-2 or Table 1C. In specific aspects, the engineered TCR comprises an alpha chain CDR1; CDR2 and CDR3 of Table 1C. In further aspects, the engineered TCR comprises a beta chain CDR1; CDR2 and CDR3 of Table 1D. For example, the engineered TCR may comprise an alpha chain CDR1; CDR2 and CDR3 of Table 1C; and a beta chain CDR1; CDR2 and CDR3 of Table 1D.

In certain aspects, the engineered TCR comprises an alpha chain variable region having at least 90% (e.g., 91%, 92%, 93%, 94%, 95%, 96%, 97%, 98%, or 99%) identity to the amino acid sequence of any one of those in Table 1C and/or a beta chain variable region having at least 90% (e.g., 91%, 92%, 93%, 94%, 95%, 96%, 97%, 98%, or 99%) identity to the amino acid sequence of any one of those in Table 1D. In particular aspects, the engineered TCR comprises an alpha chain of any one of those in Table 1C and/or a beta chain of any one of those in Table 1D. In one specific aspect, the engineered TCR comprises an alpha chain of SEQ ID NO: 19 and a beta chain of SEQ ID NO: 32.

In some aspects, the engineered TCR is further defined as a soluble TCR, wherein the soluble TCR does not comprise a transmembrane domain. In further aspects, the soluble TCR is linked to a CD3-specific antibody. In some aspects, an extracellular domain of the TCR is fused to an antibody Fc domain. For example, the alpha chain of the TCR extracellular domain may be fused to the antibody Fc domain. The Fc domain may be a human or mouse Fc domain. In additional aspects, the TCR further comprises an antibody hinge region.

In certain aspects, the Fc domain exhibits reduced binding a viral Fc receptor (vFcR) relative to a wt Fc. In some aspects, the vFcR comprises CMV gp34 and/or gp68. In particular aspects, the vFcR is able to bind to human FcRIIIa and/or FcRn. In specific aspects, the Fc domain comprises one or more substitutions relative to wt Fc domain selected from a substitution at S337; K334; G341; E345; T350; K338; H268; E294 and Q311. In some aspects, the Fc domain comprises substitutions selected from: (a) S337; (b) S337 and G341; (c) S337; E345; and T350; (d) K334; and K338; (e) S337 and T350; (f) H268; and K334; and (g) H268; E294; Q311; and K334. In certain aspects, the Fc domain comprises one or more substitutions relative to wt Fc domain selected from S337F; K334E; G341E; E345K; T350I; K338I; H268L; E294K and Q311L, wherein the engineered Fc domain exhibits reduced binding a viral Fc receptor (vFcR) relative to a wt Fc. In some aspects, the Fc domain comprises substitutions selected from: (a) S337F; (b) S337F and G341E; (c) S337F; E345K; and T350I; (d) K334E; and K338I; (e) S337F and T350I; (f) H268L; and K334E; and (g) H268L; E294K; Q311L; and K334E. In specific aspects, the Fc domain comprises wherein the antibody Fc domain comprises one or more substitution selected from M252Y; S254T and T256E. In some aspects, the engineered antibody Fc domain comprises the following substitutions M252Y; S254T and T256E.

In some aspects, the engineered TCR is further defined as a chimeric antigen receptor.

In additional aspects, the TCR further comprises a detectable label. In some aspects, the engineered TCR is covalently bound to a therapeutic agent, such as an immunotoxin or a chemotherapeutic agent.

A further embodiment provides a polynucleotide encoding the engineered TCR of the present embodiment and aspects thereof (e.g., an engineered T-cell receptor (TCR) comprising an alpha chain CDR3 having the amino acid sequence of any one of SEQ ID NOs: 1-7 or 60-61 and/or a beta chain CDR3 having the amino acid sequence of any one of SEQ ID NOs: 8-17 or 62-63).

Also provided herein is an expression vector encoding the engineered TCR of the present embodiment and aspects thereof (e.g., an engineered T-cell receptor (TCR) comprising an alpha chain CDR3 having the amino acid sequence of any one of SEQ ID NOs: 1-7 or 60-61 and/or a beta chain CDR3 having the amino acid sequence of any one of SEQ ID NOs: 8-17 or 62-63). In some aspects, the sequence encoding the TCR is under the control of a promoter. The expression vector may be a viral vector, such as a retroviral vector. In other aspects, the expression vector is an episomal vector. In additional aspects, the vector further encodes a linker domain. The linker domain may be positioned between the alpha chain and beta chain. In some aspects, the linker domain comprises one or more cleavage sites, such as a Furin cleavage site (e.g., RRKR (SEQ ID NO:71)) and/or a P2A cleavage site. In certain aspects, the one or more cleavage sites are separated by a spacer, such as SGSG (SEQ ID NO:72) or GSG.

Another embodiment provides a cell engineered to express the TCR of the present embodiment and aspects thereof (e.g., an engineered T-cell receptor (TCR) comprising an alpha chain CDR3 having the amino acid sequence of any one of SEQ ID NOs: 1-7 or 60-61 and/or a beta chain CDR3 having the amino acid sequence of any one of SEQ ID NOs: 8-17 or 62-63). In some aspects, the cell is a T cell, NK cell, invariant NK cell, NKT cell, mesenchymal stem cell (MSC), or induced pluripotent stem (iPS) cell. In particular aspects, the cell is an immune cell. The cell may be isolated from an umbilical cord. In particular aspects, the T cell is a CD8+ T cell, CD4+ T cell, or γδ T cell. In some aspects, the T cell is a regulatory T cell (Treg).

A further embodiment provide a method for engineering the cell of the present embodiments or aspects thereof comprising contacting said immune cell with the TCR of the present embodiment and aspects thereof (e.g., an engineered T-cell receptor (TCR) comprising an alpha chain CDR3 having the amino acid sequence of any one of SEQ ID NOs: 1-7 or 60-61 and/or a beta chain CDR3 having the amino acid sequence of any one of SEQ ID NOs: 8-17 or 62-63) or the expression vector of the present embodiments or aspects thereof. In some aspects, the immune cell is a T cell, peripheral blood lymphocyte, NK cell, invariant NK cell, or NKT cell. In additional aspects, contacting is further defined as transfecting or transducing. In some aspects, transfecting comprises electroporating RNA encoding the TCR of the present embodiments into the immune cell. In further aspects, the method further comprises generating viral supernatant from the expression vector of the present embodiments prior to transducing the immune cell. In some aspects, the immune cell is a stimulated lymphocyte, such as a human lymphocyte. In particular aspects, stimulating comprises contacting the immune cell with or incubating the immune cell in OKT3 and/or IL-2. In additional aspects, the method further comprises sorting the immune cells to isolate TCR engineered T cells. In some aspects, the method further comprising performing T cell cloning by serial dilution. In certain aspects, the method further comprises expansion of the T cell clone by the rapid expansion protocol.

In another embodiment there is provided a polynucleotide encoding the engineered TCR of any of the embodiments and aspects described above.

Still a further embodiment of the invention provides a cell engineered to express the TCR of any of the embodiments and aspects described above. In some aspects, the cell is a T cell, NK cell, invariant NK cell, NKT cell, mesenchymal stem cell (MSC), or induced pluripotent stem (iPS) cell. In certain aspects, the cell is an immune cell. In another aspect, the cell is isolated from an umbilical cord. In several aspects, the T cell is a CD8+ T cell, CD4+ T cell, or γδ T cell. In other aspects, the T cell is a regulatory T cell (Treg).

In still yet a further embodiment, there is provided a method for engineering the cell of any of the embodiments and aspects described above, comprising contacting said immune cell with the TCR of any of the embodiments and aspects described above or the expression vector of any of the embodiments and aspects described above. In certain aspects, the immune cell is a T cell, peripheral blood lymphocyte, NK cell, invariant NK cell, or NKT cell. In another aspect, contacting is further defined as transfecting or transducing. In some aspects, transfecting comprises electroporating RNA encoding the TCR of any of the embodiments and aspects described above into the immune cell. In additional aspects, the method further comprises generating viral supernatant from the expression vector of the embodiments and aspects described above prior to transducing the immune cell.

In further aspects, the immune cell is a stimulated lymphocyte. In some aspects, the stimulated lymphocyte is a human lymphocyte. In several aspects, stimulating comprises contacting the immune cell with or incubating the immune cell in OKT3 and/or IL-2. In additional aspects, the method further comprises sorting the immune cells to isolate TCR engineered T cells. In still further aspects, the method also comprises performing T cell cloning by serial dilution. In another aspects, the method further comprises expansion of the T cell clone by the rapid expansion protocol.

Yet a further embodiment provides use of a therapeutically effective amount of NLV/A2 TCR-specific cells according to any of the embodiments and aspects described above for the treatment of a disease or disorder in a patient. In certain aspects, the NLV/A2 TCR-specific cells are T cells.

Still a further embodiment of the invention provides use of a therapeutically effective amount of a soluble TCR according to any of the embodiments and aspects described above for the treatment of a disease or disorder in a patient.

In yet still a further embodiment of the invention there is provided a method of treating a disease or disorder in a subject in need thereof, monitoring disease progression in a subject, or monitoring vaccine efficacy in a subject, the method comprising administering an effective amount of the TCR-engineered cells of any of the embodiments and aspects described above or a soluble TCR according to any of the embodiments and aspects described above to the subject. In certain aspects, the subject has been identified as having an HLA-A2*02:01 allele. In some aspects, the TCR-engineered cell is a T cell or peripheral blood lymphocyte. In additional aspects, the T cell is a CD8+ T cell, CD4+ T cell, or Treg. In specific aspects, the cell is autologous. In other aspects, the cell is allogeneic. In certain aspects, the disease is a cancer. In a particular aspect, the cancer is a glioblastoma. In some aspects, an NLV peptide has been delivered to cells of the cancer. In several aspects, the subject is a human. In additional aspects, the cells are administered to the subject intravenously, intraperitoneally, or intratumorally. In certain aspects, the method further comprises administering a second anticancer therapy. In some aspects, the second anticancer therapy is a chemotherapy, immunotherapy, surgery, radiotherapy, or biotherapy. In certain aspects, the immunotherapy is an immune checkpoint inhibitor. In another aspect, the immune checkpoint inhibitor inhibits an immune checkpoint protein or ligand thereof selected from the group consisting of CTLA-4, PD-1, PD-L1, PD-L2, LAG-3, BTLA, B7H3, B7H4, TIM3, KIR, or adenosine A2a receptor (A2aR). In several aspects, the immune checkpoint inhibitor inhibits PD-1 or CTLA-4. In some aspects, the patient has been determined to have a cancer with a reactivated CMV infection.

Still a further embodiment provides a method of detecting NLV/A2 complexes on cells, the method comprising contacting the cells with a soluble TCR of any one of claims 11-16 and 18 and detecting binding of the soluble TCR to the cells. In certain aspects, the soluble TCR comprises a mouse Fc domain. In some aspects, the cells are peptide-pulsed antigen presenting cells. In other aspects, the antigen presenting cells have been pulsed with a peptide comprising an amino acid sequence of NLVPMVATV (SEQ ID NO: 41).

Yet still a further embodiment provides an immunoglobulin fusion complex comprising: (i) an αTCR variable domain fused to a first antibody Fc domain, wherein αTCR variable domain is bound to a βTCR variable domain by a disulfide bond; or (ii) a βTCR variable domain fused to a first antibody Fc domain, wherein βTCR variable domain is bound to an αTCR variable domain by a disulfide bond, wherein the αTCR variable domain and the βTCR variable domain comprise amino acid substitutions that block N-linked glycosylation. In some aspects, the first antibody Fc domain is bound to a second antibody Fc domain by a disulfide bond. In certain aspects, the second antibody Fc domain is fused to an antibody heavy chain variable domain that is bound to an antibody light chain by a disulfide bond. In several aspects, the complex further comprises two immunoglobulin fusion complexes that are bound by disulfide bonds between the Fc domains. In some aspects, the second Fc domain is fused to a targeting moiety. In certain aspects, the targeting moiety is an antibody VH/VL domain. In another aspect, the targeting moiety binds to immune effector cells. In some aspects, the targeting moiety binds to CD3. In further aspects, the αTCR variable domain is bound to a βTCR variable domain by two disulfide bonds. In certain aspects, the αTCR variable domain and the βTCR variable domain comprise N to Q amino acid substitutions that block N-linked glycosylation. In other aspects, the αTCR variable domain and the βTCR variable domain specifically bind to a peptide in complex with HLA. In some specific aspects, the HLA is HLA-A2. In certain aspects, the peptide in complex with HLA is a cancer protein peptide, an autoimmune peptide or an infectious disease peptide. In another aspect, the peptide is a CMV peptide. In some particular aspects, the CDR3 domains of the TCR variable domains are those recited in the first embodiment described above.

In yet a further embodiment, there is provided a method of producing a TCR complex comprising (a) expressing one or more nucleic acid molecules in a mammalian cell encoding: (i) an αTCR variable domain fused to a first antibody Fc domain, wherein αTCR variable domain is bound to a βTCR variable domain by a disulfide bond; or (ii) a βTCR variable domain fused to a first antibody Fc domain, wherein βTCR variable domain is bound to an αTCR variable domain by a disulfide bond, wherein the αTCR variable domain and the βTCR variable domain comprise amino acid substitutions that block N-linked glycosylation; and (b) collecting or purifying the TCR complex. In some aspects, the mammalian cell is CHO cell. Also provided herein is a TCR complex produced by the present methods.

Further provided herein is an engineered antibody Fc domain comprising one or more substitutions relative to wt Fc domain selected from a substitution at S337; K334; G341; E345; T350; K338; H268; E294 and Q311, wherein the engineered Fc domain exhibits reduced binding a viral Fc receptor (vFcR) relative to a wt Fc. In some aspects, the Fc domain comprises substitutions selected from: (a) S337; (b) S337 and G341; (c) S337; E345; and T350; (d) K334; and K338; (e) S337 and T350; (f) H268; and K334; and (g) H268; E294; Q311; and K334. In certain aspects, the Fc domain comprises one or more substitutions relative to wt Fc domain selected from S337F; K334E; G341E; E345K; T350I; K338I; H268L; E294K and Q311L, wherein the engineered Fc domain exhibits reduced binding a viral Fc receptor (vFcR) relative to a wt Fc. In certain aspects, the Fc domain comprises substitutions selected from: (a) S337F; (b) S337F and G341E; (c) S337F; E345K; and T350I; (d) K334E; and K338I; (e) S337F and T350I; (f) H268L; and K334E; and (g) H268L; E294K; Q311L; and K334E. In some aspects, the vFcR comprises CMV gp34 and/or gp68. For example, the vFcR may be CMV gp34. In particular aspects, the engineered Fc domain is able to bind to human FcRIIIa and/or FcRn. In some aspects, the engineered Fc domain comprises a CH1, CH2 and CH3 domain at least 85%, 86%, 87%, 88%, 89%, 90%, 91%, 92%, 93%, 94%, or 95% identical to a human IgG1 CH1, CH2 and CH3. In some aspects, the engineered Fc domain is an IgG1 Fc domain or an IgG2 Fc domain. In some aspects, the engineered Fc domain is at least 85%, 86%, 87%, 88%, 89%, 90%, 91%, 92%, 93%, 94%, or 95% identical to any one of SEQ ID NOs: 53-60. In additional aspects, the method Fc domain further comprises one or more substitutions selected from M252; S254 and T256. In some aspects, the Fc domain further comprises a substitution at M252; S254 and T256. In certain aspects, the Fc domain further comprises one or more substitution selected from M252Y; S254T and T256E. In some aspects, the Fc domain further comprises the following substitutions M252Y; S254T and T256E. In some aspects, the Fc domain further comprises an antibody variable domain or a TCR variable domain. The engineered Fc domain may be fused or conjugated to antibody variable domains or TCR variable domains that bind to a target of interest, such as a viral protein or a viral peptide bound to HLA. In some aspects, the target of interest is a CMV protein or a CMV peptide bound to HLA. In particular aspects, the engineered Fc domain is fused or conjugated to TCR variable domains that bind to NLVPMVATV (SEQ ID NO: 41) in complex with HLA-A2*02:01. Also provided herein is nucleic acid molecule encoding an engineered antibody Fc domain of the present embodiments and aspects thereof. Further provided herein is host cell expressing a nucleic acid molecule of the present embodiments. For example, the cell is a CHO cell.

Another embodiment provides a method of targeting a CMV infected cell comprising contacting the cell with molecule that binds to a CMV polypeptide or a CMV peptide bound to HLA, wherein the molecule is fused or conjugated to an engineered antibody Fc domain comprising one or more substitutions relative to wt Fc domain selected from a substitution at S337; K334; G341; E345; T350; K338; H268; E294; Q311; M252; S254; and T256, wherein the engineered Fc domain exhibits reduced binding a viral Fc receptor (vFcR) relative to a wt Fc. In some aspects, the engineered antibody Fc domain comprises one or more substitution selected from M252Y; S254T and T256E. In certain aspects, the engineered antibody Fc domain comprises the following substitutions M252Y; S254T and T256E. In some aspects, the engineered antibody Fc domain is a domain in accordance with the present embodiments or aspects thereof.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

(FIG. 1A) The RA14 variable and constant regions were cloned in-frame with the mouse/human Ig heavy leader sequence (LS), a T2A peptide for cleavage, and the PDGFR transmembrane region (TM) with either the alpha ($\alpha/\beta$-TM) or the beta chain ($\beta/\alpha$-TM) in the first position. The cassettes were then cloned into a pcDNA3 mammalian expression vector. (FIG. 1B) Display of functional RA14 TCR was detected with a dual-stain approach, with an anti-V$\beta$6-5 antibody-PE conjugate detecting expression of the TCR beta chain, and a peptide/A2 tetramer conjugated to APC used to assess ligand binding. (FIG. 1C) Plasmids encoding the TCR in both chain orientations and with the wild-type (WT) or engineered disulfide (ds) constant regions were transfected, stained two days later, and assayed for APC and PE signal via flow cytometry.

Rainbow dots depict staining using a tetramer with the specific NLV peptide, while grey dots depict staining with a tetramer containing a control peptide from HCV. Control transfections without plasmid and with a plasmid lacking the alpha chain are also shown.

Figure 2A:
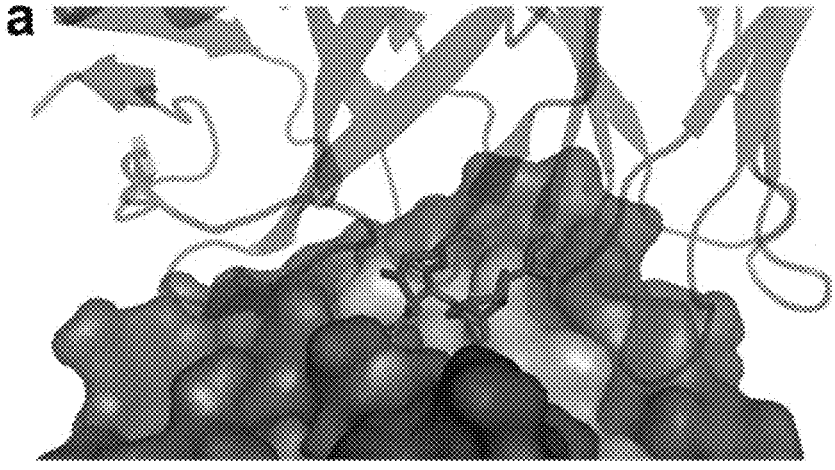
Figure 2B:
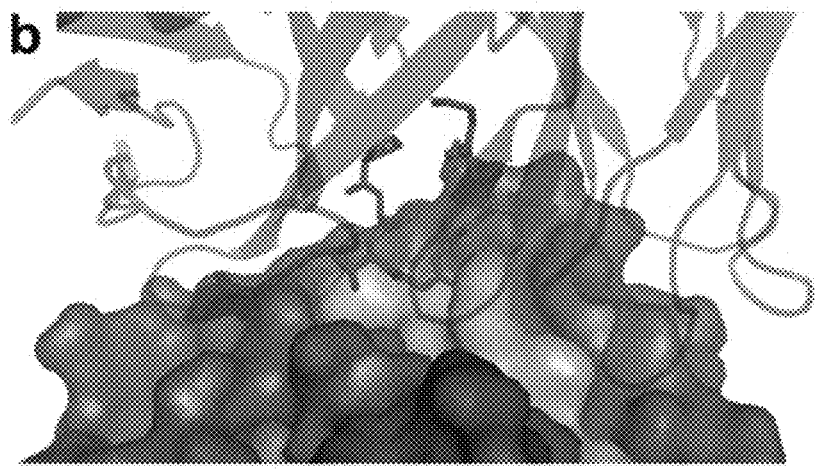

FIGS. 2A-2B: Structural interactions between RA14 CDR3 loops and NLV peptide/A2. The crystal structure of the RA14 TCR complexed with NLV/A2 (PDB 3GSN) was used to guide library design. The A2 surface is shown in grey space-fill, the NLV peptide surface in pink space-fill and the RA14 structure in purple ribbon. The residues comprising the CDR3$\alpha$ (SEQ ID NO: 39) (FIG. 2A) and CDR30 (SEQ ID NO: 40) loops (FIG. 2B) are listed (IMGT definition), with those targeted for mutagenesis highlighted in red in the text and in the structure. Boxed residues form direct pMHC contacts in the wild-type crystal as analyzed by (Gras et al., 2009).

FIGS. 3A-3D: RA14 variants with improved tetramer binding can be isolated by CHO display. The TCR display cassette optimized in FIG. 1 was mutagenized into two libraries following the strategy in FIG. 2, and cloned into a pPy vector to allow episomal maintenance (see U.S. Pat. No. 7,919,270). The CDR3$\alpha$ (FIG. 3A) and CDR3$\beta$ (FIG. 3B) libraries were separately transfected into CHO-T cells, stained and sorted over three rounds to enrich for improved tetramer binding. Untransfected cells and cells displaying Fab huIB7 (Nguyen et al., 2015) are shown as controls. The gate drawn is representative of the sorting gate used in round three, with the percentage of cells falling into the gate noted in red to facilitate comparisons. Individual clones from the round three sorts of the CDR3$\alpha$ (FIG. 3C) and CDR3$\beta$ (FIG. 3D) libraries were re-transfected, stained, and checked for improved specific tetramer binding compared to the wild-type sequence. Specific tetramer binding refers to the ratio of the AF647 signal (tetramer binding) to the PE signal (anti-TCR$\beta$ display) calculated on a per-cell basis. The median fluorescence intensity for this new variable was normalized to the wild-type. Variants selected for further characterization are indicated by an asterisk (*). In this initial screening experiment there were no replicate transfections, therefore no error bars are indicated.

Figures 3A, 3B, 3C, 3D:
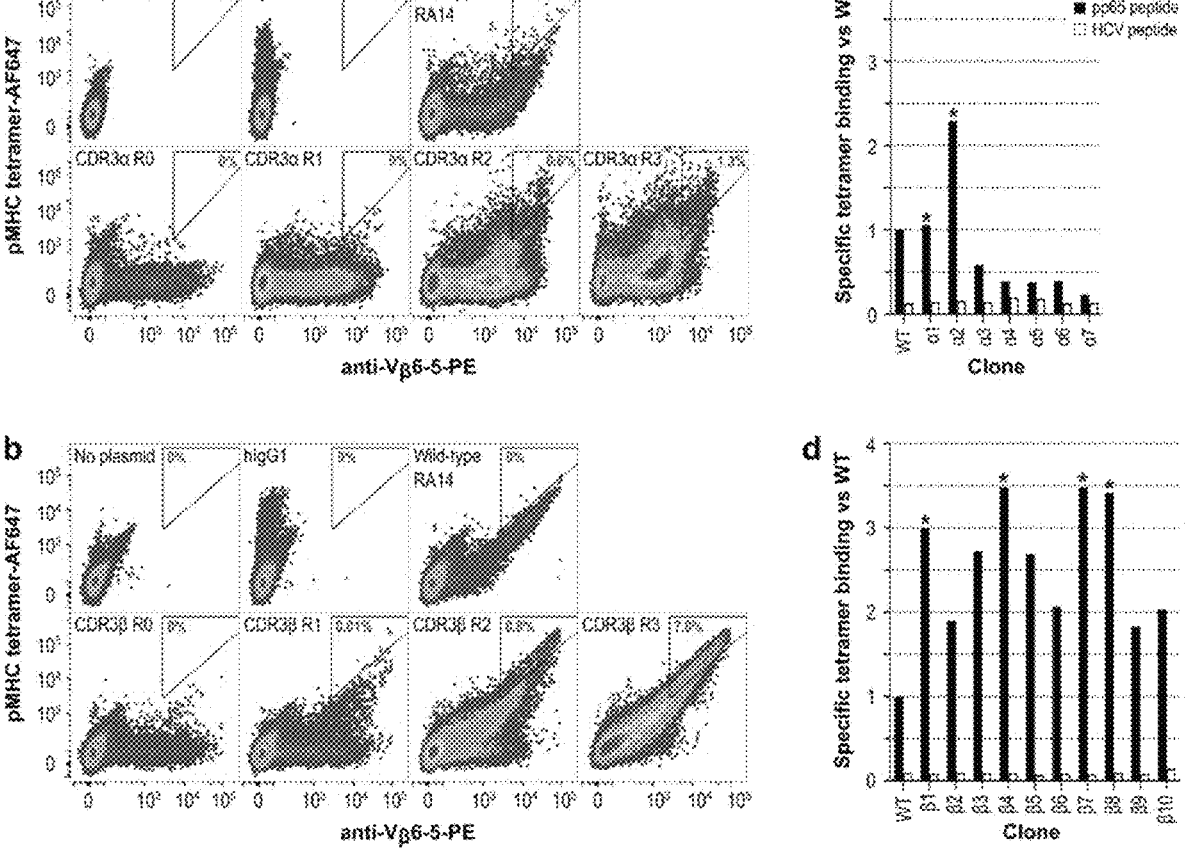
Figure 4A:
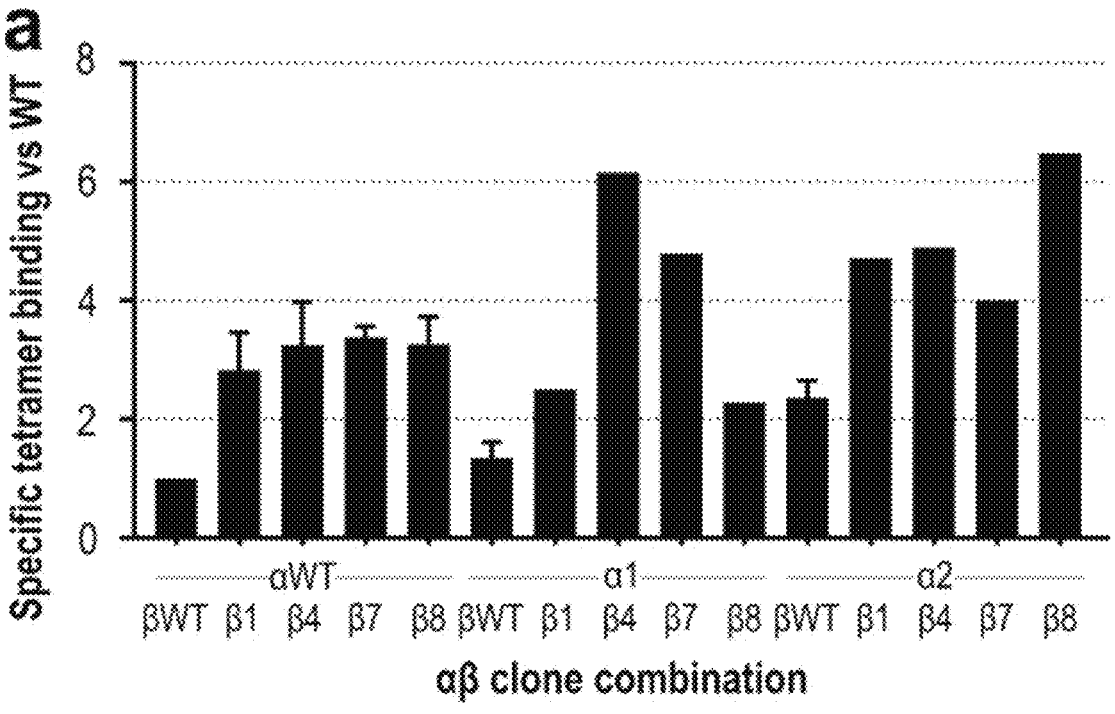
Figure 4B:
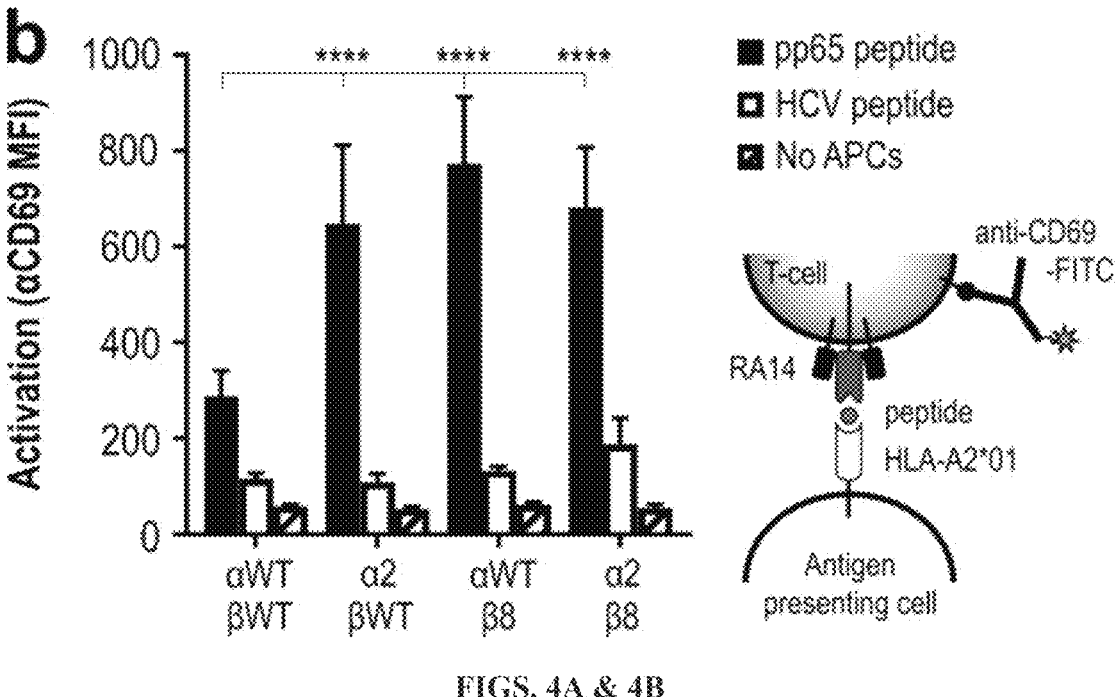

FIGS. 4A-4B: Combining selected CDR3 variants further improves NLV/A2 tetramer staining and activation. (FIG. 4A) The wild-type and improved alpha-chain variants ($\alpha1$ and $\alpha2$) were cloned in combination with the wild-type and improved beta-chain variants ($\beta V1$, $\beta V4$, $\beta V7$, $\beta V8$) in the display format and expressed in CHO-T cells. After two days, cells were stained and analyzed by flow cytometry, with specific tetramer binding quantified as in FIG. 3. The standard deviation is shown for combinations that were tested multiple times. (FIG. 4B) Activation of human Jurkat T cells expressing RA14 and selected variants was measured by CD69 upregulation. Transfected cells were co-cultured with peptide-pulsed human T2 antigen-presenting cells. After 24 hours, TCR-positive cells (NLV-tetramer-binding and V$\beta$-positive) were further monitored for CD69 upregulation using anti-CD69- FITC antibody. Data shows the average and standard deviation of three independent experiments. ANOVA was used to compare tetramer MFI for each clone combination (****p<0.001).

Figures 5A, 5B, 5C:
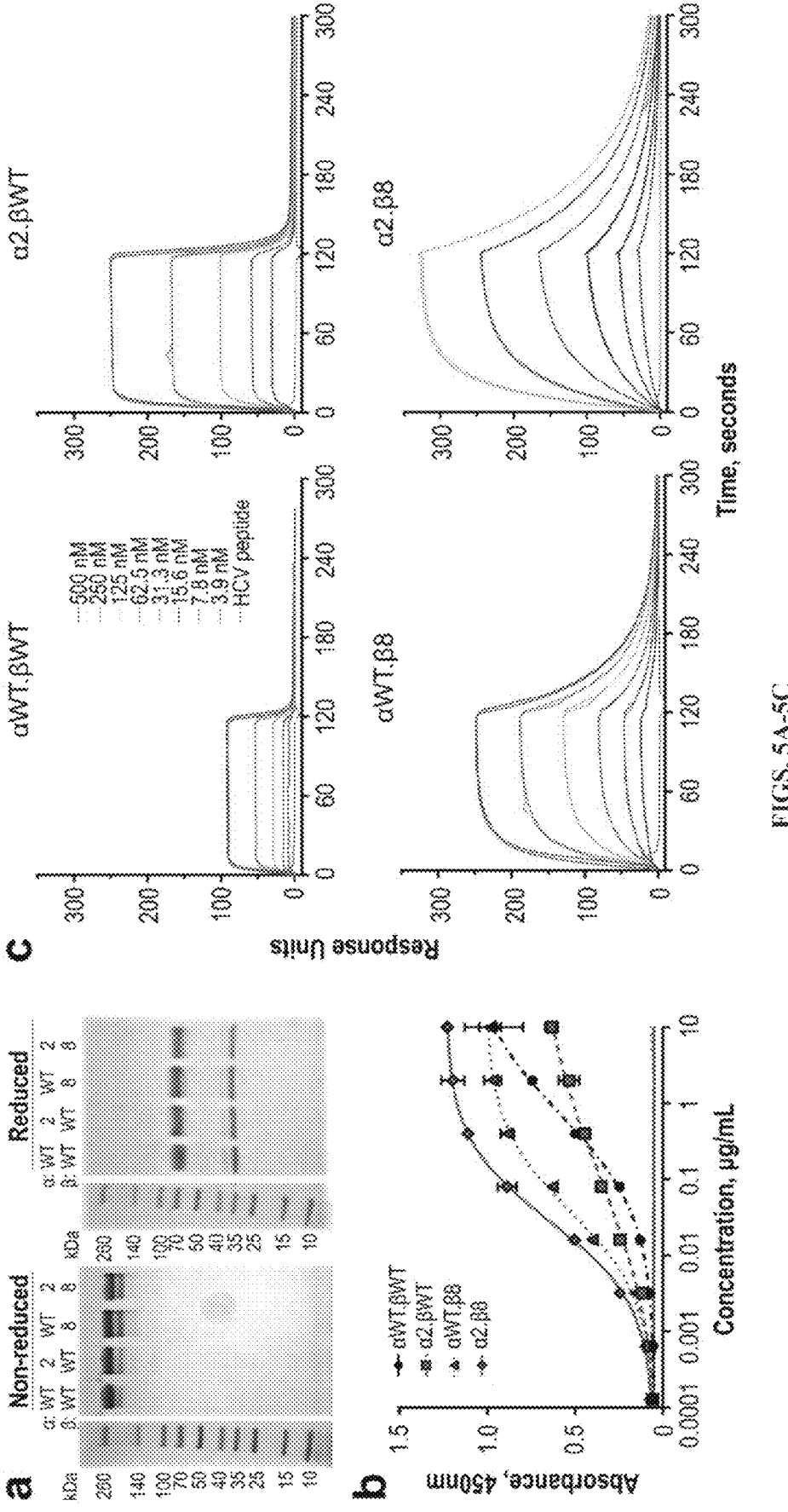
Figures 6A, 6B, 6C, 6D:
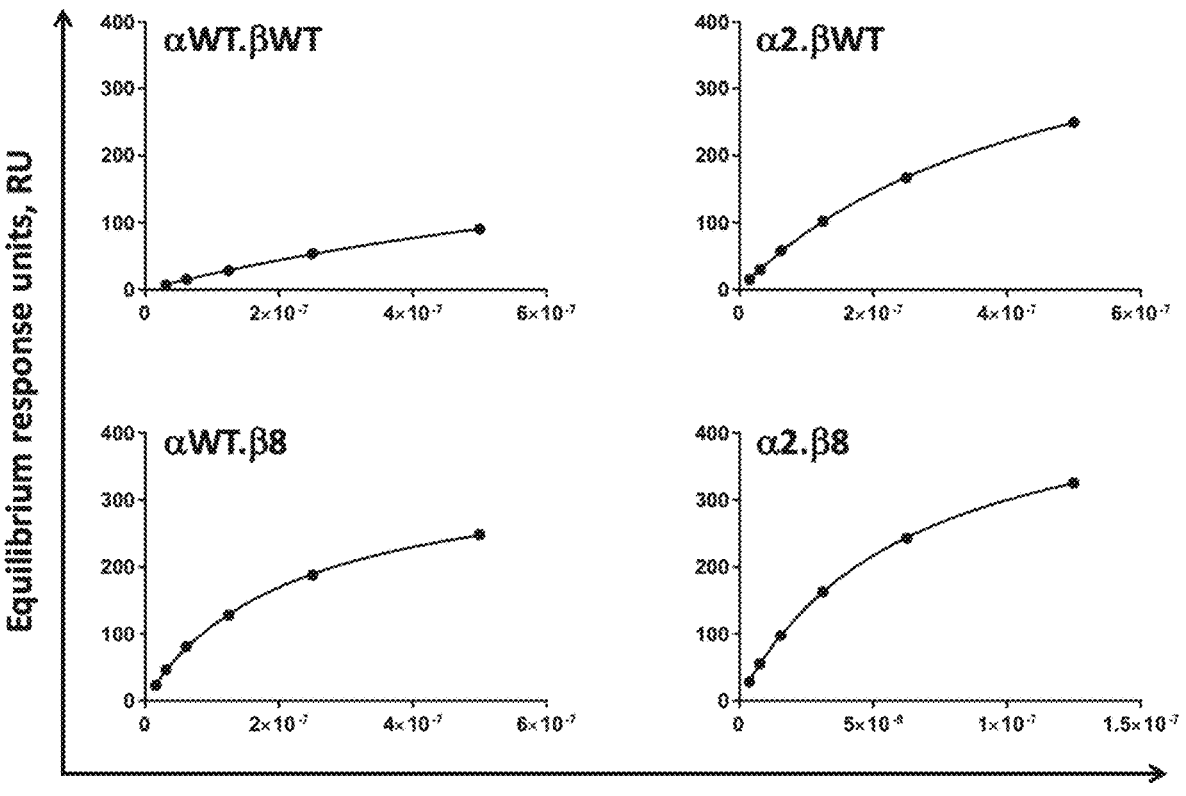

FIGS. 5A-5C: Engineered RA14 TCR2ds-huFc variants show increased affinity for NLV/A2. (FIG. 5A) TCR2ds-huFc formats of each variant were purified by protein A and size-exclusion chromatography to isolate only the intact protein. Protein purity was evaluated by non-reduced and reduced 4-20% gradient SDS-PAGE gel (3 µg protein per lane). (FIG. 5B) The tetramer binding activities of purified RA14 variants were compared by ELISA. Plates were coated with NLV/A2 tetramer, followed by TCR2ds-huFc and goat-anti-human Fc-HRP. Data shown are the average and range of duplicate series for a representative experiment; this was repeated several times with similar results. (FIG. 5C) The binding kinetics were measured by SPR. Each TCR2ds-huFc variant was immobilized on a CM5 chip at 2000-5000 RUs, after which monomeric NLV/A2 was injected at six concentrations between 3.9-500 nM. An in-line blank flow cell was used to assess background binding. Peptide specificity was evaluated with injections of monomeric HCV/A2 at the maximum concentration used for NLV/A2 for each variant. All injections were performed in duplicate; shown are the data and fits with the kinetics reported in Table2.

FIGS. 6A-6D: Equilibrium binding affinity of RA14 and variants for NLV/A2. The wild-type RA14 TCR2ds-huFc fusion and variants were immobilized on a CM5 chip at 2000-5000 RUs before injecting monomeric NLV/A2 at concentrations ranging from 7.9 to 500 nM at a flowrate of 30 ul/min. The observed equilibrium response values were plotted against concentration using BIAevaluation 3.0 software. The equilibrium affinity Kd was calculated using least-squares fit to the data, assuming a 1:1 stoichiometry; numerical values listed in Table 2. No binding was observed with the control HCV/A2 monomer at the highest concentrations used for each variant (shown in FIG. 7).

FIGS. 7A-7D: Expression and stability of the wild-type RA14 TCR as a soluble Fc fusion protein. (FIG. 7A) Several iterations of the TCR-Fc fusion protein were designed. In all scaffolds, the TCR α chain was fused to a human IgG1 hinge and Fc. Open circles represent native glycosylation sites. Additional modifications include a second disulfide bond (ds, green) in the TCR2ds-huFc format and the removal of predicted N-linked glycosylation sites (Δgly, blue crosses) in the TCR2dsΔgly-huFc format. (FIG. 7B) The purity of each protein A purified design was evaluated via reducing and non-reducing 4-20% gradient SDS-PAGE, with 3 μg loaded per lane. (FIG. 7C) Protein homogeneity was analyzed by size exclusion chromatography. The arrow indicates the major peak collected for experiments using a glycosylated scaffold. Triangles indicate elution volumes for molecular weight standards: thyroglobulin with a 669 kDa size eluted at 8.65 ml; ferritin 440 kDa at 10.45 ml; aldolase 158 kDa at 12.77 ml; conalbumin 75 kDa at 14.32 ml; ovalbumin 44 kDa at 15.27 ml; carbonic anhydrase 29 kDa at 16.68 ml. Representative data are shown for each design. (FIG. 7D) The melting temperature of each design was analyzed by differential scanning fluorimetry. An average value for two separate normalized curves shown for each scaffold, from a representative experiment. For FIG. 7C and FIG. 7D, dotted black lines correspond to the TCR-Fc scaffold, the dashed green lines correspond to the TCR2ds-huFc scaffold, and the solid blue lines are used for the TCR2dsΔgly-huFc scaffold.

Figures 8A, 8B:
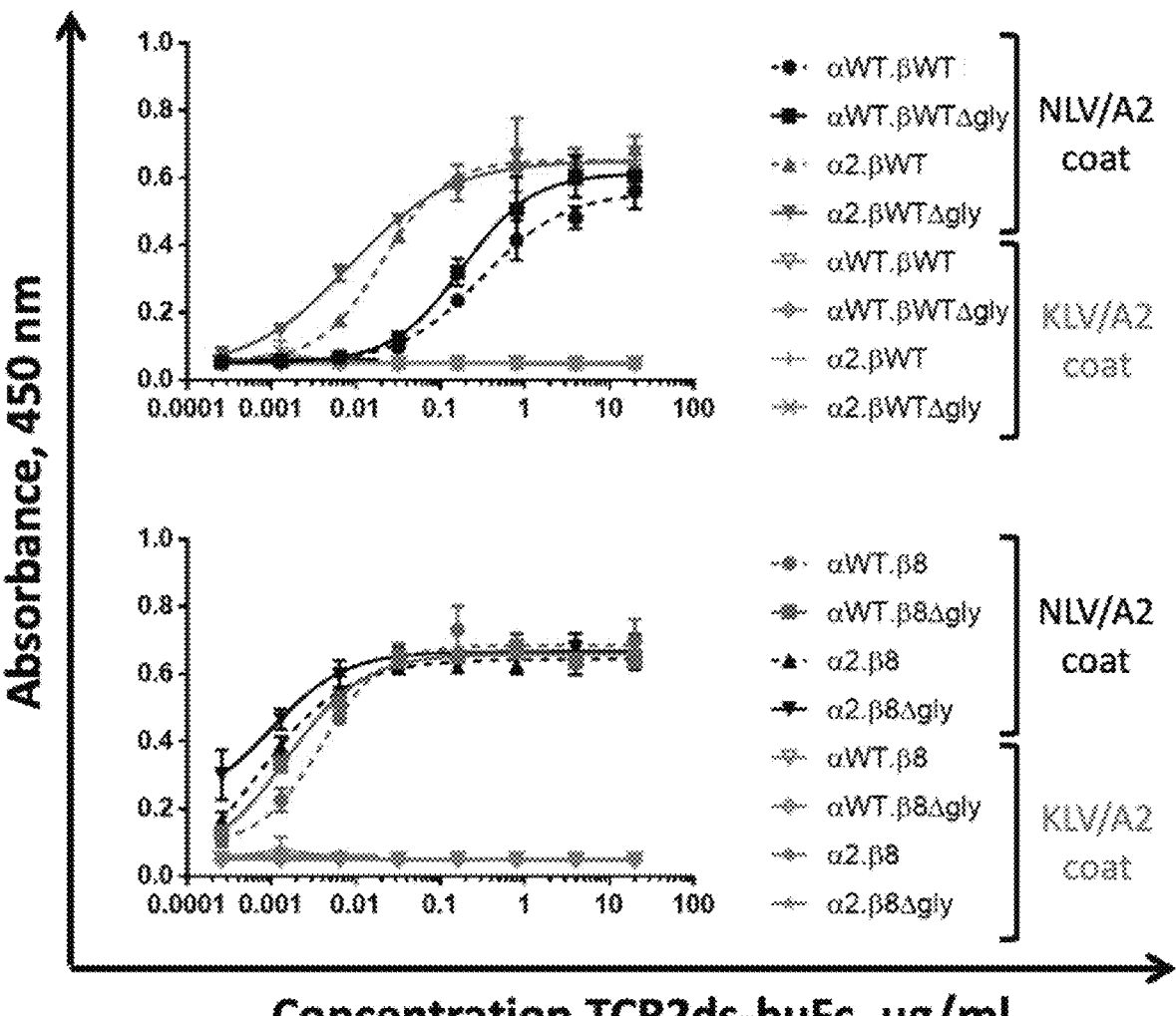

FIGS. 8A-8B: ELISA shows no impact of TCR2ds-huFc de-glycosylation on pMHC binding. The tetramer binding activities of RA14 variants genetically deglycosylated (TCR2dsΔgly-huFc) versus unmodified (TCR2ds-huFc) were compared by ELISA. Plates were coated with NLV/A2 tetramer at 1 μg/mL, followed by serially diluted TCR2ds-huFc or TCR2dsΔgly-huFc and 1:1000 goat-anti-human Fc-HRP. Data shown are the average and range of duplicate series; the experiment was repeated several times with similar results. No coat and an irrelevant peptide (HCV/A2 tetramer) controls were performed in parallel and showed no binding.

Figures 9A, 9B, 9C:
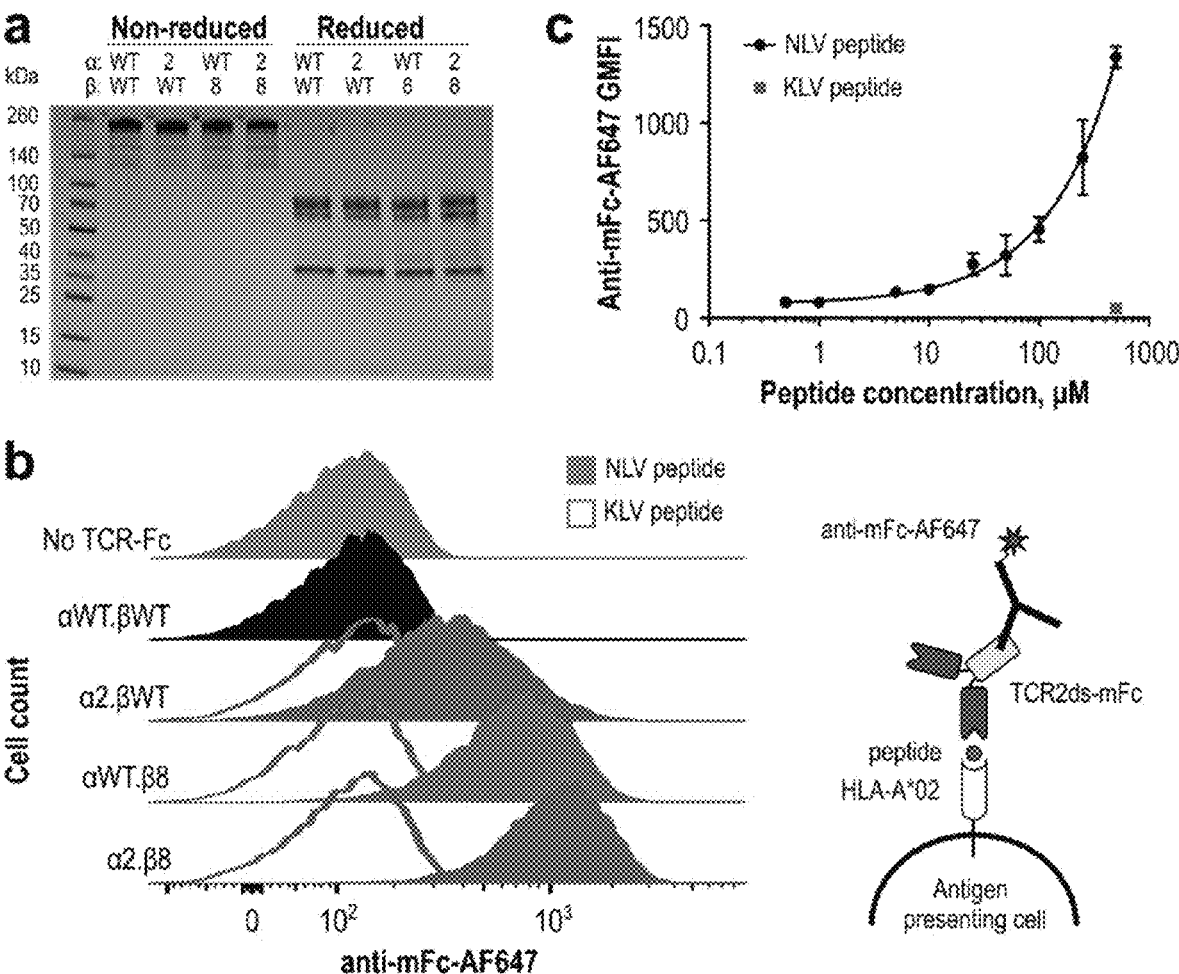

FIGS. 9A-9C: High affinity TCR-mFc proteins bind peptide-pulsed antigen presenting cells. (FIG. 9A) The wild-type (WT) RA14 and improved variants were expressed as TCR2ds-mFc proteins with mouse IgG2a hinge and Fe domains to reduce binding to human Fc receptors expressed on T2 cells. SDS-PAGE was used to confirm protein purity (3 μg per lane). (FIG. 9B) Human T2 antigen presenting cells were pulsed overnight with 100 μM NLV or HCV peptide and stained with 1 μM TCR2ds-mFc and 1:500 anti-mouse Fc-AF647 before flow cytometric analysis. This experiment was performed twice with similar results. (FIG. 9C) Human T2 antigen presenting cells were pulsed overnight with NLV at 0, 0.5, 1, 5, 10, 25, 50, 100, 250, and 500 μM NLV or HCV peptide at 500 μM and stained with 1 μM αV2.βV8 in the TCR2dsΔgly-mFc format and 1:500 anti-mouse Fc-AF647 before flow cytometric analysis. This experiment was performed twice with similar results. Binding was significant over signals observed for HCV pulsed T2 cells to NLV peptide concentrations as low as 0.5 μM.

Figures 10A, 10B, 10C:
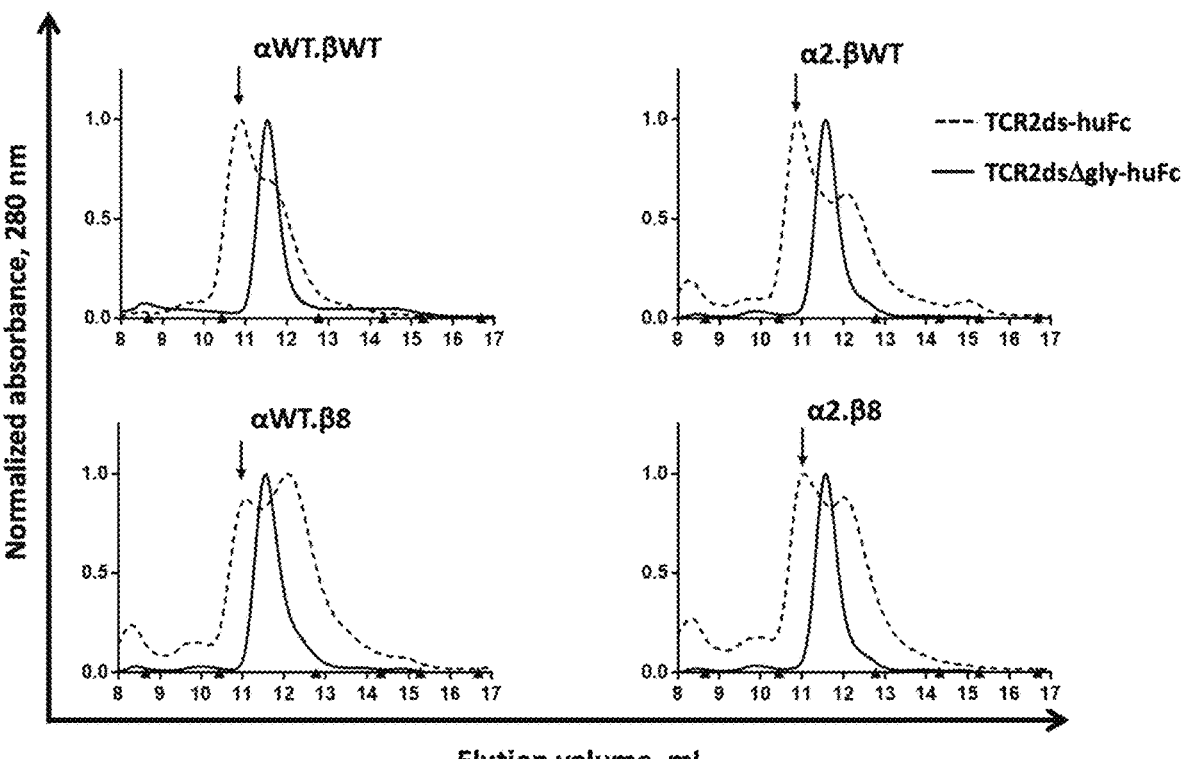

FIGS. 10A-10C: Genetic de-glycosylation of TCR2ds-huFc fusion proteins yields monodisperse protein. The purity of TCR2dsΔgly-huFc (solid lines) and TCR2ds-huFc (dashed lines) proteins for affinity matured RA14 variants was analyzed by size exclusion chromatography. Protein A purified protein was injected (100 μg in 100 μl) onto a Superdex S200 column on an Åkta FPLC. Triangles indicate elution volumes for the molecular weight standards: thyroglobulin with a 669 kDa size eluted at 8.65 ml; ferritin 440 kDa at 10.45 ml; aldolase 158 kDa at 12.77 ml; conalbumin 75 kDa at 14.32 ml; ovalbumin 44 kDa at 15.27 ml; carbonic anhydrase 29 kDa at 16.68 ml. Representative data are shown for each TCR variant in each format.

Figure 11:
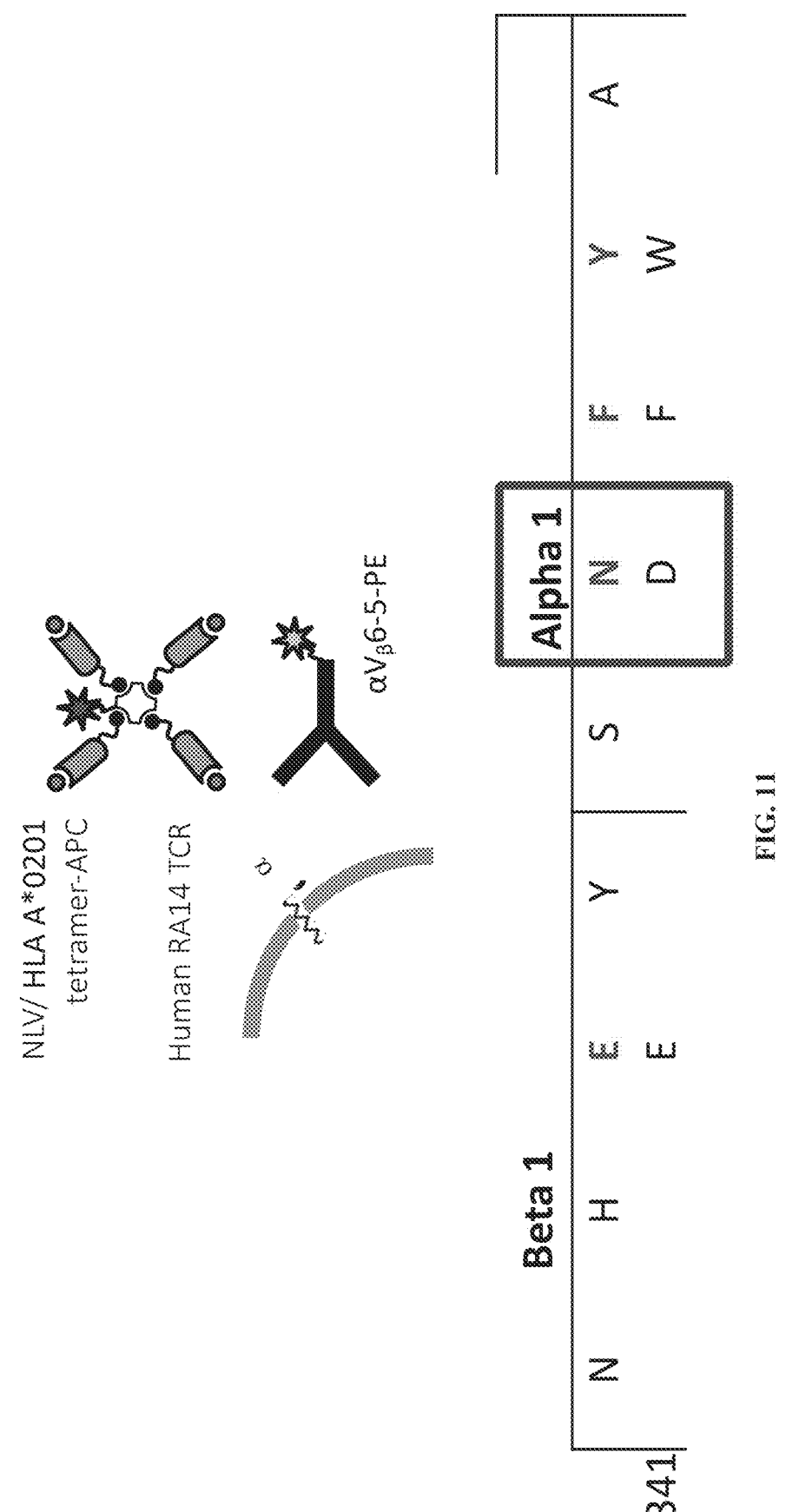

FIG. 11: Schematic representation of improved RA14 TCR variant, 341 (SEQ ID NO: 52) having the transmembrane linker on the alpha chain and eliminating the predicted glycosylation sites with N→Q amino acid substitutions.

Figure 12:
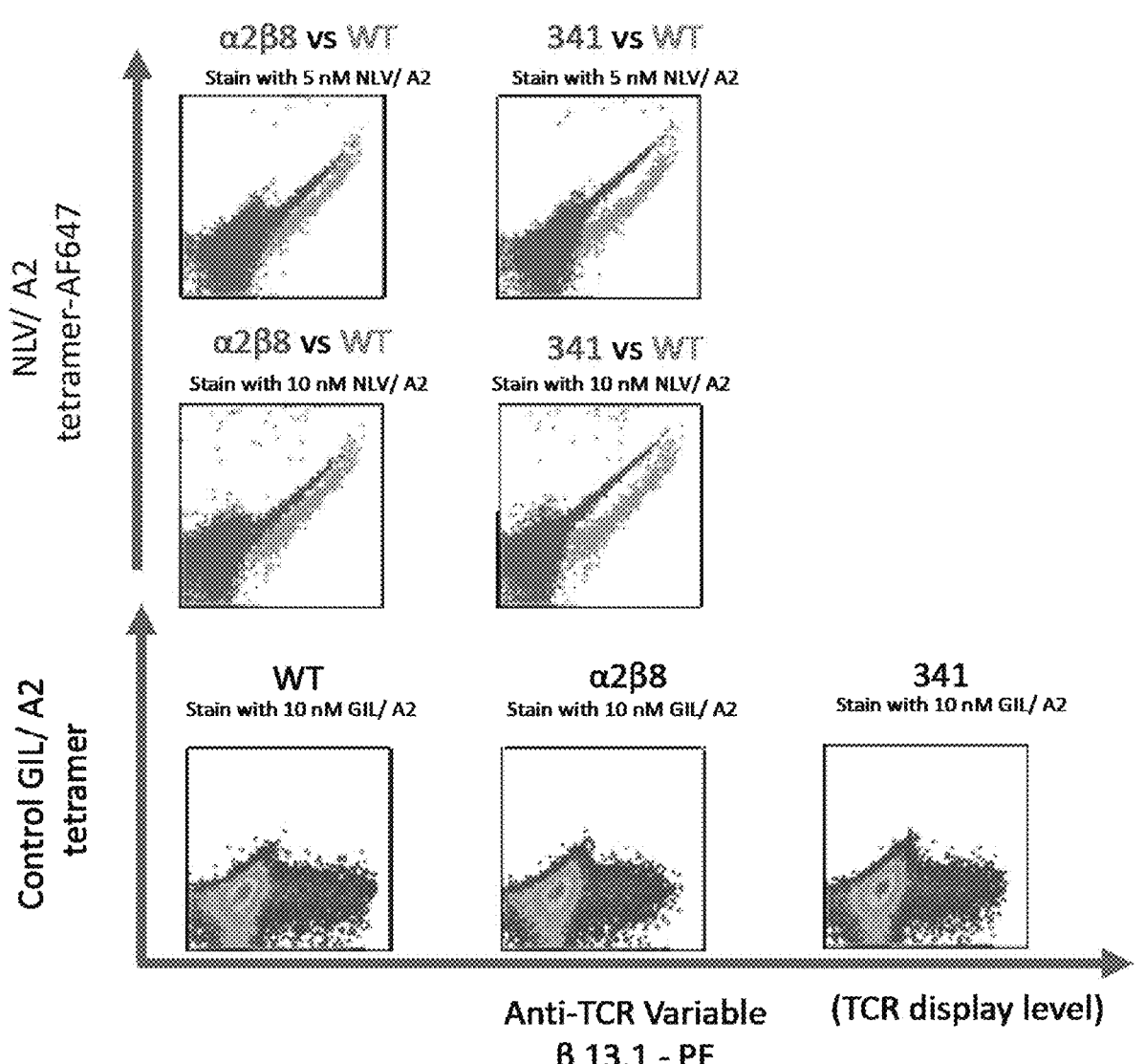

FIG. 12: FACS comparison of α2β8 and 341 against the corresponding wild-type RA14.

Figure 13:
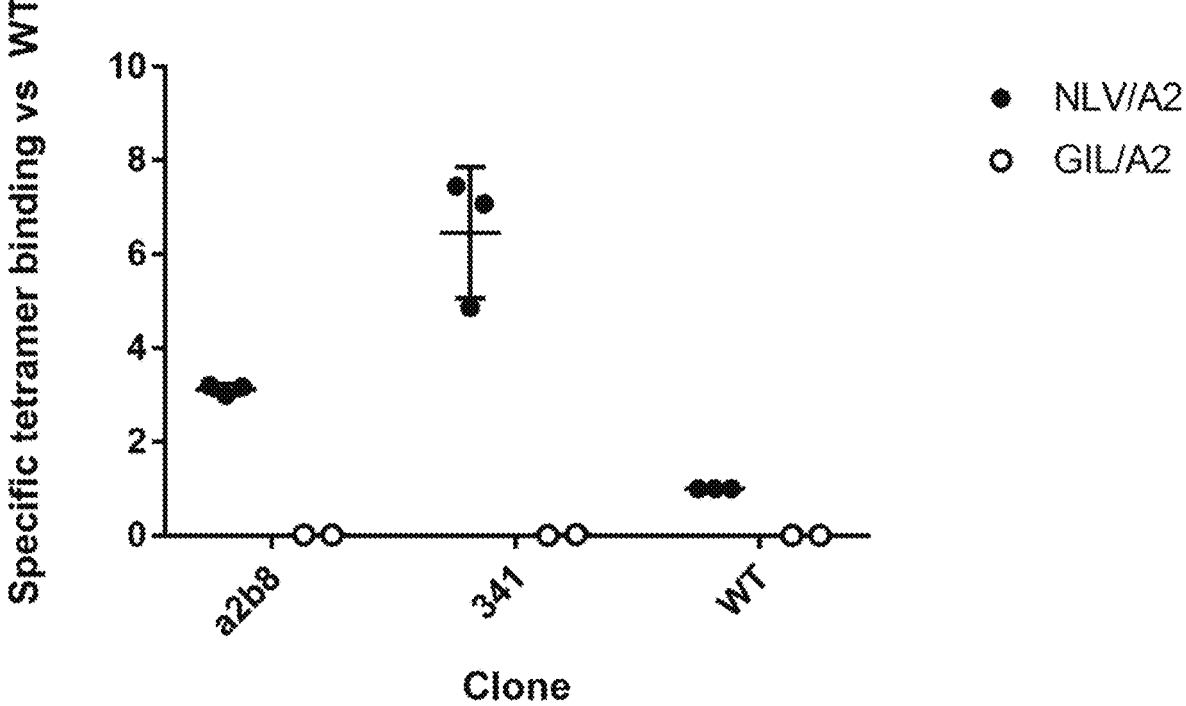

FIG. 13: Graphical representation of enhancement in binding/expression (AF647/PE) shown in FIG. 12.

FIG. 14A-C: Expression and purification of the human Ob.1A12 TCR as a TCR-human Fe fusion protein from CHO cells. Human Ob 1A12 was isolated from a patient with multiple sclerosis. The protein was expressed as a TCR-human Fc fusion in CHO cells. In these constructs, the α chain was fused to human Fc. Both constant chains but not the variable domains were glycosylated. A, SDS-PAGE protein gel. Light chain (β): 30 kDa Heavy Chain (αFc): 51 kDa. B, Size exclusion chromatography using an 5200 column on an Akta FPLC shows homogenous product. Molecular weight markers suggest size is similar to that expected for a glycosylated protein (~160 kDa plus sugars). C, ELISA demonstrates specific binding of the purified Ob.1A12 TCR-Fc protein to its corresponding peptide-MHC complex. Plates were coated with 85-99MBP/DRB1*1501 protein or MHC with the control peptide CLIP, CLIP/DRB1*1501 (both obtained from the NIH tetramer facility), purified TCR added and detected with goat anti-human Fc-HRP.

Figures 15, 16A:
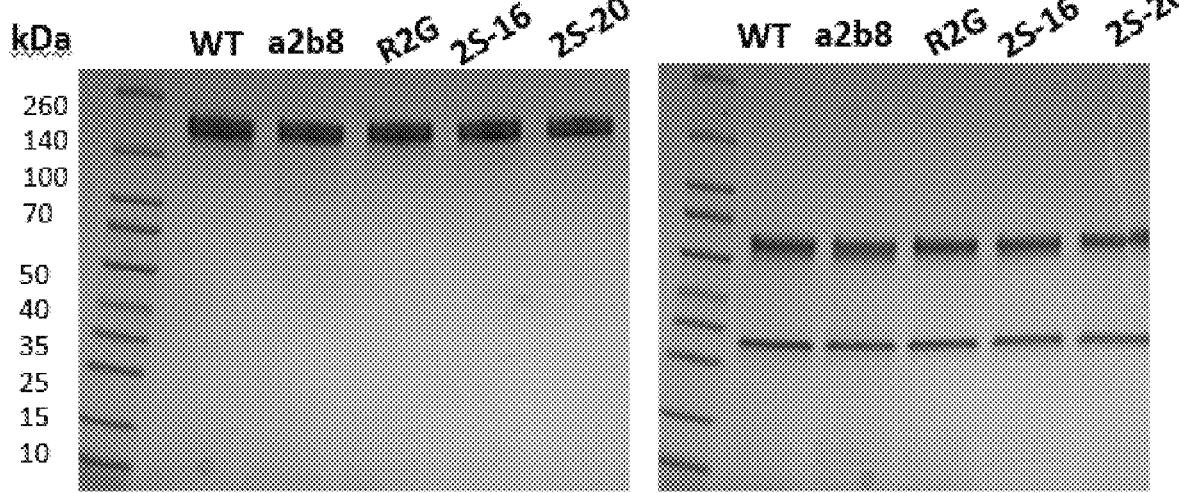

FIG. 15: Sequence changes in the CDRs conferring improved pp65/A2 binding affinity to the RA14 TCR. Positions indicated by arrows are of greatest interest; no changes were identified outside these regions.

Figure 16B:
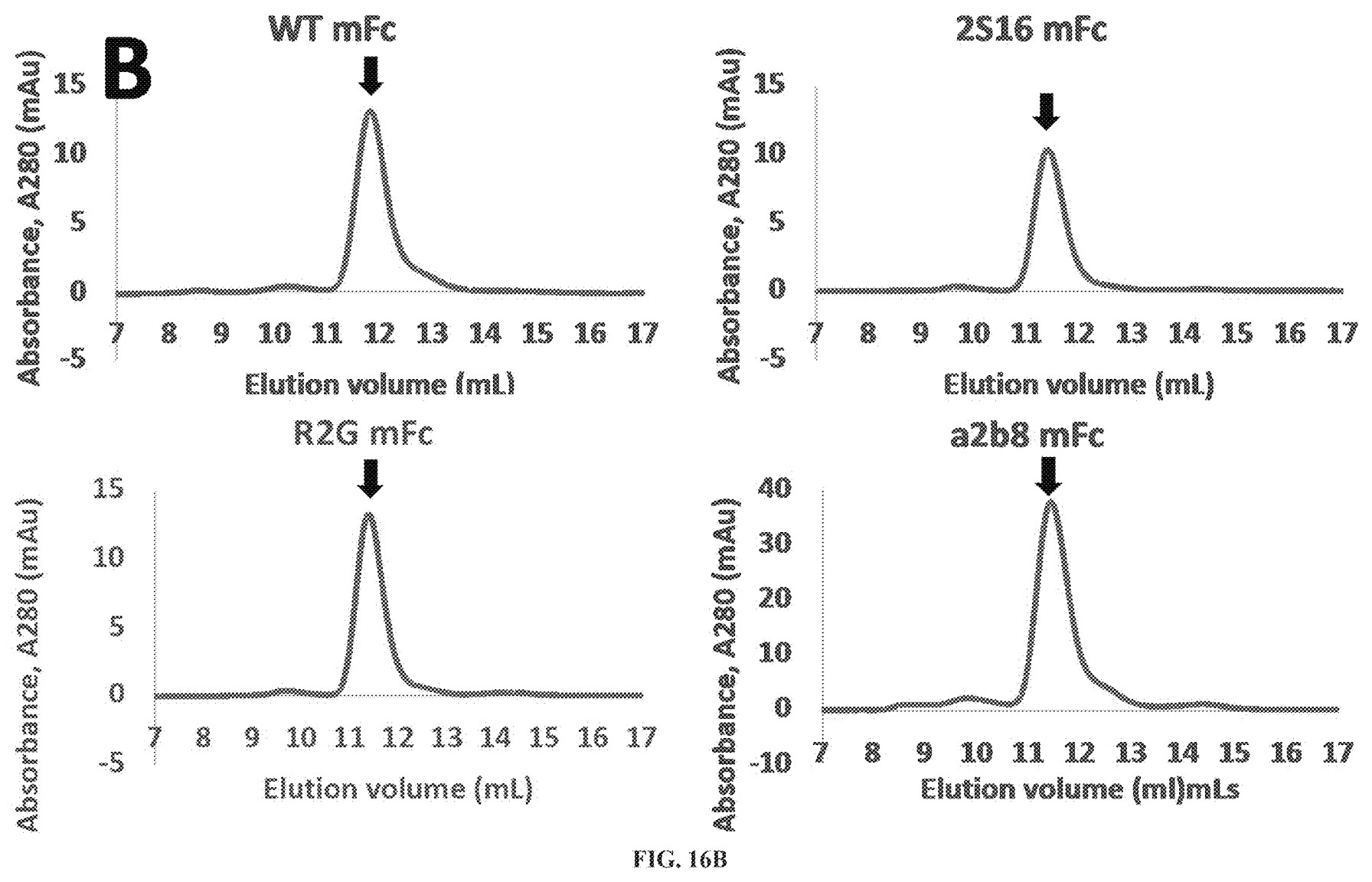
Figure 16C:
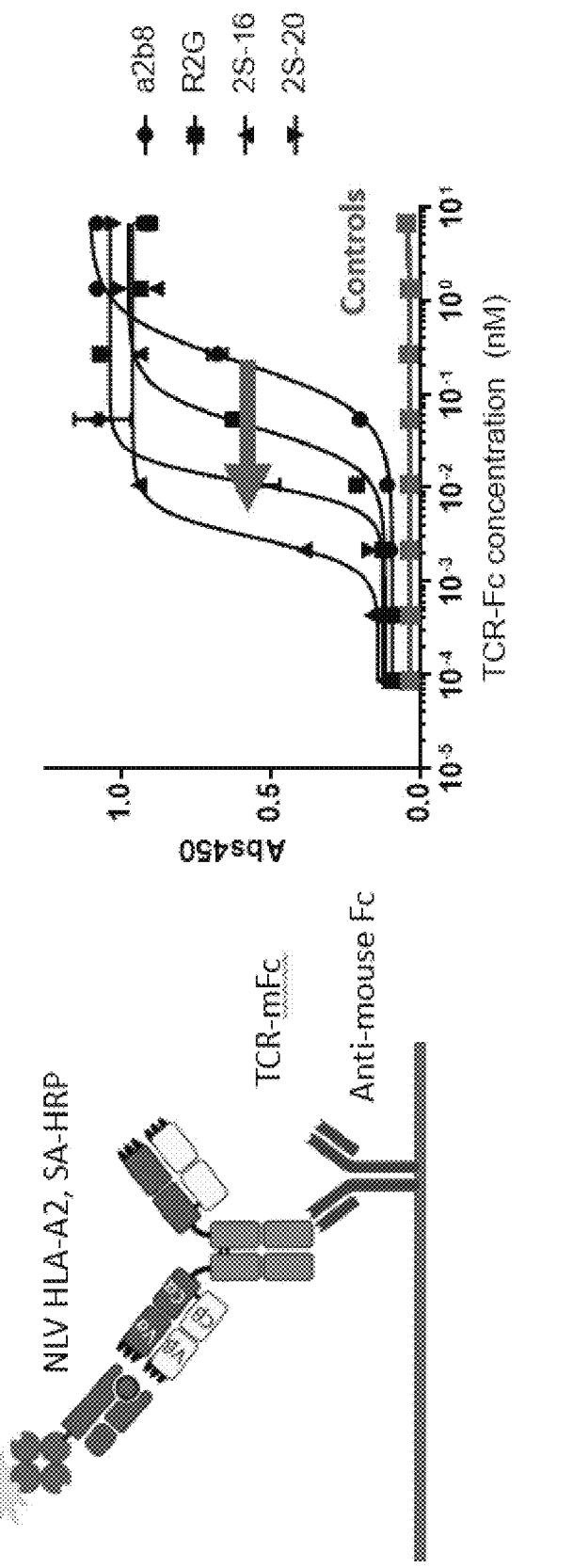

FIG. 16A-C: Selected variants show excellent expression characteristics and improved pp65/A2 affinity. Selected TCR variants were expressed in CHO cells as TCR-mouse Fc fusion proteins and purified by protein A chromatography. A, SDS-PAGE gel shows protein purity and mono-dispersity, as well as the expected molecular weights under non-reducing (~150 kDa) and reducing conditions (~50 and 25 kDa bands). B, Protein monodispersity was evaluated using analytical size exclusion chromatography with an S200 Superdex column on an Akta FPLC (30 g each protein was injected, except 100 g was used for the α2β8 TCR-mFc). C, An ELISA in which dilutions of the purified TCR-Fc proteins were used for coating, followed by mono-meric pp65/A2 and streptavidin-HRP for detection shows that selected variants exhibit affinity increases, as measured by the TCR-Fc concentration resulting in 50% of the maxi-mum ELISA signal. Controls include uncoated wells and an irrelevant peptide/A2 complex.

Figure 17:
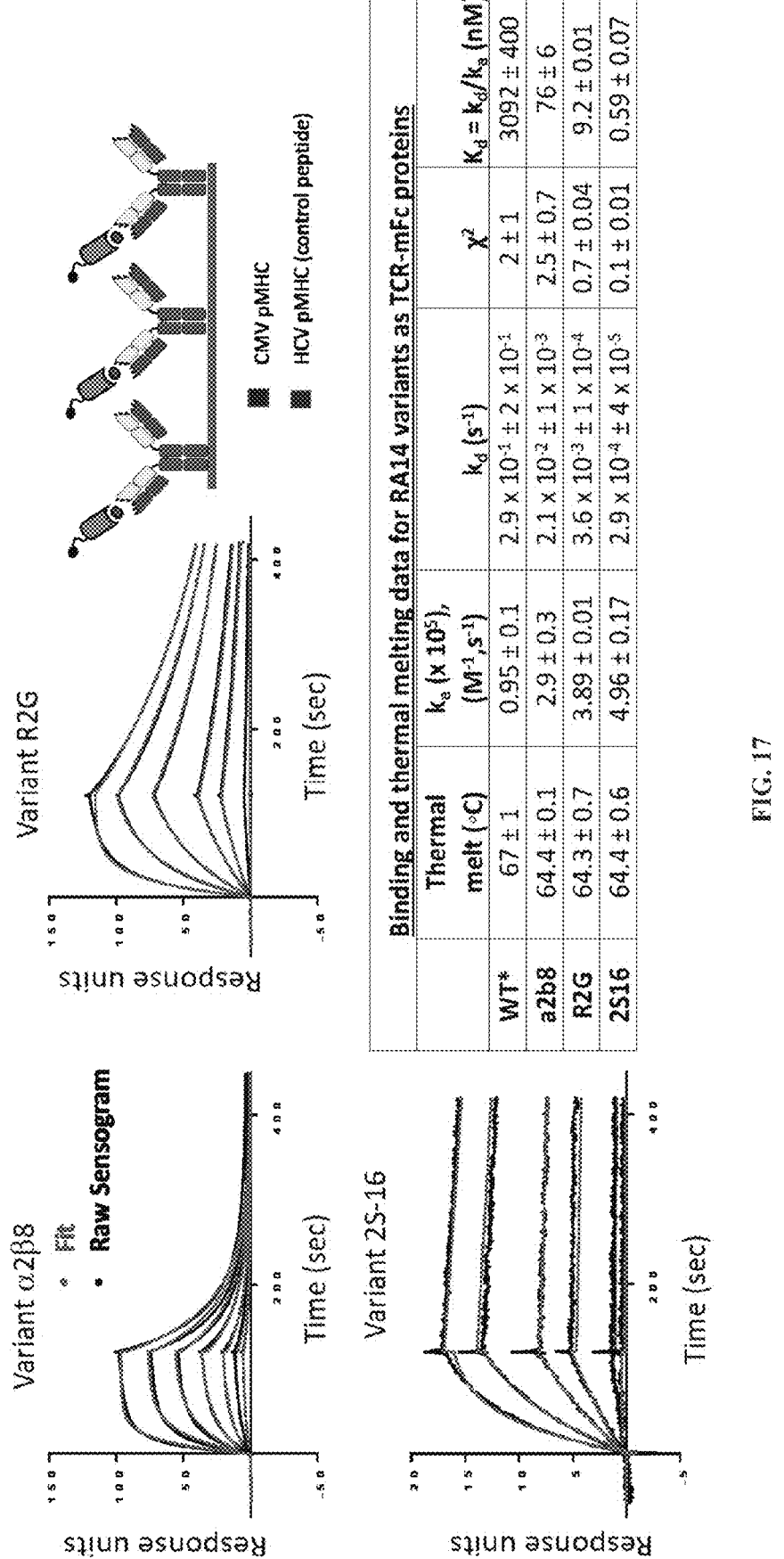

FIG. 17: Binding kinetics for selected TCR-Fc variants with the pp65/A2 ligand. SEC-purified TCR-Fc was immo-bilized on CM5 chips at ~500 RU. The monomeric pp65/A2 was injected at concentrations ranging from 0.1-500 nM. The control pMHC complex, the GIL peptide from HCV complexed with the A2 MHC, was injected at the highest concentration, 500 nM. Binding kinetics were determined using a 1:1 Langmuir fit. Experiments performed on a BIAcore X100 SPR instrument.

Figure 18:
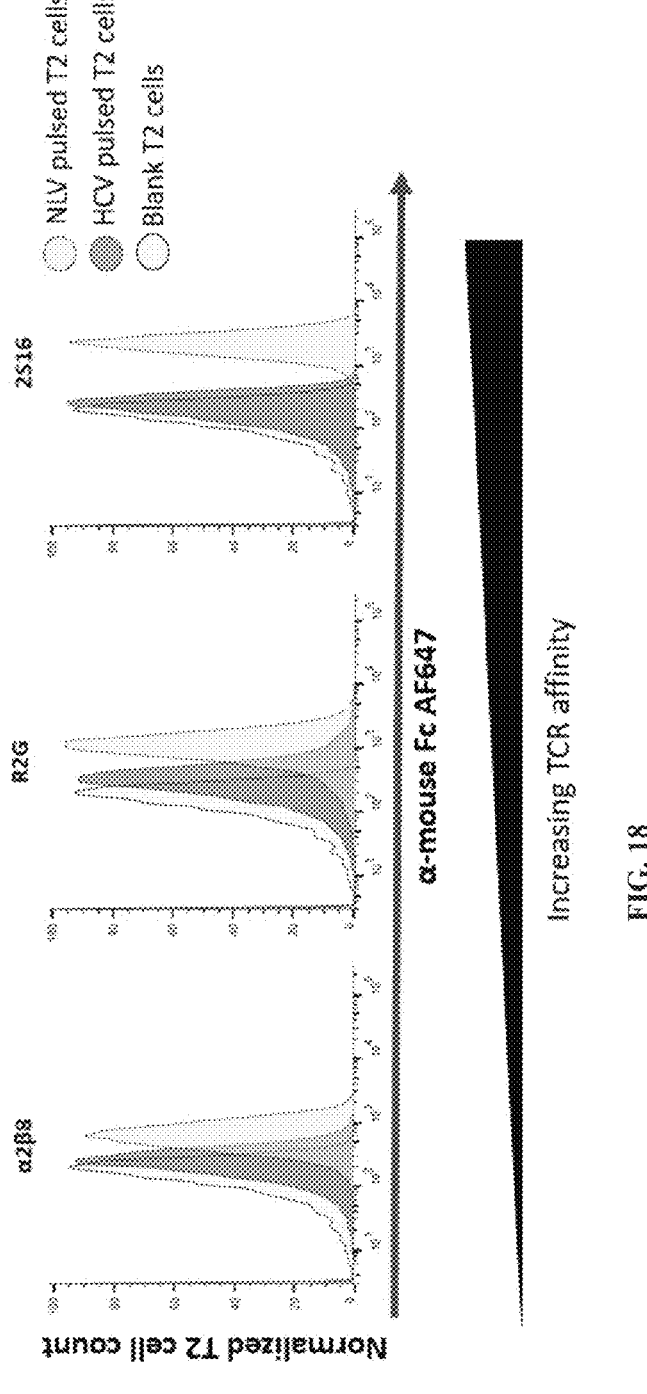

FIG. 18: Increased TCR affinity results in increased selectivity of binding to pp65 peptide-pulsed antigen pre-senting cells. Selected TCR variants were expressed in CHO cells as TCR-mouse Fc fusion proteins and purified. These were then used to stain human T2 antigen presenting cells which were pulsed with 100 μM pp65 or control HCV peptide and detected with anti-mouse Fc (F(ab)2-AF647 in the presence of Fc block. The observed population mean fluorescence shift correlates with the TCR affinity.

FIG. 19: Engineered TCR sequences activate T cells in the presence of pp65-peptide-pulsed antigen presenting cells. Selected RA14 TCR sequences were expressed with the five described N-to-Q substitutions that eliminate N-linked gly-cosylation sites on the surface of human Jurkat cells as well as native TCR transmembrane and intracellular sequences. These cells were co-cultured w/human T2 antigen present-ing cells pulsed with NLV (pp65) or KLV (control flu) peptides and the resulting T cell activation monitored by CD69 upregulation & flow cytometry.

FIG. 20A-D: The vFcγRs gp34 and tgp68 were expressed in CHO cells and purified. Receptors were cloned from the AD169/GFP bacterial artificial chromosomal DNA, appended with strep and FLAG tags, and expressed tran-siently in CHO cells. A, After purification on a streptactin column, 4 g of reduced (R) and non-reduced (NR) protein was analyzed by SDS-PAGE. Each protein appeared as a single band and at approximately the correct size (66 kDa for glycosylated tgp68 and 68 kDa for glycosylated gp34). B and C, Protein monodispersity was assessed with size exclu-sion chromatography (SEC) using a Superdex200 column on an Akta FPLC and D, observed molecular weights for these glycosylated proteins estimated using the elution vol-umes of proteins with known sizes on the same S200 column.

FIG. 21A-C: Competition ELISAs indicate that gp34 and FcγRIIIA have overlapping epitopes and gp68 and FcRn have overlapping epitopes. A) Human IgG1 (purple shape was coated on high-binding plates. Receptor alone or mixed with competitor was added to plates and detected with anti-FLAG-HRP. B) Human IgG1 was coated on ELISA plates, and then a dilution series of FLAG-tagged FcRn was added and detected with anti-FLAG-HRP (negative control). Competition was performed by mixing each competitor (gp34, tgp68, or excess IgG1) at 0.5 μg/ml (6.7 nM) with FcRn prior to addition to the plate. C) Human IgG1 was coated on ELISA plates, and then a dilution series of FLAG-tagged FcγRIIIA was added and detected with anti-FLAG-HRP (negative control). Competition was performed by mixing each competitor (gp34, tgp68, or excess IgG1) at 0.2 g/ml (0.3 nM) with FcγRIIIA prior to addition to the plate.

FIG. 22A-B: Receptor binding data for the gp68 Fe escape variant YTE. The YTE antibody changes (M252Y, S254T, T256E (Dall'Acqua et al. 2006) eliminate binding to the gp68 vFc receptor while actually increasing binding to the hist FcRn. Binding demonstrated using flow cytometry with yeast expressing the wild-type or YTE human IgG1 Fc as an Aga-2 fusion protein. Cells were then stained with an anti-human Fc-AF647 to monitor Fc display level and one of the four Fc receptors plus fluorescent detection (FcRn, FcgRIIIa, gp34 or gp68). Note, gp34 and gp68 bind Fc with nanomolar affinities while the host receptors bind with micromolar affinities; FcRn binding was monitored at low pH to increase binding affinity. YTE is known to slightly reduce binding to FcgRIIIa.

FIG. 23A-B: Antibody Fe sequences that lack of binding to gp34 but retain binding to FcRn. A, sequence alignment from Kabat residues 220 to 353 of human IgG1. B, list of selected amino acid changes using Kabat numbering scheme.

Figure 24:
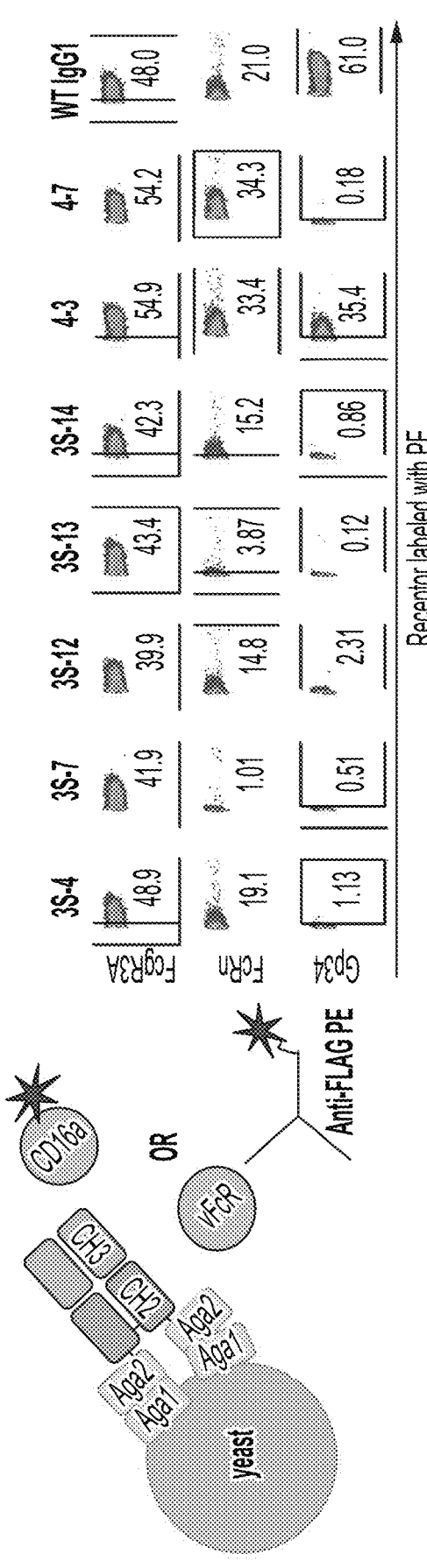

FIG. 24: Receptor binding data for selected gp34 Fe escape variants. Variants selected by yeast display were analyzed for binding to gp34, human FcRn and human FcgRIIIa by flow cytometry. Yeast expressing the wild-type or selected human IgG1 Fc variants as an Aga-2 fusion protein were stained with each Fc receptor individually (FcRn, FcgRIIIa, gp34) followed by fluorescent detection. FcRn binding was monitored at low pH to increase binding affinity.

FIG. 25A-C: Expression of the OT-II TCR-Fc in CHO cells followed by protein A chromatography purification. A, SDS-PAGE gel, B, size exclusion chromatography and C, ELISA with purified TCR-Fc protein.

FIG. 26A-C: DO11.10 and variants bind KJ1-26 as scTCR-Fc fusion proteins. Proteins were produced in CHO cells as scTCR-Fc fusion proteins using the Vβ-linker-Vα format and purified using protein A chromatography. A, Protein purity and size was assessed by SDS-PAGE under reducing and non-reducing conditions. B, Analytical SEC was used to assess the polydispersity of the purified protein preparations following seven days storage at 4° C. using an S200 column. Shown are traces for DO11-Fc, 176-Fc, 817-Fc and the control 172.10-Fc. C, Binding to the KJ1-26 clonotypic antibody was assessed by ELISA. Purified scTCR-Fc proteins were titrated on KJ1-26 coated and blocked. Shown are DO11-Fc (circles), 176-Fc (squares), 817-Fc (triangles) and the 172.10-Fc control (inverted tri-angles). Shown are the mean and std dev for duplicates; data are representative of three replicate experiments.

FIG. 27A-C: DO11 and variants detect OVA/I-Ad on A20 antigen presenting cells as scTCR-Fc fusion proteins. A, Murine A20 cells were pulsed overnight with 100 μM OVA323-339 peptide or an equivalent volume of DMSO before staining with 0.5 μM of each TCR-Fc fusion variant and detection with anti-human Fc (AF-647) in the presence of Fc block. Shown are histograms resulting from staining with only the secondary antibody; the 172.10-Fc control, DO11-Fc, 176-Fc and 817-Fc. For all conditions, back-ground staining to A20 cells without peptide pulsing are shown (hollow traces). B, The scTCR-Fc dissociation rates from peptide-pulsed cells were measured using flow cytometry. Cells were stained as above, with 10 μg/ml (KJ1-26 added at time zero to block scTCR rebinding. Temporal data were fit to a single exponential decay to calculate cellular off-rates. C, Tabulated off-rate data and half-life data (t1/2=1n2/koff). Shown are the mean and std dev of replicates. Data are representative of 2-3 independent experiments. No comparisons were statistically significantly different by ANOVA.

DESCRIPTION OF ILLUSTRATIVE EMBODIMENTS

While antibodies recognize secreted and surface-bound proteins, T-cell receptors (TCRs) recognize otherwise inaccessible disease-associated intracellular proteins when presented as a processed, nonameric peptide bound to a major histocompatibility complex (pMHC). TCRs have been primarily explored for cancer applications but could target infectious diseases, such as cytomegalovirus (CMV). However, TCRs are much more difficult to express and engineer than antibodies, and advanced methods are needed to enable their widespread use. Engineered TCRs can be used in adoptive T-cell therapies to re-direct patient T cells to recognize a chosen target, while soluble TCRs can be used as antibody-like reagents to bind specific peptide MHC complexes presented on a cell surface.

Provided herein are antibody-like reagents that specifically recognize CMV-infected cells by virtue of the immunodominant pp65 peptide in complex. These reagents have an increased affinity relative to a native TCR (from ~30 micromolar to 50 nanomolar) and a novel TCR-Fc format providing for very high expression levels. These reagents have multiple potential applications. For example, therapeutic uses of the engineered TCR include targeting brain cancers (e.g., glioblastomas) where latent CMV is reactivated. Another use includes delivering the NLV peptide to cancer cells in a patient and then administering a therapeutic engineered TCR to the patient to detect the efficiency of NLV peptide delivery/display as well as re-target CMV-specific T cells. A therapeutic engineered TCR may be a bispecific molecule that binds to both NLV/A2 and to CD3, thereby re-targeting T cells to destroy virus-infected cells. In addition, the engineered TCRs may be used to monitor NLV/A2 expression on host cells, either in vitro or in vivo. This use includes monitoring NLV presentation after vaccination with novel CMV vaccines as well as detecting active infection in organ transplant recipients.

I. The Present Embodiments

Soluble TCRs have considerable potential as therapeutics and reagents to monitor disease progression or vaccine efficacy. In particular, T cells recognizing the immunodominant NLV peptide from CMV are sufficient to maintain clinical latency, suggesting NLV is a useful marker to monitor disease or vaccination status. Here, variants of the human CMV-specific TCR RA14 with nanomolar affinity for the cognate NLV/A2 complex were identified by selection on the CHO cell surface. These variants retained peptide selectivity and activity when expressed on the surface of human Jurkat T cells. Moreover, high level production of homogeneous protein was observed when the TCR domains were fused to an antibody Fc domain to create an antibody-like targeting molecule. This construct specifically detected NLV/A2 complexes on the surface of human antigen presenting cells at low display levels and provides proof-of-concept for a new TCR engineering strategy.

16

Figures 1A, 1B, 1C:
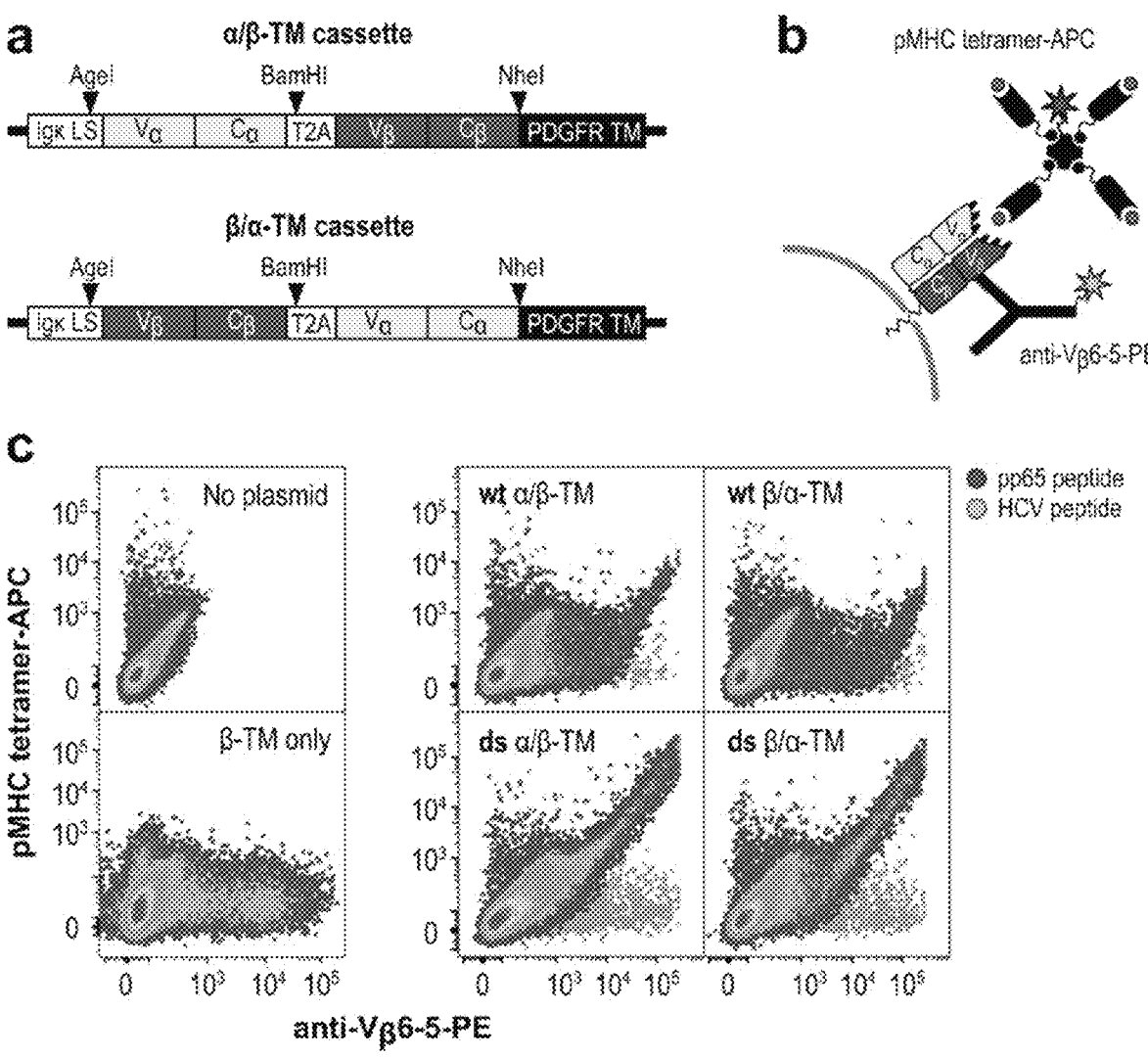
FIGS. 1A-1C: The NLV-specific human TCR RA14 displays on the surface of CHO-K1 cells.

Since TCR engineering continues to be challenging with phage and yeast display platforms, it was reasoned that TCR expression on the near-native eukaryotic membrane might offer a more straightforward approach. High levels of active TCR were able to be displayed using a PDGFR transmembrane domain, modified only by inclusion of a previously described non-native disulfide bond between the TCR constant domains (Boulter et al., 2003). Specific pMHC binding activity was measured as the ratio of NLV/A2 tetramer binding to TCR display level, with the wildtype RA14 showing a clear population of cells with high specific activity (FIG. 1C). In contrast, phage or yeast display of scTCRs or paired TCR extracellular domains are restricted to well-behaved germline segments (e.g., mouse TRBV13 and human TRAV12) (Li et al., 2004; Maynard et al., 2005) or require considerable engineering to achieve display of active protein, including identification of specific mutations and co-expression of chaperones (Maynard et al., 2005; Gunnarsen et al., 2013). Even so, variants with partially suppressed stop codons have been isolated, suggesting the proteins retain toxicity (Li et al., 2005).

Eukaryotic display has been explored previously for TCR engineering. Importantly, these prior reports used completely native TCRs, with TCR extracellular, transmembrane, and intracellular signaling domains expressed on T cells (Kessels et al., 2000; Chervin et al., 2008; Malecek et al., 2013). In contrast, use of the PDGFR transmembrane domain fused to just one TCR chain eliminated TCR dependence on CD3 co-expression, provided selection pressure for proper TCR assembly, and allowed the use of CHO cells. An episomal plasmid allowed the more cumbersome retroviral transfection system used in the earlier studies to be avoided while maintaining TCR expression for ~2 months, and while inclusion of a 2A peptide ensured equimolar expression of the alpha and beta chains. Since most therapeutic proteins are produced in CHO cells, this system allows for selection of TCRs with characteristics that are expected to be more predictive of the soluble protein when expressed in CHO cells. Importantly, this includes glycosylation sites that may affect ligand binding (Nguyen et al., 2018) or TCR assembly (FIGS. 7A-D).

Eukaryotic display platforms have constrained library sizes due to their lower transfection efficiencies as compared to bacteria and yeast. Despite this, the three previously reported eukaryotic TCR libraries all produced interesting clones. Kessels et al. (2000) randomized seven codons in CDR30 of the flu-specific F5 TCR to generate a library of ~3×10⁴ unique clones. After four rounds of flow cytometric sorting with labelled tetramer, they isolated a variant with physiologic affinity and newly acquired binding to an altered peptide ligand containing two residue changes. Similarly, Chervin et al. (2008) altered five codons in the mouse 2C TCR CDR3α to yield a library of ~10³-10⁴ clones. After two rounds of flow cytometry, they isolated variant m100 with an estimated 1,900 nM affinity, representing a 4-to-15-fold improvement over the wild-type TCR. By contrast, an even higher affinity 2C variant, m33 with a ~32 nM affinity, was isolated from a similarly designed, but larger (5×10⁵), yeast display library (Holler et al., 2003).

The libraries provided here, while still of modest size (4×10⁵ for CDR3α and 1×10⁶ for CDR3β), were larger than those previously reported for eukaryotic TCR display systems. Taking into account a ~50% transfection efficiency, cell death, and dilution with blank plasmid, a single T-150 flask with adherent CHO cells can reasonably yield five-fold coverage of a 5×10⁵ member library. With shaker flasks and suspension cells to facilitate scale up, a library of 10⁷ should be achievable. While this remains smaller than many bacterial or yeast-display libraries, the stereotypical TCR-pMHC binding interaction in which the two CDR3 loops dominate peptide binding (Rossjohn et al., 2015), can be exploited to generate targeted mutagenesis libraries rich in higher affinity variants.

From these libraries, variants with increased on-rate and decreased off-rate were isolated (Table 2). Importantly, the changes in specific tetramer binding observed during library screening anticipated the affinity improvements measured by SPR (FIGS. 3C-D). When the two selected chains were combined to create variant αV2.βV8, the benefits were roughly additive, resulting in an overall ~60-fold improved NLV/A2 affinity as compared with the wild-type RA14. Specificity for the NLV peptide was retained, as binding to a control HCV/A2 complex was not detected even at 500 nM (Table 2). Analysis of previously engineered TCRs indicates that affinity improvements are typically due to large decreases in off-rate and small increases in on-rate, as was observed for RA14. Structurally, this has been mediated by increases in overall shape complementarity and formation of new contacts between the TCR and peptide residues, which retain the native TCR/pMHC binding angle (Sami et al., 2007; Cole et al., 2013). For example, four residue changes in CDR3β of the A6 TCR formed 26 new peptide contacts that were sufficient to increase affinity for the tax/A2 complex from 3.2 µM to 4 nM (Cole et al., 2013).

As expected based on the significantly lower affinities present in endogenous TCR repertoires, the sequences identified here have not been reported in human sequencing studies of NLV/A2-binding T cells (Trautmann et al., 2005; Wang et al., 2012). In CDR3α, two residues from the $x_n$GNQF motif were altered: the conserved glycine was not always observed in position α:109, while the enhanced on-rate αV2 variant replaced the canonical α:Q115 with a histidine. Regardless, these modest sequence and affinity changes support the idea that this common public CDR3α sequence is relatively optimized for NLV/A2 binding. Furthermore, the structure of the related TCR C7 (CDR3α sequence: ITGNQF (SEQ ID NO:73)) in complex with NLV/A2 demonstrates the ability of this CDR3α to preserve a similar peptide-binding interaction while making small adjustments to accommodate a different CDR3β (Yang et al., 2015). Changes to the CDR3β motif $Sx_nTGx_nYGY$ were more dramatic despite revealing Vβ:G111 to be absolutely conserved in all sequences recovered in this work; notably, residue Vβ:G111 was anticipated as crucial for binding from the initial analysis of the RA14-NLV/A2 crystal structure (Gras et al., 2009). Among other CDR30 residues, the motif residue Vβ:G115 was not always retained, but was preferentially replaced with hydrophobic residues, with five of ten clones using leucine. The other randomized CDR30 positions all showed evidence of structural plasticity, with the slow off-rate βV8 variant preferring hydrophobic residues in all three modified positions (Table 1).

High-level expression of soluble TCR proteins continues to present challenges due to their low expression levels and weak heterodimerization properties. Common expression strategies include generation of single-chain TCRs, which typically requires identification of specific residue changes that support folding and expression in this format (Shusta et al., 2000; Aggen et al., 2011; Wulfing & Pluckthun, 1994); refolding of intact extracellular domains (van Bozel et al., 2009), often with a modified disulfide bond supporting constant domain heterodimerization introduced at residues Cα:T84C and Cβ:S79C (Boulter et al., 2003); and TCR-antibody chimeras expressed in eukaryotes. For this latter approach, a variety of designs have been evaluated, including single-chain TCRs fused to a constant beta domain and then antibody heavy chain domains 1-3 (Mosquera et al., 2005), complete TCR extracellular domains appended with constant kappa domains (Gregoire et al., 1991) or an intact antibody fused to the TCR C-terminus (Lunde et al., 2010; Lebowitz et al., 1999) and simply replacing the antibody variable regions with TCR variable regions (Lunde et al., 2010).

The present approach was to use the simplest antibody-like design that supported expression of active TCR material. This strategy was guided by the desire to employ established antibody purification processes and minimize the risks of proteolysis and immunogenicity in the resulting protein. After evaluation of several designs, substitution of the antibody Fab domains with the TCR extracellular domains emerged as the best approach. Specifically, the extracellular TCR α chain was fused to the antibody Fc domain with the R chain expressed in trans. Subsequent replacement of the human Fc for the corresponding mouse Fc domains allowed for detection of NLV/A2 complexes on peptide-pulsed antigen presenting cells (FIG. 9B).

Additional modifications were introduced to support proper assembly of the TCR-Fc chimera. In addition to the previously described engineered disulfide bond between the TCR constant domains (Boulter et al., 2003), the human IgG1 upper and core hinge region introduced a second disulfide bond joining the TCR constant domains and two disulfide bonds stabilizing the Fc homodimer, while the free cysteine at position 85.1 was replaced with an alanine. Finally, two predicted N-linked glycosylation sites in the variable domains and three in the human constant TCR domains were eliminated by N-to-Q substitutions. Together, this allowed for production of 0.75-1 mg purified TCR2dsΔgly-huFc protein from 50 mL media, matching typical antibody yields in the lab scale transient CHO cell expression system. This strategy has yielded similar production levels for three additional TCRs.

Prior attempts to replace the antibody Fab with the TCR extracellular domains were less successful (Lunde et al., 2010; Ozawa et al., 2012); but these in general did not include the antibody upper hinge region to provide an additional di-sulfide bond stabilizing the alpha and beta chains and did not remove glycosylation sites then thought to increase protein solubility. Although endogenous TCRs are highly glycosylated on the T-cell surface, analysis of TCR affinity and structure are typically performed on bacterially expressed TCR protein, which is aglycosylated. The expression system developed here allows for direct comparison of identical TCR proteins with and without glycosylation at specific sites. Removal of predicted N-linked glycosylation sites dramatically increased protein homogeneity as measured by size-exclusion chromatography and SDS-PAGE (FIG. 5A), with no negative impact on yield or thermal stability. Further investigation could provide insights into the impact of glycosylation on TCR function, as removal of glycosylation sites has been shown to increase the functional avidity of TCRs expressed on T cells (Kuball et al., 2009).

The ability of TCRs to detect pMHC on the target cell surface is inextricably linked to not just the TCR-pMHC affinity but also the peptide display level and pMHC clustering on the cell surface. Peptide display level in turn reflects several factors, including antigen expression level, proteolysis sensitivity, and peptide-MHC affinity. For TCRs expressed with their native signaling machinery on T cells, an affinity of 1-5 µM seems sufficient to confer maximal signaling responses (Irving et al., 2012) while retaining the ability to respond to as few as 1-10 pMHC complexes per cell (Kageyama et al., 1995; Sykulev et al., 1996). For soluble TCRs, which lack the elaborate array of coreceptors that support cellular TCR-pMHC recognition, high affinity is crucial to allow detection of low levels of target pMHC antigens. In this work, the ability of RA14 TCR variants to detect NLV/A2 correlated strongly with affinity for human T2 cells pulsed with 100 µM NLV peptide (FIG. 9B). A subsequent peptide dosing experiment demonstrated that the αV2.βV8 variant could detect NLV/A2 complexes after pulsing T2 cells with as little as 0.5 µM peptide (FIG. 9C).

The sensitivity exhibited by αV2.βV8 is relevant for detection in clinical settings. The NLV peptide was previously reported to present ~100 molecules/cell when primary human fibroblasts were infected with an AD169 strain that retains the ability to suppress MHC display (Makler et al., 2010). A bivalent TCR-like antibody with a 300 nM affinity was previously shown to detect the NLV/A2 complex after infection of primary human fibroblasts with CMV, but has not been further developed (Makler et al., 2010). The higher 50 nM affinity of the present engineered TCR suggests that the αV2.βV8 clone could be used to track pMHC display and demonstrates the feasibility of the present TCR engineering approach. Moreover, the flow cytometer sensitivity can be increased with an enzymatic amplification step (Anikeeva et al., 2009) or a single molecule fluorescence assay (Bossi et al., 2013).

There is considerable interest in using TCRs to monitor the presence of disease-related peptides and a need to detect the NLV/A2 complex to support CMV diagnostics and therapeutics development. High-affinity, soluble TCRs directed at cancer antigens are currently under evaluation in the clinic as part of a bispecific molecule (Bossi et al., 2014). As compared to cancer antigens, infectious disease-associated antigens are more likely to be unique to diseased tissue, thereby reducing the risks of toxicity.

II. Engineered NLV/A2-specific TCRs

In some embodiments, provided herein are engineered antigen receptors (e.g., TCRs or CARs) having antigenic specificity for NLV/A2. The engineered antigen receptors may comprise an alpha chain CDR3 having at least 90%, 91%, 92%, 93%, 94%, 95%, 96%, 97%, 98%, 99%, or 100% sequence identity to any one of SEQ ID NOs: 1-7 (or a sequence from Table 1C) and/or a beta chain CDR3 having at least 90%, 91%, 92%, 93%, 94%, 95%, 96%, 97%, 98%, 99%, or 100% sequence identity to any one of SEQ ID NOs: 8-17 (or a sequence from Table 1D). The engineered antigen receptors may comprise an alpha chain with at least 90%, 91%, 92%, 93%, 94%, 95%, 96%, 97%, 98%, 99%, or 100% identity or similarity to any one of SEQ ID NOs: 18-24 (or a sequence from Table 1C) and/or a beta chain with at least 90%, 91%, 92%, 93%, 94%, 95%, 96%, 97%, 98%, 99%, or 100% identity or similarity to any one of SEQ ID NOs: 25-34 (or a sequence from Table 1D). Also provided herein are polynucleotides encoding the alpha chain and/or beta chain of the NLV/A2-specific antigen receptors provided herein. As used herein numbering of amino acids relative to TCR sequences uses the imgt numbering system (see, the world wide web at imgt.org/IMGTrepertoire/Proteins/proteinDisplays.php?species=human&latin=Homo%20sapien s&group=TRAV, incorporated herein by reference).

Exemplary antigen receptors, including CARs and recombinant TCRs, as well as methods for engineering and introducing the receptors into cells, include those described, for example, in International Patent Application Publication Nos. WO2000/14257, WO2013/126726, WO2012/129514, WO2014/031687, WO2013/166321, WO2013/071154, WO2013/123061; U.S. Patent Application Publication Nos. US2002/0131960, US2013/0287748, US2013/0149337; U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118; and European Patent Application No. EP2537416. In some aspects, the genetically engineered antigen receptors include a CAR as described in U.S. Pat. No. 7,446,190, and those described in International Patent Application Publication No. WO2014/055668.

In some embodiments, the engineered antigen receptors include recombinant T cell receptors (TCRs). A "T cell receptor" or "TCR" refers to a molecule that contains a variable a and R chains (also known as TCRα and TCRβ, respectively) and that is capable of specifically binding to an antigen peptide bound to an MHC receptor. The TCRs may comprise an alpha chain CDR3 having at least 90%, 91%, 92%, 93%, 94%, 95%, 96%, 97%, 98%, 99%, or 100% sequence identity to any one of SEQ ID NOs: 1-7 (or a sequence from Table 1C) and/or a beta chain CDR3 having at least 90%, 91%, 92%, 93%, 94%, 95%, 96%, 97%, 98%, 99%, or 100% sequence identity to any one of SEQ ID NOs: 8-17 (or a sequence from Table 1D). The TCRs may comprise an alpha chain with at least 90%, 91%, 92%, 93%, 94%, 95%, 96%, 97%, 98%, 99%, or 100% identity or similarity to any one of SEQ ID NOs: 18-24 (or a sequence from Table 1C) and/or a beta chain with at least 90%, 91%, 92%, 93%, 94%, 95%, 96%, 97%, 98%, 99%, or 100% identity or similarity to any one of SEQ ID NOs: 25-34 (or a sequence from Table 1D).

In some embodiments, a TCR also can contain a constant domain, a transmembrane domain, and/or a short cytoplasmic tail. For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments. The term also encompasses intact or full-length TCRs.

For purposes herein, reference to a TCR includes any TCR or functional fragment, such as an antigen-binding portion of a TCR that binds to a specific antigenic peptide bound in an MHC molecule, i.e., MHC-peptide complex. An "antigen-binding portion" or "antigen-binding fragment" of a TCR, which can be used interchangeably, refers to a molecule that lacks a portion of the structural domains of a TCR, but that binds the antigen (e.g., MHC-peptide complex) to which the full TCR binds. In some cases, an antigen-binding portion contains the variable domains of a TCR, such as variable a chain and variable R chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule. Typically, like immunoglobulins, the CDRs are separated by framework regions (FRs). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., Vα or Vβ; typically amino acids 1 to 116 based on Kabat numbering (Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or Cα, typically amino acids 117 to 259 based on Kabat, β-chain constant domain or Cβ, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domains of the TCR contain short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

In some embodiments, the TCR may be a heterodimer of two chains α and β or it may be a single-chain TCR construct. In some embodiments, the TCR is a heterodimer containing two separate chains (α and β chains) that are linked, such as by a disulfide bond or disulfide bonds. In some embodiments, a TCR for a target antigen (e.g., NLV/A2) is identified and introduced into the cells. In some embodiments, a nucleic acid encoding the TCR can be obtained from a variety of sources. In some embodiments, the TCR is obtained from a biological source, such as from cells such as from a T-cell hybridomas. In some embodiments, the T cells can be a cultured T-cell hybridoma or clone.

TABLE 1A

CDR3 sequences for α chain variants.

| Variant | SEQ ID NO: | CDR3α |
|---------|-----------|--------|
| α1 | 1 | CARNSGNP |
| α2 | 2 | CARNYGNH |
| α3 | 3 | CAPNYINT |
| α4 | 4 | CARSFGNP |

TABLE 1A-continued

CDR3 sequences for α chain variants.

| Variant | SEQ ID NO: | CDR3α |
|---------|-----------|--------|
| α5 | 5 | CARSVGNS |
| α6 | 6 | CARLLANL |
| α7 | 7 | CARGSWNQ |
| 2S-16 | 60 | CARNYGNQ |
| 2S-20 | 61 | CARNYGNP |
| WT | 39 | CARNTGNQ |

TABLE 1A-2

CDR1 sequences for α chain variants.

| Variant | SEQ ID NO: | CDR1α |
|---------|-----------|--------|
| a2b8 | 64 | SNFYA |
| R2G | 65 | LDFWA |
| 2S-16 | 66 | SNFWA |
| 2S-20 | 66 | SNFWA |
| WT | 64 | SNFYA |

TABLE 1B

CDR3 sequences for β chain variants.

| Variant | SEQ ID NO: | CDR3β |
|---------|-----------|--------|
| β1 | 8 | AAAPVTGGVYLYT |
| β2 | 9 | ASSRVTGGVYLYT |
| β3 | 10 | ASSPITGSTYIYT |
| β4 | 11 | ASSPITGAPYLYT |
| β5 | 12 | ASSPVTGSSYGYT |
| β6 | 13 | ASSWITGSIYTYT |
| β7 | 14 | ASSPVTGSSYWYT |
| β8 | 15 | ASSLVTGGVYLYT |
| β9 | 16 | ASSLVTGIPYLYT |
| β10 | 17 | ASSRVTGSVYGYT |
| 2S-16 | 62 | ASSLVTGSVYLYT |
| 2S-20 | 63 | ASSWVTGGVYLGT |
| WT | 40 | ASSPVTGGIYGYT |

TABLE 1C

Protein sequences for α chain variable regions. Underlined text indi-
cates the CDR region;
gray text indicates N-to-Q changes introduced for deglycosylation; gray text in the CDRs
indicates a change in the CDR sequence selected during library sorting and associated
with increased affinity.

| Variant | SEQ ID NO: | Variable domain alpha sequence |
|---|---|---|
| RA14 WT | 18 | ILNVEQSPQSLHVQEGDSTNFTCSFPSSNFYALHWYRWETAKSPEALFVMTLNGDEKKKGRISATLNTKEG YSYLYIKGSQPEDSATYLCARNTGNQFYFGTGTSLTVIP |
| α1 | 19 | ILNVEQSPQSLHVQEGDSTQFTCSFPSSNFYALHWYRWETAKSPEALFVMTLNGDEKKKGRISATLNTKEG YSYLYIKGSQPEDSATYLCARNGGNPFYFGTGTSLTVIP |
| α2 | 20 | ILNVEQSPQSLHVQEGDSTQFTCSFPSSNFYALHWYRWETAKSPEALFVMTLNGDEKKKGRISATLNTKEG YSYLYIKGSQPEDSATYLCARNVGNLFYFGTGTSLTVIP |
| α3 | 21 | ILNVEQSPQSLHVQEGDSTQFTCSFPSSNFYALHWYRWETAKSPEALFVMTLNGDEKKKGRISATLNTKEG YSYLYIKGSQPEDSATYLCARNLINLFYFGTGTSLTVIP |
| α4 | 22 | ILNVEQSPQSLHVQEGDSTQFTCSFPSSNFYALHWYRWETAKSPEALFVMTLNGDEKKKGRISATLNTKEG YSYLYIKGSQPEDSATYLCARSIGNPFYFGTGTSLTVIP |
| α5 | 23 | ILNVEQSPQSLHVQEGDSTQFTCSFPSSNFYALHWYRWETAKSPEALFVMTLNGDEKKKGRISATLNTKEG YSYLYIKGSQPEDSATYLCARSVGNLFYFGTGTSLTVIP |
| α6 | 24 | ILNVEQSPQSLHVQEGDSTQFTCSFPSSNFYALHWYRWETAKSPEALFVMTLNGDEKKKGRISATLNTKEG YSYLYIKGSQPEDSATYLCARLLANLFYFGTGTSLTVIP |
| α7 | 25 | ILNVEQSPQSLHVQEGDSTQFTCSFPSSNFYALHWYRWETAKSPEALFVMTLNGDEKKKGRISATLNTKEG YSYLYIKGSQPEDSATYLCARGSNNQFYFGTGTSLTVIP |
| 341 | 26 | ILNVEQSPQSLHVQEGDSTQFTCSFPSSNFYALHWYRWETAKSPEALFVMTLNGDEKKKGRISATLNTKEG YSYLYIKGSQPEDSATYLCARGSNNQFYFGTGTSLTVIP |
| R2G | 74 | ILNVEQSPQSLHVQEGDSTQFTCSFPSLDFWALHWYRWETAKSPEALFVMTLNGDEKKKGRISATLNTKEG YSYLYIKGSQPEDSATYLCARNVGNLFYFGTGTSLTVIP |
| 2S16 | 75 | ILNVEQSPQSLHVQEGDSTQFTCSFPSSNFWALHWYRWETAKSPEALFVMTLNGDEKKKGRISATLNTKEG YSYLYIKGSQPEDSATYLCARNVGNQFYFGTGTSLTVIP |
| 2S20 | 76 | ILNVEQSPQSLHVQEGDSTQFTCSFPSSNFWALHWYRWETAKSPEALFVMTLNGDEKKKGRISATLNTKEG YSYLYIKGSQPEDSATYLCARNVGNPFYFGTGTSLTVIP |

TABLE 1D

Protein sequences for β chain variable regions. Underlined text indicates the CDR region;
gray text indicates N-to-Q changes introduced for deglycosylation; gray text in the CDRs
indicates a change in the CDR sequence selected during library sorting and associated
with increased affinity.

| Variant | SEQ ID NO: | Variable domain beta sequence |
|---|---|---|
| RA14 WT | 27 | AGVTQTPKFQVLKTGQSMTLQCAQDMNHEYMSWYRQDPGMGLRLIHYSVGAGITDQGEVPNGYNVSRSTTEDE PLRLLSAAPSQTSVYFCASSPVTGGIYGYTFGSGTRLTVVE |
| β1 | 28 | AGVTQTPKFQVLKTGQSMTLQCAQDMNHEYMSWYRQDPGMGLRLIHYSVGAGITDQGEVPNGYXVSRSTTEDE PLRLLSAAPSQTSVYFCASSPVTGGYLYTFGSGTRLTVVE |
| β2 | 29 | AGVTQTPKFQVLKTGQSMTLQCAQDMNHEYMSWYRQDPGMGLRLIHYSVGAGITDQGEVPNGYXVSRSTTEDE PLRLLSAAPSQTSVYFCASSXVTGGYLYTFGSGTRLTVVE |
| β3 | 30 | AGVTQTPKFQVLKTGQSMTLQCAQDMNHEYMSWYRQDPGMGLRLIHYSVGAGITDQGEVPNGYXVSRSTTEDE PLRLLSAAPSQTSVYFCASSPITGSYIYTFGSGTRLTVVE |
| β4 | 31 | AGVTQTPKFQVLKTGQSMTLQCAQDMNHEYMSWYRQDPGMGLRLIHYSVGAGITDQGEVPNGYXVSRSTTEDE PLRLLSAAPSQTSVYFCASSPITGAYYLYTFGSGTRLTVVE |
| β5 | 32 | AGVTQTPKFQVLKTGQSMTLQCAQDMNHEYMSWYRQDPGMGLRLIHYSVGAGITDQGEVPNGYXVSRSTTEDE PLRLLSAAPSQTSVYFCASSPVTGSYGYTFGSGTRLTVVE |
| β6 | 33 | AGVTQTPKFQVLKTGQSMTLQCAQDMNHEYMSWYRQDPGMGLRLIHYSVGAGITDQGEVPNGYXVSRSTTEDE PLRLLSAAPSQTSVYFCASSXITGSIYYTFGSGTRLTVVE |

TABLE 1D-continued

Protein sequences for β chain variable regions. Underlined text indicates the CDR region;
gray text indicates N-to-Q changes introduced for deglycosylation; gray text in the CDRs
indicates a change in the CDR sequence selected during library sorting and associated
with increased affinity.

| Variant | SEQ ID NO: | Variable domain beta sequence |
|---|---|---|
| β7 | 34 | AGVTQTPKFQVLKTGQSMTLQCAQD<u>MNHEYMS</u>WYRQDPGMGLRLIHY<u>SVGAGI</u>TDQGEVPNGYQVSRSTTEDE<br>PLRLLSAAPSQTSVYFC<u>ASSPVTGSYYYT</u>FGSGTRLTVVE |
| β8 | 35 | AGVTQTPKFQVLKTGQSMTLQCAQD<u>MNHEYMS</u>WYRQDPGMGLRLIHY<u>SVGAGI</u>TDQGEVPNGYQVSRSTTEDE<br>PLRLLSAAPSQTSVYFC<u>ASSVTGGYYYT</u>FGSGTRLTVVE |
| β9 | 36 | AGVTQTPKFQVLKTGQSMTLQCAQD<u>MNHEYMS</u>WYRQDPGMGLRLIHY<u>SVGAGI</u>TDQGEVPNGYQVSRSTTEDE<br>PLRLLSAAPSQTSVYFC<u>ASSVTGFYYYT</u>FGSGTRLTVVE |
| β10 | 37 | AGVTQTPKFQVLKTGQSMTLQCAQD<u>MNHEYMS</u>WYRQDPGMGLRLIHY<u>SVGAGI</u>TDQGEVPNGYQVSRSTTEDE<br>PLRLLSAAPSQTSVYFC<u>ASSPVTGVYGYT</u>FGSGTRLTVVE |
| 341 | 38 | AGVTQTPKFQVLKTGQSMTLQCAQD<u>MNHEYMS</u>WYRQDPGMGLRLIHY<u>SVGAGI</u>TDQGEVPNGYQVSRSTTEDE<br>PLRLLSAAPSQTSVYFC<u>ASSVTGGYYYT</u>FGSGTRLTVVE |
| 2S16 | 67 | AGVTQTPKFQVLKTGQSMTLQCAQD<u>MNHEYMS</u>WYRQDPGMGLRLIHY<u>SVGAGI</u>TDQGEVPNGYQVSRSTTEDE<br>PLRLLSAAPSQTSVYFC<u>ASSVTGVYYYT</u>FGSGTRLTVVE |
| 2S20 | 68 | AGVTQTPKFQVLKTGQSMTLQCAQD<u>MNHEYMS</u>WYRQDPGMGLRLIHY<u>SVGAGI</u>TDQGEVPNGYQVSRSTTEDE<br>PLRLLSAAPSQTSVYFC<u>ASSVTGGYGYT</u>FGSGTRLTVVE |

A. Soluble TCRs and BiTEs

In addition, the present disclosure provides soluble TCRs. Furthermore, soluble bispecific T cell-engaging molecules (BiTEs) can be generated by linking the engineered NLV/A2-specific TCR to CD3- or CD16-specific Fab fragments or CD3- or CD16-specific single-chain antibodies. These bispecific molecules can bind the cell surface of a CMV-infected cell via their TCR domain binding to the NLV/A2 complex, and the CD3-specific domain would crosslink the TCR. This would result in cellular activation and elimination of the target cell. Thus, these soluble bispecific TCR constructs can be used for treating patients (e.g., transplant patients with active CMV disease or brain cancer patients) directly.

In the context of this application, "solubility" is defined as the ability of the TCR to be purified as a mono-disperse heterodimer in phosphate buffered saline (PBS) (KCl 2.7 mM, $KH_2PO_4$ 1.5 mM, NaCl 137 mM, and $Na_2PO_4$ 8 mM, pH 7.1-7.5. Life Technologies, Gibco BRL) at a concentration of 1 mg/ml and for more than 90% of said TCR to remain as a mono disperse heterodimer after incubation at 25° C. for 1 hour.

The soluble TCR can be fused to an antibody Fc region to create an antibody-TCR chimera. For this, the antibody Fc is fused to the TCR extracellular domains. For example, the TCR α chain may be fused to the Fc and the TCR β chain may be expressed in trans. The chimera may include the antibody hinge region. The antibody Fc may be derived from a mouse or human antibody.

The soluble TCR can be used as a probe for diagnostic evaluation of peptide/MHC in cells, either in vitro or in vivo, or to direct therapeutic molecules to sites of interest in vivo. The soluble TCR molecules also could be labeled with tracers, such as a fluorescent probe or radioactive probe, and then used for diagnostic evaluation of the presentation of peptide/MHC in cells. Furthermore, the soluble TCR molecules could be linked with therapeutic molecules, such as toxin, and then directed to the sites for the treatment of infected cells.

In some embodiments, the present disclosure provides soluble TCRs, such as an engineered NLV/A2-specific TCR provided herein. Soluble TCRs may be used for investigating specific TCR-pMHC interactions or as a diagnostic tool to detect infection or response to vaccination. Soluble TCRs may have applications in staining, for example to stain cells for the presence of a particular peptide antigen presented in the context of the MHC. Similarly, soluble TCRs can be used to deliver a therapeutic agent, for example a cytotoxic compound or an immunostimulating compound, to cells presenting a particular antigen. In some aspects, the TCR is linked to another molecule that delivers a cell in proximity to the tumor. In further aspects, the TCR delivers a toxin, a cytokine, costimulatory ligand, or inhibitor ligand and directs the molecule, cell or compound to the target cells expressing the peptide-MHC.

In some aspects, the present disclosure provides a soluble TCR that comprises (i) all or part of a TCR α chain (e.g., SEQ ID NOs: 18-24), except the transmembrane domain thereof, and (ii) all or part of a TCR β chain (e.g., SEQ ID NOs: 25-34), except the transmembrane domain thereof, wherein (i) and (ii) each comprise a functional variable domain and at least a part of the constant domain of the TCR chain, and are linked by a disulfide bond between constant domain residues that is not present in native TCR.

In some aspects, the soluble TCR comprises a TCR α or δ chain extracellular domain dimerized to a TCR β or δ chain extracellular domain respectively, by means of a pair of C-terminal dimerization peptides, such as leucine zippers (International Patent Publication No. WO 99/60120; U.S. Pat. No. 7,666,604).

A soluble TCR of the present disclosure may be provided in substantially pure form, or as a purified or isolated preparation. For example, it may be provided in a form which is substantially free of other proteins.

The TCR of the present disclosure may alternatively or additionally be associated with (e.g., covalently or otherwise linked to) a therapeutic agent which may be, for example, a toxic moiety for use in cell killing, or an immunostimulating agent such as an interleukin or a cytokine. The present disclosure also provides a method for delivering a therapeutic agent to a target cell, which method comprises contacting potential target cells with a TCR under conditions to allow attachment of the TCR to the target cell, said TCR being specific for the TCR ligand and having the therapeutic agent associated therewith.

In particular, the soluble TCR can be used to deliver therapeutic agents to the location of cells presenting a particular antigen. This would be useful in many situations and, in particular, against certain types of tumors. A therapeutic agent could be delivered such that it would exercise its effect locally but not only on the cell it binds to. Thus, one particular strategy envisages anti-tumor molecules linked to T cell receptors specific for NLV/A2 in order to kill glioblastoma cells.

Many therapeutic agents could be employed for this use, for instance radioactive compounds, enzymes (perforin for example) or chemotherapeutic agents (cisplatin for example). To ensure that toxic effects are exercised in the desired location, the toxin could be inside a liposome linked to streptavidin so that the compound is released slowly. This will prevent damaging effects during the transport in the body and ensure that the toxin has maximum effect after binding of the TCR to the relevant antigen presenting cells.

B. Chimeric Antigen Receptors

In various aspects, the antigen binding region of the TCR may be included in a chimeric antigen receptor (CAR) as the extracellular domain comprising an antigen binding region. The CAR may be transfected into cells (e.g., autologous or allogeneic cells) that may be used in an adoptive cell transfer therapy. In some embodiments, the CAR is humanized to reduce immunogenicity (hCAR).

The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone. In some embodiments, the CAR includes an antigen-binding portion or portions of a TCR.

The arrangement of the antigen-binding domain of a CAR may be multimeric. The hinge portion of the CAR may in some embodiments be shortened or excluded (i.e., generating a CAR that only includes an antigen binding domain, a transmembrane region, and an intracellular signaling domain). In some embodiments, the hinge region may have the first cysteine maintained, or mutated by a proline or a serine substitution, or be truncated up to the first cysteine. In some embodiments, the hinge portion of may comprise or consist of an 8-14 amino acid peptide (e.g., a 12 AA peptide), a portion of CD8a, or the IgG4 Fc. In some embodiments, the antigen binding domain may be suspended from cell surface using a domain that promotes oligomerization, such as CD8 alpha. In some embodiments, the antigen binding domain may be suspended from cell surface using a domain that is recognized by monoclonal antibody (mAb) clone 2D3 (mAb clone 2D3 described, e.g., in Singh et al., 2008).

The endodomain or intracellular signaling domain of a CAR can generally cause or promote the activation of at least one of the normal effector functions of an immune cell comprising the CAR. For example, the endodomain may promote an effector function of a T cell such as, e.g., cytolytic activity or helper activity including the secretion of cytokines. The effector function in a naive, memory, or memory-type T cell may include antigen-dependent proliferation. The terms "intracellular signaling domain" or "endodomain" refers to the portion of a CAR that can transduce the effector function signal and/or direct the cell to perform a specialized function. While usually the entire intracellular signaling domain may be included in a CAR, in some cases a truncated portion of an endodomain may be included. Generally, endodomains include truncated endodomains, wherein the truncated endodomain retains the ability to transduce an effector function signal in a cell.

In some embodiments, an endodomain comprises the zeta chain of the T cell receptor or any of its homologs (e.g., eta, delta, gamma, or epsilon), MB1 chain, B29, Fc RIII, Fc RI, and combinations of signaling molecules, such as CD3ζ and CD28, CD27, 4-1BB, DAP-10, OX40, and combinations thereof, as well as other similar molecules and fragments. Intracellular signaling portions of other members of the families of activating proteins can be used, such as FcγRIII and FcεRI. In some embodiments, an endodomain may comprise the human CD3ζ intracellular domain.

The antigen-specific extracellular domain and the intracellular signaling-domain are preferably linked by a transmembrane domain. Transmembrane domains that may be included in a CAR include, e.g., the human IgG4 Fc hinge and Fc regions, the human CD4 transmembrane domain, the human CD28 transmembrane domain, the transmembrane human CD3ζ domain, or a cysteine mutated human CD3ζ domain, or a transmembrane domain from a human transmembrane signaling protein such as, e.g., the CD16 and CD8 and erythropoietin receptor.

In some embodiments, the endodomain comprises a sequence encoding a costimulatory receptor such as, e.g., a modified CD28 intracellular signaling domain, or a CD28, CD27, OX-40 (CD134), DAP10, or 4-1BB (CD137) costimulatory receptor. In some embodiments, both a primary signal initiated by CD3 ζ, an additional signal provided by a human costimulatory receptor may be included in a CAR to more effectively activate a transformed T cells, which may help improve in vivo persistence and the therapeutic success of the adoptive immunotherapy. As noted in Table 2, the endodomain or intracellular receptor signaling domain may comprise the zeta chain of CD3 alone or in combination with an Fcγ RIII costimulatory signaling domains such as, e.g., CD28, CD27, DAP10, CD137, OX40, CD2, 4-1BB. In some embodiments, the endodomain comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, 1, 2, 3, 4 or more cytoplasmic domains may be included in an endodomain. For example, in some CARs it has been observed that at least two or three signaling domains fused together can result in an additive or synergistic effect.

In some aspects, an isolated nucleic acid segment and expression cassette including DNA sequences that encode a CAR may be generated. A variety of vectors may be used. In some preferred embodiments, the vector may allow for delivery of the DNA encoding a CAR to immune such as T cells. CAR expression may be under the control of regulated eukaryotic promoter such as, e.g., the MNDU3 promoter, CMV promoter, EF1alpha promoter, or Ubiquitin promoter. Also, the vector may contain a selectable marker, if for no other reason, to facilitate their manipulation in vitro. In some embodiments, the CAR can be expressed from mRNA in vitro transcribed from a DNA template.

Chimeric antigen receptor molecules are recombinant and are distinguished by their ability to both bind antigen and transduce activation signals via immunoreceptor activation motifs (ITAM's) present in their cytoplasmic tails. Receptor constructs utilizing an antigen-binding moiety (for example, generated from single chain antibodies (scFv)) afford the additional advantage of being "universal" in that they can bind native antigen on the target cell surface in an HLA-independent fashion. For example, a scFv constructs may be fused to sequences coding for the intracellular portion of the CD3 complex's zeta chain ($\zeta$), the Fc receptor gamma chain, and sky tyrosine kinase.

In some embodiments, a TCR is included in a CAR as the antigen binding domain (e.g., as a scFv region) and the CAR further comprises a hinge region, a transmembrane region, and an endodomain.

TABLE 2

Regions that may be included in an anti-NLV/A2 targeting CAR

| Hinge/Scaffold |
| --- |
| 12 AA (peptide) |
| t-20 AA (peptide) |
| CD8 α |
| IgG4 Fc |
| 2D3 |
| IgG4 Fc Δ EQ (IgG4Fc N40Q) |
| IgG4 Fc Δ Q (IgG4Fc L18E N40Q) |
| t-12AA + t-20AA |
| mKate |
| phiLov |
| dsRed |
| Venus |
| eGFP |
| CH3 HA |
| mTFP-1 |
| CD8 α + t-20AA |
| Double t-20 AA |
| t-20AA + CD8α |
| CD8α + Leucine Zipper Basep1 |
| CD8α + Leucine Zipper Acid1 |
| Transmembrane domain |
| CD28 |
| CD137 (4-1BB) |
| CD8α |
| CD3ζ |
| Endo-domain (signaling domain) |
| CD28 + CD3ζ |
| CD28 + CD27 + CD3ζ |
| CD28 + OX40 + CD3ζ |
| CD28 + 4-1BB + CD3ζ |
| CD28 + CD27 + OX40 + CD3ζ |
| CD28 + 4-1BB + CD27 + CD3ζ |
| CD28 + 4-1BB + OX40 + CD3ζ |
| 4-1BB + CD3ζ |
| 4-1BB + OX40 + CD3ζ |
| 4-1BB + CD27 + CD3ζ |
| CD27 + CD3ζ |
| CD27 + OX 40 + CD3ζ |
| CD28Δ + CD3ζ |
| CD28Δ + CD27 + CD3ζ |
| CD28Δ + OX40 + CD3ζ |
| CD28Δ + 4-1BB + CD3ζ |
| CD28Δ + 4-1BB + OX40 + CD3ζ |
| CD28Δ + CD27 + OX40 + CD3ζ |
| CD28Δ + 4-1BB + CD27 + CD3ζ |
| 4-1BB + ICOS + CD3ζ |
| CD28 + ICOS + CD3ζ |
| ICOS + CD3ζ |
| CD3ζ |
| CD28 only |

ζ-zeta; Δ-mutant;
Note =
4-1BB is also referred to as CD137; "+" refers to the fusion of the different regions.

III. Engineered NLV/A2-Specific Cells

Antigen-specific cells can be generated by using the NLV/A2-specific TCRs provided herein. For example, the TCR or CAR sequence may be inserted into a vector (e.g., retroviral or lentiviral vector) that is introduced into host cells, such as T cells (e.g., CD4⁺ T cells, CD8⁺ T cells, γδ T cells, or Tregs), NK cells, invariant NK cells, NKT cells, mesenchymal stem cells (MSCs), or induced pluripotent stem (iPS) cells to generate antigen-specific cells that can be used for adoptive cell therapy. For example, the host cells may be autologous or allogeneic cells (e.g., isolated from an umbilical cord).

Further provided herein are cells, such as T cells, NK cells, invariant NK cells, or NKT cells, engineered to express the NLV/A2-specific TCR or CAR provided herein. These effector immune cells may express a TCR together with CD3 molecules or other signaling domains linked to the TCR, which would initiate the signal transduction in these cells.

The engineered immune cells may be constructed using any of the many well-established gene transfer methods known to those skilled in the art. In certain embodiments, the engineered cells are constructed using viral vector-based gene transfer methods to introduce nucleic acids encoding an NLV/A2-specific TCR. The viral vector-based gene transfer method may comprise a lentiviral vector, a retroviral vector, an adenoviral or an adeno-associated viral vector. In certain embodiments, the engineered cells are constructed using non-viral vector-based gene transfer methods to introduce nucleic acids encoding a NLV/A2-specific TCR or CAR. The vector for the TCR may comprises the alpha chain polypeptide and the beta chain polypeptide, which may be linked by a linker domain or IRES sequence. The linker domain may comprise one or more cleavage sites, such as a Furin cleavage site and/or a P2A cleavage site, which may be separated by a spacer, such as SGSG or GSG. In certain embodiments, the non-viral vector-based gene transfer method comprises a gene-editing method selected from the group consisting of a zinc-finger nuclease (ZFN), a transcription activator-like effector nuclease (TALENs), and a clustered regularly interspaced short palindromic repeats (CRISPR)/CRISPR-associated protein 9 (Cas9) nuclease. In certain embodiments, the non-viral vector-based gene editing method comprises a transfection or transformation method selected from the group consisting of lipofection, nucleofection, virosomes, liposomes, polycation or lipid: nucleic acid conjugates, naked DNA, artificial virions, and agent-enhanced uptake of DNA.

IV. Methods of Use

As used herein, the terms "treat," "treatment," "treating," and the like refer to the process of ameliorating, lessening, or otherwise mitigating the symptoms of a disease or condition in a subject by, for example, administering a therapeutic agent to the subject, or by performing a surgical, clinical, or other medical procedure on the subject.

As used herein, the terms "subject" or "patient" are used interchangeably herein to refer to an individual, e.g., a human or a non-human organism, such as a primate, a mammal, or a vertebrate.

As used herein, the terms "therapeutically effective" or "therapeutically beneficial" and the like refer to a therapeutic agent, or a surgical, clinical, or other medical procedure that ameliorates, mitigates or otherwise relieves one or more symptoms of a disease, disorder, or condition, thereby enhancing the well-being of a subject having a disease, disorder, or condition by, for example, reducing the frequency or severity of the signs or symptoms of a disease, disorder, or condition. Thus, a therapeutically effective or therapeutically beneficial cancer treatment may, for example, reduce the size of a tumor, reduce the growth rate of a tumor, reduce the likelihood of tumor dissemination or metastasis.

Provided herein are methods for treating a disease or disorder in a subject comprising administering to the subject a therapeutically effective amount of a soluble TCR of the present embodiments to a population of NLV/A2-specific cells, such as T cells, NK cells, invariant NK cells, NKT cells, MSCs, or iPS cells, produced by any of the methods provided herein. Also provided are methods of using a soluble TCR of the present embodiments to detect the presence of NLV/A2 in the surface of a cell, either in vitro or in vivo.

Provided herein are methods for treating or delaying progression of cancer in an individual comprising administering to the individual an effective amount an NLV/A2-specific T cell therapy, wherein the patient has a cancer where CMV has been reactivated. Adoptive T cell therapies with genetically engineered TCR-transduced T cells (conjugate TCR to other bioreactive proteins (e.g., anti-CD3)) are also provided herein.

Tumors for which the present treatment methods are useful include any malignant cell type expressing NLV due to reactivation of CMV, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, brain cancer (glioblastoma), lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

In certain embodiments, the method further comprises a step of performing lymphodepletion prior to administration of the therapeutically effective amount of the population of NLV/A2-specific TCR cells. In certain embodiments, the lymphodepletion comprises non-myeloablative lymphodepleting chemotherapy. In certain embodiments, the non-myeloablative lymphodepleting chemotherapy comprises administration of cyclophosphamide and fludarabine.

In certain embodiments, the method further comprises a step of administering a T-cell growth factor that promotes the growth and activation of autologous T cells to the subject, either concomitantly with the autologous T cells or subsequently to the autologous T cells. In certain embodiments, the T cell growth factor comprises any suitable growth factor that promotes the growth and activation of the autologous T-cells. In certain embodiments, the T cell growth factor is selected from the group consisting of interleukin (IL)-2, IL-7, IL-15, and IL-12, and combinations thereof (e.g., IL-2 and IL-7, IL-2 and IL-15, IL-7 and IL-15, IL-2, IL-7 and IL-15, IL-12 and IL-7, IL-12 and IL-15, or IL-12 and IL-2).

In certain embodiments, the therapeutically effective amount of the population of NLV/A2-specific TCR cells produced by any of the methods provided herein is administered to the subject intravenously, intratumorally, or intraperitoneally. The appropriate dosage of the cell therapy may be determined based on the type of cancer to be treated, the severity and course of the disease, the clinical condition of the individual, the individual's clinical history and response to the treatment, and the discretion of the attending physician.

A. Combination Therapies

In certain embodiments, the compositions and methods of the present embodiments involve an antigen-specific cell population or soluble TCR in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is a chemotherapy such as, e.g., dacarbazine, or temozolomide. The additional therapy may be one or more of the chemotherapeutic agents known in the art.

A T cell therapy or soluble TCR may be administered before, during, after, or in various combinations relative to an additional cancer therapy, such as immune checkpoint therapy. The administrations may be in intervals ranging from concurrently to minutes to days to weeks. In embodiments where the T cell therapy or soluble TCR is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an antigen-specific T cell therapy, peptide, or TCR is "A" and an anti-cancer therapy is "B":

| | | | |
|---|---|---|---|
| A/B/A | B/A/B | B/B/A | A/A/B |
| A/B/B | B/A/A | A/B/B/B | B/A/B/B |
| B/B/B/A | B/B/A/B | A/A/B/B | A/B/A/B |

-continued

| A/B/B/A | B/B/A/A | B/A/B/A | B/A/A/B |
|---------|---------|---------|---------|
| A/A/A/B | B/A/A/A | A/B/A/A | A/A/B/A |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammal1 and calicheamicin omegal1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine;

androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as 7-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells.

Antibody-drug conjugates have emerged as a breakthrough approach to the development of cancer therapeutics. Cancer is one of the leading causes of deaths in the world.

Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer,* 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Patent Nos. U.S. Pat. Nos. 8,735,553, 8,354,509, and 8,008, 449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a human- ized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as treme- limumab; formerly ticilimumab), U.S. Pat. No. 6,207,156; Hurwitz et al. (1998) *Proc Natl Acad Sci USA* 95(17): 10067-10071; Camacho et al. (2004) *J Clin Oncology* 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art- recognized antibodies for binding to CTLA-4 also can be used. For example, a humanized CTLA-4 antibody is described in International Patent Application No. WO2001014424, WO2000037504, and U.S. Pat. No. 8,017, 114; all incorporated herein by reference.

An exemplary anti-CTLA-4 antibody is ipilimumab (also known as 10D1, MDX- 010, MDX- 101, and Yervoy®) or antigen binding fragments and variants thereof (see, e.g., WO 01/14424). In other embodiments, the antibody com- prises the heavy and light chain CDRs or VRs of ipilim- umab. Accordingly, in one embodiment, the antibody com- prises the CDR1, CDR2, and CDR3 domains of the VH region of ipilimumab, and the CDR1, CDR2 and CDR3 domains of the VL region of ipilimumab. In another embodi- ment, the antibody competes for binding with and/or binds to the same epitope on CTLA-4 as the above- mentioned antibodies. In another embodiment, the antibody has at least about 90% variable region amino acid sequence identity with the above-mentioned antibodies (e.g., at least about 90%, 95%, or 99% variable region identity with ipilim- umab).

Other molecules for modulating CTLA-4 include CTLA-4 ligands and receptors such as described in U.S. Pat. Nos. U.S. Pat. Nos. 5,844,905, 5,885,796 and International Patent Application Nos. WO1995001994 and WO1998042752; all incorporated herein by reference, and immunoadhesins such as described in U.S. Pat. No. 8,329, 867, incorporated herein by reference.

4. Surgery

Approximately 60% of persons with cancer will undergo surgery of some type, which includes preventative, diagnos- tic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radio- therapy, hormonal therapy, gene therapy, immunotherapy, and/or alternative therapies. Tumor resection refers to physi- cal removal of at least part of a tumor. In addition to tumor resection, treatment by surgery includes laser surgery, cryo- surgery, electrosurgery, and microscopically-controlled sur- gery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. 5. Other Agents It is contemplated that other agents may be used in combination with certain aspects of the present embodi- ments to improve the therapeutic efficacy of treatment. These additional agents include agents that affect the upregulation of cell surface receptors and GAP junctions, cytostatic and differentiation agents, inhibitors of cell adhe- sion, agents that increase the sensitivity of the hyperprolif- erative cells to apoptotic inducers, or other biological agents. Increases in intercellular signaling by elevating the number of GAP junctions would increase the anti-hyperproliferative effects on the neighboring hyperproliferative cell popula- tion. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodi- ments. Examples of cell adhesion inhibitors are focal adhe- sion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

B. Pharmaceutical Compositions

In select embodiments, it is contemplated that a cell expressing a TCR as disclosed herein, a protein containing the variable regions of a TCR, or a DNA encoding the variable regions of a TCR of the present invention may be comprised in a composition and administered to a subject to induce a therapeutic response in the subject. A therapeutic composition for pharmaceutical use in a subject may com- prise a TCR composition disclosed herein, such as a soluble TCR (optionally attached to an imaging agent), and a pharmaceutically acceptable carrier.

The phrases "pharmaceutical," "pharmaceutically accept- able," or "pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, anti- fungal agents), isotonic agents, absorption delaying agents, salts, preservatives, drugs, drug stabilizers, gels, binders, excipients, disintegration agents, lubricants, sweetening agents, flavoring agents, dyes, such like materials and com- binations thereof, as would be known to one of ordinary skill in the art (see, for example, Remington: The Science and Practice of Pharmacy, 21st edition, Pharmaceutical Press, 2011, incorporated herein by reference). Except insofar as any conventional carrier is incompatible with the active ingredient, its use in the vaccine compositions of the present invention is contemplated.

A person having ordinary skill in the medical arts will appreciate that the actual dosage amount of a therapeutic composition administered to an animal or human patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

A therapeutic composition disclosed herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctivally, intravesicularlly, mucosally, intrapericardially, intraumbilically, intraocularly, orally, topically, locally, and by inhalation, injection, infusion, continuous infusion, lavage, and localized perfusion. A therapeutic composition may also be administered to a subject via a catheter, in cremes, in lipid compositions, by ballistic particulate delivery, or by other method or any combination of the forgoing as would be known to one of ordinary skill in the art.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

In other embodiments, a composition comprises an immobilized or encapsulated TCR or soluble TCR disclosed herein and a support substrate. In these embodiments, a support substrate can include, but is not limited to, a lipid microsphere, a lipid nanoparticle, an ethosome, a liposome, a niosome, a phospholipid, a sphingosome, a surfactant, a transferosome, an emulsion, or a combination thereof. The formation and use of liposomes and other lipid nano- and microcarrier formulations is generally known to those of ordinary skill in the art, and the use of liposomes, microparticles, nanocapsules and the like have gained widespread use in delivery of therapeutics (e.g., U.S. Pat. No. 5,741,516, specifically incorporated herein in its entirety by reference). Numerous methods of liposome and liposome-like preparations as potential drug carriers, including encapsulation of peptides, have been reviewed (U.S. Pat. Nos. 5,567,434; 5,552,157; 5,565,213; 5,738,868 and 5,795,587, each of which is specifically incorporated in its entirety by reference).

A soluble TCR may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Sterile injectable solutions are prepared by incorporating the active peptides in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials & Methods

Display of recombinant RA14 variants on the CHO cell surface. The amino acid sequences of the of the extracellular alpha and beta chains of the human TCR β A14 were obtained from the protein data bank (PDB 3GSN; Gras et al., 2009), with the constant regions including the native-PESSC and -C on the alpha and beta chain C-termini, respectively. Minor changes were introduced into this sequence: Vα:1I and Vβ:M2A were added to match the germline TRAV24 and TRBV6-5 sequences (IMGT), and αA78V (PDB residue 152) substitution was made to match the germline TRAC gene (UniProt). These sequences were then reverted to DNA with CHO cell optimized codons and synthesized as a gblock (IDT). These were assembled into a cassette with a murine IgH leader sequence (Smith et al., 2009) followed by one TCR chain, a T2A cleavage site with furin cut site (bold) and GSG linker (italics; sequence: RRKRGSGEGRGSLLTCGDVEENPGP (SEQ ID NO:

43)), then the second TCR chain fused to a PDGFR trans-membrane region (FIG. 1A) (Chng et al., 2015). The TCR chains were cloned in both orientations, alpha-T2A-beta and beta-T2A-alpha. The constant regions were further modified to create a disulfide variant (ds) by introducing the amino acid substitutions Vα:T84C, Vβ:S79C, and Vβ:C85.1A to move the terminal disulfide to a more central position and remove a free cysteine (Boulter et al., 2003). The cassette was cloned into a pcDNA3 (Invitrogen) backbone for tran-sient expression and moved into a pPyEBV backbone (Acyte Biotech) for semi-stable replication used during library sorting (Nguyen et al., 2018).

CHO cell transfection for TCR display analysis. CHO-T cells (Acyte Biotech) were grown in CHO—S-SFM II media (Gibco) supplemented with 2× GlutaMax and penicillin/streptomycin. For transfection, cells were spun and resus-pended at a concentration of $1.5\times10^6$ cells/mL, with 2 mL plated per well in a 6-well plate. For each well, 250 μL of OptiMEM (ThermoFisher) was mixed with 10 μL of Lipo-fectamine 2000 (ThermoFisher) and added to another tube with 250 μL of OptiMEM and 4 μg of DNA. The solution was mixed and allowed to equilibrate for 30 minutes at room temperature, before adding the solution to the appropriate well. The next day, cells were fed an additional 1 mL of media.

TCR library design and cloning. Two separate libraries were generated, one targeting the CDR3α and the other targeting CDR30 with saturation mutagenesis. The targeted region was defined as the single continuous stretch of residues in each CDR3 having direct contact with the pMHC (Gras et al., 2009), as well as an additional residue on either side to confer additional loop flexibility (Vα:107-115, Vβ:108-115; FIGS. 2A-B). To limit library size and retain binding affinity, three residues forming hydrogen bonds with the peptide (Vα:114, Vβ:110, Vβ:114) were not randomized.

Libraries were generated using overlap PCR with degen-erate codons (CDR3α: NNS-NNS-NNS-AAC-NNS (SEQ ID NO: 44) and CDR3β: NBS-VBC-ACC-VBC-VBC-VBC-TAC-NBS (SEQ ID NO: 45)) and Q5 hot-start master mix (NEB). The PCR insert and pPyEBV backbone were both digested with restriction enzymes flanking each tar-geted region (for CDR3α, AgeI and NheI; for CDR3β, BamHI and NheI, NEB), gel extracted, and desalted. For each library ~1 μg of vector was ligated with insert at a 3:1 (CDR3α) or 6:1 (CDR3β) ratio overnight using T4 ligase (NEB). The following day, ligations were desalted and transformed into fresh NEB10β electrocompetent cells. After one hour of recovery, dilutions were plated and incubated, and colony counts used to estimate the library size. The library was grown to an $OD_{600}$ of 2 in liquid culture, which was then used to make frozen stocks and inoculate a new flask for overnight growth. Library DNA was prepared using a Maxiprep kit (Qiagen).

Tetramer preparation. Biotinylated HLA-A*0201 mono-mer loaded with the $pp65_{495-503}$ NLV peptide from human CMV or a control HCV peptide (Biolegend and the NIH tetramer facility) at 100 μg/mL was combined in a 4:1 molar ratio with streptavidin-conjugated to APC, AF647, or AF488 (ThermoFisher). Streptavidin was added slowly over 1 hour on ice to favor the formation of tetramer. Biotin (30 μM) was then added to block any unfilled biotin binding sites, and the tetramers incubated overnight at 4° C.

Flow cytometry and analysis. Transfected CHO-K1 or CHO-T cells (~$1\times10^6$) were centrifuged (250 g for 10 min) and resuspended in 100 μL PBS plus 2% FBS (Sigma) with 2 g/mL NLV or HCV tetramer and a 1:50 dilution of anti-Vβ6-5-PE (Beckman Coulter). Cells were stained on ice for 1 hour, then rinsed and resuspended in 0.5 mL PBS plus 2% FBS. Samples were run on a Fortessa cytometer (BD Biosciences). A forward- and side-scatter gate was used to select live cells, with TCR-positive cells defined as having a PE signal greater than or equal to $10^3$. To compare binding activity of TCR variants, NLV tetramer binding was nor-malized by TCR display level by dividing the AF647 signal by the PE signal on a per-cell basis for the TCR-positive population. All analyses were performed with FlowJo soft-ware.

Library transfection and sorting. Confluent CHO-T cells (1 or 2 T-150 flasks) were transfected as above, with quantities scaled accordingly. Library DNA was diluted 1:4 with an inert yeast plasmid as carrier DNA (pCTCON) (Colby et al., 2004) so that each CHO cell received at most one TCR expressing pPy plasmid. Flasks were also trans-fected with the wild-type pPy_RA14 as a positive control and pPy_hu4D5 expressing the anti-HER2 Fab as a negative control. Two days later, cells were scanned for TCR surface display using the anti-Vb6-5 antibody to evaluate transfec-tion efficiency, and media replaced with half-strength selec-tive media (CHO—S-SFM II plus 2× GlutaMax plus 150 μg/mL Hygromycin). Four or five days after transfection, cells were expanded and transferred into full-strength selec-tive media with 300 μg/mL hygromycin. Cells were main-tained in selective media until reaching confluence in a T-150 (~2 weeks).

For sorting, ~$1\times10^7$ live cells were centrifuged (250 g, 5 min) and resuspended in OptiMEM plus 1% BSA and stained with anti-TCR Vβ6-5 and NLV tetramer as described above. Cells were sorted using a FACSAria, with the sort gate drawn to collect most fluorescent ~1-2% of the popu-lation, biased towards cells showing higher tetramer binding at the same TCR display level, to collect ~$1\times10^5$ cells. The sorted cells were expanded for ~1 week, and the process repeated two times. To recover plasmid from sorted CHO cells, genomic DNA was prepared from the pooled popula-tion one week after each sort. The region of interest (CDR3α or 3β, depending on the library) was PCR-amplified using flanking primers and 500 ng template DNA. PCR product was ligated into a TOPO vector (Invitrogen/Thermo Fisher) or digested and ligated into empty pPy backbone. After transformation, 10-40 individual colonies were sequenced from each round of sorting.

Expression of soluble TCR-Fc fusion proteins. To express soluble TCR-Fc fusion proteins, DNA encoding the RA14 extracellular alpha and beta chains was cloned into pcDNA3.0 plasmids downstream of a human IgG heavy chain leader sequence. Both the native human TCR constant domains and versions with the additional inter-chain disul-fide introduced were used. The Ca domain was followed by the upper hinge sequence of human IgG1 (VEPKSC (SEQ ID NO: 46)) and then the Fc domains. The native IgG1 light chain cysteine was inserted at the C-terminus of CP to pair with the cysteine in the upper hinge and further stabilize the TCR constant domains. Additional modifications included the removal of five N-linked glycosylation sites predicted by NetNGlyc 1.0 Server (DTU Bioinformatics; available on the world wide web at cbs.dtu.dk/services/NetNGlyc/) by intro-ducing α:N20Q, α:N177Q, α:N188Q, β:N65Q, and β:N184Q substitutions (FIG. 5A).

In one version, the construct consisted of alpha-T2A-beta-huIgG1 hinge, $C_H2$ and $C_H3$ domains, in another these two chains were encoded on separate pcDNA3.0-based plas-mids, with either alpha or beta chain fused to the Fc. Both human IgG1 and mouse IgG2a hinge-Fc sequences were used (Uniprot #P01857 and #P01863, respectively). Constructs containing the mouse IgG2a Fc retained the human IgG1 VEPKSC before the mouse hinge-Fc sequence. Cloning was performed using Q5 hot-start polymerase (NEB) and either traditional digestion/ligation or Gibson assembly methods and confirmed by Sanger sequencing.

For large-scale expression, two T-150 flasks of adherent CHO-K1 cells (ATCC #CCL-61) were grown to confluency and transfected using the same cell/media/reagent ratio described above for each variant. Cells were grown in high-glucose DMEM (Sigma) with 10% low-IgG FBS (ThermoFisher) and no antibiotics at 37° C. with 5% $CO_2$. Media was replaced the day after transfection and cells were transferred to a 32° C., 5% $CO_2$ incubator for one week. Media was harvested and loaded onto a protein A column using an FPLC (ÅKTAPure, GE healthcare) using 100 mM phosphate, 150 mM NaCl, pH 7.2 and eluted with 100 mM glycine, pH 2.5. The eluate was immediately neutralized with 1M Tris, pH 8, and buffer-exchanged into PBS, pH 7.4, using a centrifugal filter (Amicon or Centricon).

Protein biophysical characterization. Purified TCR-Fc proteins (3 μg each) were prepared in reducing or non-reducing 6×SDS loading buffer and incubated for five minutes at 80° C. or 42° C., respectively. Samples were run on a 4-20% gradient gel (BioRad) and stained with GelCode Blue (ThermoFisher Scientific). Size exclusion chromatography was performed with 100 μg purified protein in 100 μL using a Superdex S200 column and Åkta FPLC with PBS as the running buffer and Gel Filtration Calibration Kit High and Low molecular weight standards (GE Healthcare). For affinity variants, the peak eluting at ~10.5 mL containing properly assembled, bivalent TCR-Fc was collected and concentrated. To monitor thermal stability, protein was prepared at 200 μg/mL and diluted with protein thermal shift dye (ThermoFisher Scientific) following the recommended protocol. Samples were heated at 1° C./min on a RT-PCR machine measuring fluorescence.

Protein-protein binding assays. For ELISA analyses, high-protein binding plates (Costar) were coated with 1 μg/mL of NLV/A2, HCV/A2 tetramer or nothing in PBS overnight at 4° C., before blocking with 5% milk in PBS with 0.05% Tween-20 (PBS-T) for one hour at room temperature. The plate was washed three times with PBS-T, purified TCR-Fc titrated in 1:5 dilution steps from 10 μg/mL and incubated for one hour. After washing again, 1:1000 dilution of goat-anti-human Fc-HRP conjugate (Southern Biotech) was added to the plate for one hour. After a final wash, the plate was developed with TMB (Fisher Scientific), quenched with 1N HCl, and absorbance measured at 450 nm on a Molecular Devices Spectramax. All plated volumes were 50 μL. Data were analyzed with Graphpad Prism 5.

Dynamic and equilibrium binding kinetics were obtained using a BIAcore 3000 instrument. The purified TCR-Fc was immobilized on a CM5 sensor chip (GE Healthcare) via EDC/NHS coupling using a sodium acetate buffer at pH 4.0 for a total of 2000-5000 response units, with a blank flow cell used as the reference channel. Monomeric NLV/A2 was injected at concentrations ranging from 4 to 1000 nM at 30 μL/min for two minutes and allowed to dissociate for six minutes, which resulted in a return to baseline without regeneration. The negative control HCV/A2 monomer was injected at the highest concentration for all variants. All data was measured at 25° C. On rate, off rate, and equilibrium affinity analyses were performed using BIAEvaluation 3.0 software and fit using the 1:1 Langmuir binding model. All injections were performed twice and final kinetic values reported are the average and standard deviation for the entire dataset.

Staining peptide-pulsed antigen-presenting cells. Human TAP-deficient T2 lymphoblasts (174×CEM.T2; ATCC #CRL-1992) expressing empty HLA-A2 were cultured in IMDM media supplemented with 4 mM glutamine at 37° C. and 5% $CO_2$. The $pp65_{495-503}$ peptide NLVPMVATV (SEQ ID NO: 41) and control $HCV_{1406-1415}$ peptide KLVALGI-NAV (SEQ ID NO: 42) were produced by solid phase synthesis (Peptide 2.0) and dissolved in DMSO for a final peptide stock of 50 mM. T2 cells in a six-well plate (2 mL/well) containing $10^6$ cells/mL were adjusted to 100 μM or the indicated peptide concentration and incubated at 37° C. After 24 hours, $5×10^5$ cells per sample were stained on ice for one hour using 2 μM of purified TCR-mFc in PBS with 1% FBS (PBS-F) with 50 μg/mL human Fc block (BD Biosciences) in a 50 μL volume. Cells were washed twice with PBS-F and bound TCR-mFc detected with a 1:500 dilution of goat-anti-mouse Fc-AF647 (Jackson Immunobiology) for another hour. After a final wash, cells were resuspended and assayed for AF647 signal using a flow cytometer (Fortessa, BD Biosciences).

Activation of human Jurkat T cells expressing RA14 variants. A pcDNA3.1-derived plasmid with a CMV promoter was modified to support transient expression of a signaling-competent TCR comprised of the RA14 variable regions and mouse constant/transmembrane regions. First, a Kozak sequence with optimal ribosome binding site (sequence: CC ACC ATG G), multiple cloning site, and stop codon followed by a HindIII site and terminal SV40 PolyA tail signal were added to pcDN3.1. Next, separate plasmids containing the TCR alpha and beta chains were cloned. The pRA14a alpha chain plasmid includes a murine alpha chain TCR signal sequence from IMGT TRAV5D-4 (amino acid sequence: MKTYAPTLFMFLWLQLDGMSQ (SEQ ID NO: 47)) in-frame with the human TCR alpha variable region, both flanked by restriction sites EcoRI and AflII and the murine TCR alpha constant region (TRAC*01) and alpha transmembrane domain between restriction sites AflII and HindIII. The pRA14b beta chain plasmid was constructed similarly, but with the murine beta chain signal sequence from IMGT TRBV13-2 (MGSRLFFVLSSLLCSKHM (SEQ ID NO: 48)) and human variable beta domain flanked by EcoRI and AflII sites and beta constant region (TRBC*02) and beta transmembrane domain between restriction sites AflII and HindIII. Signal sequences were encoded by oligonucleotides, constant regions amplified from mouse DO11.10 hybridoma mRNA by RT-PCR. Altered RA14 variable regions were introduced by PCR amplification followed by digestion/ligation into the EcoRI and AflII sites.

Human Jurkat T-cells, clone E6-1 (ATCC #TIB-152) were grown in RPMI 1640 media with 10% FBS and 100 units/mL penicillin-streptomycin (Sigma) and transfected as previously described (Goyarts et al., 1998). Briefly, $10^6$ cells per transfection were centrifuged at 250 g for five minutes, resuspended in 5 mL OptiMEM and incubated at room temperature for eight minutes. Cells were centrifuged as before and resuspended in 400 μL OptiMEM. Cells were then mixed with 7.5 μg of each alpha and beta plasmid in a 4 mm electroporation cuvette (Fisher) and incubated for eight minutes before pulsing exponentially with 250V, 950 μF, and ∞Ω on a Biorad GenePulser. After an eight-minute recovery period, cells were rescued with 7 mL of RPMI 1640 (supplemented with 10% FBS and antibiotics) in a T-25 flask at 37° C. and 5% $CO_2$. After 18-24 hours, recombinant TCR expression was monitored by flow cytometry, with the RA14 display level monitored by the anti- TRBV6-5 antibody-PE and binding activity monitored by NLV/A2 tetramer-AF647, as described above.

The ability of transfected RA14 variants to activate Jurkat cells was monitored by CD69 upregulation after incubation with peptide-pulsed T2 cells. T2 cells ($10^5$) were pulsed with NLV and HCV peptides at 0.1 µM for four hours. T2 cells were washed once in RPMI to remove excess peptide. Transfected Jurkat cells ($10^5$) were co-cultured with pulsed T2 cells at a TCR-positive effector: target ratio of 1:1. After 24 hours, cells were collected and incubated with 50 µg/mL human Fc block (BD Biosciences) for 10 minutes before adding anti-TRBV6-5-PE, NLV/A2 tetramer-AF647, and anti-CD69-FITC (Biolegend; 1 µL of each antibody and 5 nM of tetramer per 50 µL staining volume) for one hour on ice. Cells were scanned on a Fortessa cytometer (BD Biosciences) and gated for display of RA14 variants (PE signal≥500) to exclude T2 cells. All analyses were performed with FlowJo.

Example 1—Display of Pp65 NLV-Specific TCR β A14 on the CHO Cell Surface

To first determine the level of recombinant TCR displayed on the CHO cell surface, the truncated extracellular alpha and beta chains of the human RA14 TCR were cloned into a pcDNA3-based plasmid with a CMV promoter, human IgH leader sequence, one TCR chain, and T2A peptide sequence followed by the second TCR chain fused in-frame to a platelet-derived growth factor receptor (PDGFR)-derived transmembrane region (FIG. 1A). As only the second chain is fused to the transmembrane region and chain order can impact yields (Maynard et al., 2005), the chains were cloned in both the α/β-TM and β/α-TM orientations. Similarly, since moving the terminal inter-chain di-sulfide bond to the Cα:T84C and Cβ:S79C position (IMGT numbering used throughout) and removing the free cysteine at position Cβ85.1 has been reported to improve expression of soluble and phage/yeast displayed TCRs (Boulter et al., 2003; Ho et al., 1998), these modifications were also tested in each chain orientation.

After cloning and sequence confirmation, midi-prepped plasmid DNA was transiently transfected into CHO-T cells and TCR surface display assessed by flow cytometry two days later. The presence of TCR on the cell surface was monitored by an antibody binding the human variable beta chain (Vβ6-5-PE), while NLV/A2 tetramers conjugated to APC were used to assess ligand binding activity. A tetramer presenting an unrelated peptide from hepatitis C virus (HCV1406-1415 sequence: KLVALGINAV (SEQ ID NO: 42); hereafter called HCV) complexed with A2 was used to evaluate peptide specificity (FIG. 1B).

Flow cytometry showed varying expression patterns for each vector design, with the PE+/APC+ population indicative of cells binding tetramer and displaying TCR (FIG. 1C). Cells transfected with empty pcDNA3 vector showed minimal binding to either reagent, while a β-TM only construct bound the Vβ antibody, indicating that unpaired TCR chains will not be detected by tetramer binding. By contrast, cells transfected with constructs containing both TCR chains presented a diagonal double-positive population, indicating a correlation between tetramer staining and surface display over a range of expression levels. Staining with the control HCV tetramer also showed no binding, indicating that the displayed TCRs retained peptide specificity. All samples included a population of unstained, non-expressing cells, which is expected for eukaryotes with unsynchronized growth. While inclusion of the modified di-sulfide bond greatly increased the specific tetramer binding activity (tetramer binding: TCR display ratio), chain order had less impact. A small but consistent improvement was detected in specific tetramer binding activity for the α/β-TM configuration. Accordingly, this design with the modified di-sulfide was selected for further use.

Example 2—Design of CDR3α and CDR3P Libraries

Analysis of the RA14-NLV/A2 crystal structure revealed that RA14 engages nearly all solvent-exposed peptide residues and forms hot spots with peptide residues P4:Pro, P5:Met and P8:Thr (Gras et al., 2009). In the alpha chain, CDR3α:N114 forms a key hydrogen bond with P5:Met which is also present in structure of the related TCR C7 with NLV/A2 (Yang et al., 2015), which has a nearly identical CDR3α. In the beta chain, CDR3β:T110 forms multiple hydrogen bonds with P8:Pro. To identify high affinity RA14 variants, separate CDR3α and CDR30 libraries were designed, which allowed a larger sequence space for each CDR to be probed. Three anchor residues (Vα:N114, Vβ:T110 and Vβ:Y114) were retained while four or six residues flanking these contacts were randomized to optimize the TCR-pMHC interface (FIG. 2).

To create each library, primers incorporating degenerate codons were designed to maximize amino acid diversity while keeping the theoretical library sizes ($1\times10^6$ for CDR3α, $4\times10^6$ for CDR30) near ~$10^6$, a limitation determined by mammalian cell culture volume constraints. Mutagenized cassettes were generated using overlap PCR with these primers, followed by overlap extension PCR to produce full-length inserts. These were digested and ligated into the pPyEBV vector, which allows semi-stable, selectable transfection in CHO-T cells (Nguyen et al., 2018). After transformation into E. coli, actual library sizes were estimated as $4\times10^5$ for the CDR3α library and $1\times10^6$ for the CDR3β library, with diversity confirmed by DNA sequencing.

Example 3—Selection of RA14 Variants with Improved Tetramer Binding

Pooled library plasmids were diluted with a 1:4 molar ratio of carrier DNA, to ensure each cell will acquire at most one library clone, and transfected into CHO-T cells (Nguyen et al., 2018). After two weeks of growth under antibiotic selection to eliminate cells lacking the pPy plasmid, cells were stained with AlexaFluor-647 (AF647)-labelled NLV/A2-tetramers to detect ligand binding and anti-V$_β$6-5-PE to detect surface TCR display. Each library was sorted by FACS to collect the 1-2% of cells with the highest ratio of tetramer binding to TCR display. After sorting, each library was allowed one week of recovery before being sorted again, for a total of three rounds. Comparison of the libraries at each step demonstrated enrichment of clones with high levels of tetramer binding (FIGS. 3A-B). The CDR3α and CDR3β libraries each showed a 5-10-fold increase in the number of cells falling within the gated area per round.

TCR sequences were recovered from pooled cells after round three sorting by PCR amplification from total cellular DNA, followed by re-cloning into the pPyEBV plasmid for sequencing. Analysis of 20-35 colonies revealed seven unique CDR3α and 10 unique CDR3β sequences (Tables 3A-B). The wild-type residues were largely retained at positions Vβ:109 and Vβ:111 within the CDR3β library, while positions Vβ:112 and Vβ:113 were highly variable. RA14 covers an unusually high percent of the exposed peptide upon binding, and in particular that the CDR3β contacts are mostly backbone-mediated, which may explain the high variation possible in these residues (Gras et al., 2009). Finally, larger residues were frequently found in the flanking sites, which may have been preferentially enriched if they were able to introduce additional peptide contacts.

48 similar to or improved over wild-type, with the best variant (αV2) having a 2.3-fold increase in normalized binding. In contrast, all 10 of the CDR3β variants showed significant improvements over wild-type, with 1.8- to 3.5-fold improved specific tetramer binding. The variants with the greatest specific tetramer binding activity (αV1, αV2, βV1, βV4, βV7, and βV8) were selected for further analysis.

TABLE 3A

Amino acid sequences of RA14 CDR3α variants isolated from round 3 sorting.

| Variant | SEQ | CDR3α | | | | | | | |
|---|---|---|---|---|---|---|---|---|---|
| IMGT # | ID NO: | 104 | 105 | 106 | 107 | 108 | 109 | 114 | 115 |
| WT | 39 | C | A | R | N | T | G | N | Q |
| Library | 49 | C | A | R | * | * | * | N | * |
| CDR3α1 | 1 | C | A | R | N | S | G | N | P |
| CDR3α2 | 2 | C | A | R | N | Y | G | N | H |
| CDR3α3 | 3 | C | A | R | N | Y | I | N | T |
| CDR3α4 | 4 | C | A | R | S | F | G | N | P |
| CDR3α5 | 5 | C | A | R | S | V | G | N | S |
| CDR3α6 | 6 | C | A | R | L | L | A | N | L |
| CDR3α7 | 7 | C | A | R | G | S | W | N | Q |

TABLE 3B

Amino acid sequences of RA14 CDR3β variants isolated from round 3 sorting.

| Variant | SEQ | CDR3β | | | | | | | | | | | | |
|---|---|---|---|---|---|---|---|---|---|---|---|---|---|---|
| IMGT # | ID NO: | 105 | 106 | 107 | 108 | 109 | 110 | 111 | 112 | 113 | 114 | 115 | 116 | 117 |
| WT | 40 | A | S | S | P | V | T | G | G | I | Y | G | Y | T |
| Library | 50 | A | S | S | * | * | T | * | * | * | Y | * | Y | T |
| CDR3β1 | 8 | A | S | S | P | V | T | G | G | V | Y | L | Y | T |
| CDR3β2 | 9 | A | S | S | R | V | T | G | G | V | Y | L | Y | T |
| CDR3β3 | 10 | A | S | S | P | I | T | G | S | T | Y | I | Y | T |
| CDR3β4 | 11 | A | S | S | P | I | T | G | A | P | Y | L | Y | T |
| CDR3β5 | 12 | A | S | S | P | V | T | G | S | S | Y | G | Y | T |
| CDR3β6 | 13 | A | S | S | W | I | T | G | S | I | Y | T | Y | T |
| CDR3β7 | 14 | A | S | S | P | V | I | G | S | S | Y | W | Y | T |
| CDR3β8 | 15 | A | S | S | L | V | T | G | G | V | Y | L | Y | T |
| CDR3β9 | 16 | A | S | S | L | V | T | G | I | P | Y | L | Y | T |
| CDR3β10 | 17 | A | S | S | R | V | T | G | S | V | Y | G | Y | T |

Example 4—Characterization of RA14 Variants with Improved Tetramer Binding

All identified CDR variants were transfected into fresh CHO-T cells in combination with the complementary wild-type chain and analyzed for TCR display level and tetramer binding as single clones. To compensate for TCR expression level differences, the specific tetramer binding activity (tetramer-AF647 signal/anti-TCR-PE signal) was compared on a per cell basis for each clone. The median of this distribution was then normalized to the median value obtained for wild-type RA14 to report a fold-increase as compared to RA14 (FIGS. 3C-D). A similar process was performed after staining with the control HCV tetramers, revealing that peptide restriction was retained for all selected variants. Only two CDR3α variants (αV1, αV2) showed binding Next, it was determined whether the best alpha and beta variants could be combined to further improve tetramer binding, as reported in other studies (Li et al., 2005). The wild-type and selected alpha (αV1, αV2) and beta (βV1, βV4, βV7, βV8) variants were combined pairwise, transfected and analyzed as before. The combinations generally showed further improved specific tetramer binding (FIG. 4A), with some variation in TCR display levels among clones. As surface display levels can be useful predictors of soluble expression yields (Shusta et al., 1999), the αV2 and βV8 combination was selected as the lead candidate. Variant αV2 contains the Vα:T108Y and Vα:Q115H substitutions, while βV8 contains Vβ:P108L and the frequently-observed Vβ:I113V and Vβ:G115L mutations (Tables 3A-B).

To better understand the impact of the selected CDR changes on TCR function, TCR activation was evaluated after transfection into human Jurkat T cells. The native RA14 and selected αV2 and βV8 variable regions were combined with murine constant regions followed by human TCR transmembrane regions on a pcDNA-based plasmid. Mouse constant regions were used to prevent mispairing with the endogenous human TCR expressed in Jurkat cells (Cohen et al., 2006). After electroporation, Jurkat cells were co-cultured with human T2 antigen-presenting cells pre-incubated with 0.1 μM NLV or control HCV peptide and activation was measured by CD69-upregulation using flow cytometry 24 hours later (FIG. 4B). All TCRs tested showed activation in the presence of NLV but not HCV-pulsed T2 cells. Moreover, the engineered TCRs showed significantly improved activation (2.2-2.7-fold) as compared to the wild-type RA14. Although the selection strategy was based upon TCR display levels and tetramer binding, these data suggest that features required for TCR activation were also retained fected pairwise with plasmids encoding the wild-type RA14 chains to produce four variants: wild-type RA14 (WT), αV2.βWT, αWT.βV8, and αV2.βV8. After protein A purification, size exclusion chromatography (SEC) was performed to isolate the dominant peak (eluting at ~10.5 mL) containing protein with the highest tetramer binding activity and appearing to correspond to intact, bivalent protein. SDS-PAGE analysis showed similar, high levels of purity for all variants (FIG. 5A). Protein stability was compared by thermal unfolding, using differential scanning fluorimetry and using the inflection point of the first unfolding event to compare TCR domain stabilities. The βV8 changes are mildly destabilizing, inducing a >4° C. decrease in melting temperature as compared to RA14. In contrast, the αV2 changes increase thermal stability >2° C., and partially compensate for the presence of the less stable βV8 in the combined αV2.βV8 variant (Table 4).

TABLE 4

| | Affinity and stability of RA14 TCR-Fc variants. | | | | | | |
|---|---|---|---|---|---|---|---|
| Variant | Tm, glycosylated (° C.) | Tm, deglycosylated (° C.) | $k_a \times 10^5$, ($M^{-1} s^{-1}$) | $k_d \times 10^{-2}$, ($s^{-1}$) | $\chi^2$ | $K_d = k_d/k_a$ (nM) | Equilibrium $K_d$ (nM) |
| αWT.βWT | 67.9 ± 0.4 | 68.8 ± 0.3 | 0.95 ± 0.1 | 29 ± 0.2 | 1.7 ± 0.6 | 3092 ± 400 | 1480 ± 60 |
| α2.βWT | 70.2 ± 0.5 | 71.3 ± 0.1 | 3.1 ± 0.8 | 15 ± 1 | 14 ± 2 | 514 ± 100 | 570 ± 13 |
| αWT.β8 | 63.7 ± 0.7 | 64.1 ± 0.7 | 1.3 ± 0.02 | 3.2 ± 0.1 | 6.1 ± 0.6 | 243 ± 7 | 224 ± 7 |
| α2.β8 | 65.2 ± 0.1 | 67.0 ± 0.5 | 35 ± 0.02 | 1.8 ± 0.1 | 1.4 ± 0.1 | 53 ± 1 | 62 ± 1 |
| R2G | 64.3 ± 0.7 | ND | 3.89 ± 0.01 | 0.36 ± 1 × 10⁻² | 0.7 ± 0.04 | 9.2 ± 0.01 | ND |
| 2S-16 | 64.4 ± 0.6 | ND | 4.96 ± 0.17 | 0.029 ± 4 × 10⁻³ | 0.1 ± 0.01 | 0.59 ± 0.07 | ND |

(Sibener et al., 2018), which is not always the case for affinity matured TCRs.

Example 5—Production of RA14 TCR as a Soluble Fc-Fusion Protein

In order to fully characterize our engineered TCRs and to support future applications of high affinity NLV-binding TCRs, it was necessary to produce these as soluble proteins. TCRs are notoriously difficult to produce, with no generally successful strategies yet identified (Maynard et al., 2005 and Gunnarsen et al., 2013). Since TCRs are naturally produced by mammalian cells and since fusion of a poorly expressed protein to an antibody Fc domain generally increases expression level, increases avidity through bivalency, and provides a convenient detection handle for immunoassays, a TCR-Fc format was selected for production in CHO cells. Antibody expression plasmids were modified (Nguyen et al., 2015) to express the wild-type RA14 variable and constant domains with one chain fused to the human IgG1 upper and core hinge region, followed by human Fc domains.

Several constructs were evaluated by small scale CHO expression and ELISA to compare expression level, including a one plasmid system with the two chains separated by a T2A peptide and versions with either the beta or alpha chain fused to the Fc. For these, constant TCR domains with the modified inter-chain disulfide bond were used (named TCRds-huFc; Boulter et al., 2003) in addition to a second disulfide-bond joining the base of the TCR constant domains contributed by the antibody upper hinge sequence (named TCR2ds-huFc). The highest expression levels, approaching that observed with antibodies, were obtained with a two-plasmid system in which the α-chain was fused to the Fc.

To compare RA14 and the engineered variants in the TCR2ds-huFc format, the αV2 and βV8 domains were cloned into the two-plasmid expression system and trans-

Example 6—Engineered Variants Show Improved pMHC Affinity as Soluble TCR2ds-huFc Fusion To provide an initial assessment of NLV/A2 binding, the ability of purified TCR2ds-huFc variants to bind immobilized pMHC were compared in an ELISA. The NLV or HCV tetramer was coated onto an ELISA plate, TCR2ds-huFc protein titrated and detected by anti-human-Fc-HRP (FIG. 5B). No binding was detected for any variant to the control surface, while RA14 provided a clear dose-response curve on NLV tetramer coated wells, with a detection limit near 0.1 μg/mL. Both variants including the βV8 chain showed a distinct increase in binding, with the detection limit ~30-fold lower than observed for the other variants. In contrast, the αV2.βWT showed improved detection but a much shallower slope than observed for RA14.

Surface plasmon resonance was used to rigorously quantify binding of the four TCR-Fc variants to NLV/A2. SEC-purified TCR2ds-huFc was coupled to the sensor surface, with varying concentrations of NLV/A2 or HCV/A2 monomer passed over the surface. The WT RA14 exhibited the slow on-rates ($9.5 \times 10^4$ $M^{-1}s^{-1}$) and fast off-rates (0.29 sec⁻¹) typical of TCRs, resulting in a calculated affinity of 3.1 μM for the bivalent TCR2ds-huFc format. This compares well to the 6.3 μM $K_d$ previously reported for monovalent RA14 using an immobilized pMHC orientation, but is tighter than the 27.7 μM reported using immobilized TCR (Gras et al., 2009; Gakamsky et al., 2007). By contrast, the αV2 CDR changes affected only the on-rate, with a three-fold increase, while the βV8 CDR changes affected only the off-rate, with a 10-fold decrease (FIG. 5C). When combined, these changes showed synergy, conferring a 50 nM affinity for αV2.βV8, a 60-fold improved affinity over RA14 (Table 4). Equilibrium binding analyses yielded similar data (Table 4, FIGS. 6A-D). No variant exhibited detectable binding to the control HCV/HLA-A2 monomer at the highest concentrations used (FIG. 5C).

Example 7—Genetic Deglycosylation Yields Homogeneous TCR-Fc Protein

Figures 7A, 7B, 7C, 7D:
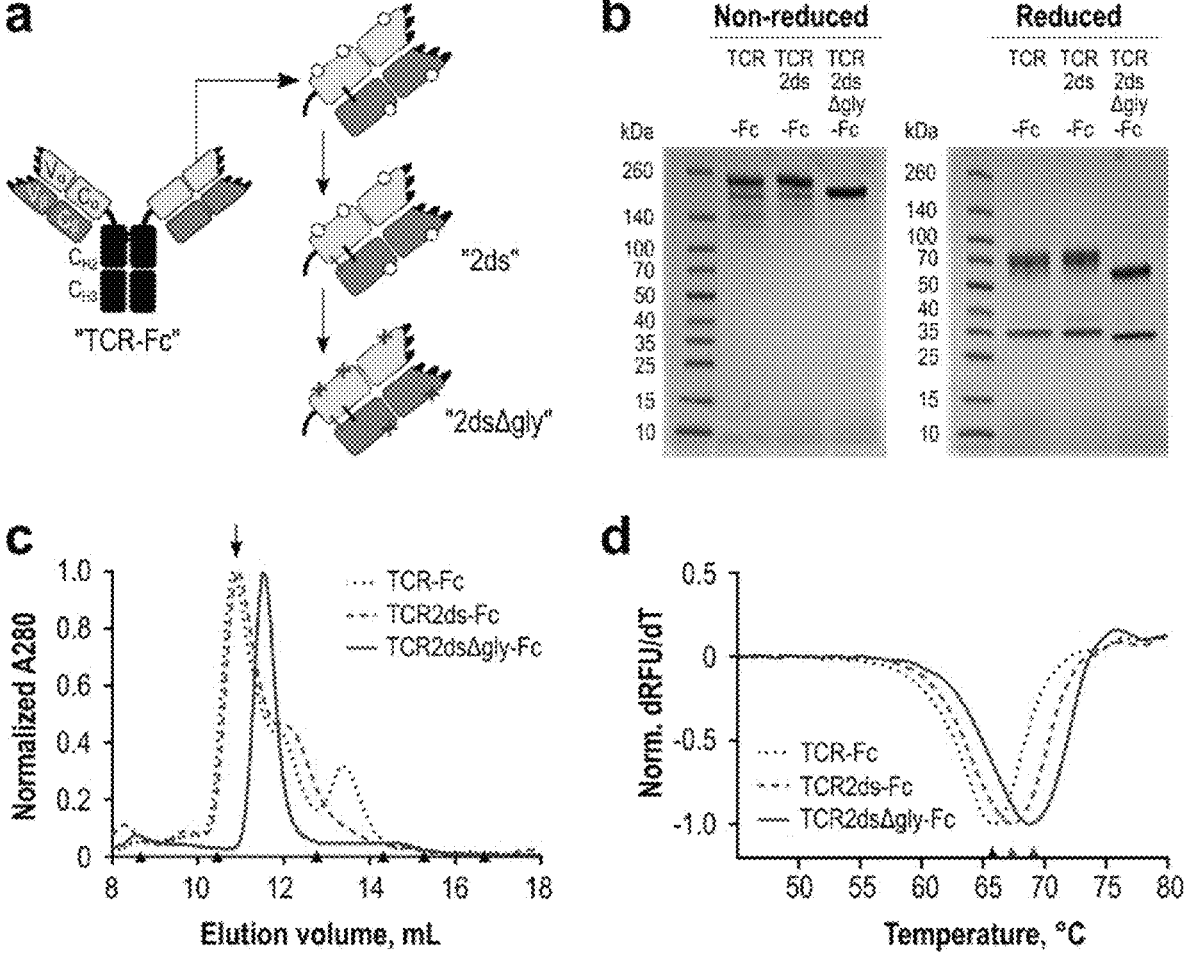

The success of affinity maturation prompted efforts to further improve soluble TCR-Fc expression. Specifically, reducing SDS-PAGE showed broad bands with approximately the expected size, while SEC showed two or three distinct peaks, indicating the presence of incompletely-assembled TCR-Fc species (FIGS. 7B-C). This prompted the evaluation of two hypotheses: first, that TCR-Fc assembly was improved by stronger $\alpha$-$\beta$ chain interactions from the additional disulfide bond (Boulter et al., 2003), and second, that assembly was sterically inhibited by TCR glycosylation, since RA14 includes several predicted N-linked glycosylation sites near chaininterfaces.

To evaluate these possibilities, several constructs were compared: one with only the engineered di-sulfide bond between the constant domains (TCRds-huFc), one with an additional di-sulfide bond (TCR2ds-huFc) and one in which five predicted N-linked glycosylation sites were disrupted by N-to-Q amino acid substitutions (TCR2ds$\Delta$gly-huFc; FIG. 7A). SDS-PAGE analysis shows that genetic de-glycosylation resulted in sharper protein bands (FIG. 7B). Introduction of the additional disulfide bond eliminated the minor SEC peak eluting at ~13.5 mL, while de-glycosylation of the doubly-disulfide bonded format eliminated the second minor peak at ~12.5 mL, resulting in a single, monodisperse product on SEC (FIGS. 7C & 10A-C).

To evaluate the potential impact of these changes on protein stability, the thermal stability of each version was monitored, as above (FIG. 7D). The melting point of the RA14 TCRds-huFc increased slightly with the addition of the second disulfide bond and slightly again after deglycosylation to 68.8° C. (Table 4). This melting temperature is in the range of values typically reported for antibody Fab domains (67-79° C.; Nguyen et al., 2015). It was subsequently confirmed that the SEC-purified glycosylated and genetically deglycosylated versions of each TCR2ds-Fc variant bind NLV tetramer similarly in an ELISA (FIGS. 8A-B).

Example 8—Engineered TCR Proteins Stain pMHC-Displaying Cells

To demonstrate the potential utility of high affinity TCR-Fc fusion proteins to detect CMV-positive cells, they were used to stain peptide-pulsed antigen presenting cells. To prevent background staining due to binding between the human Fc on the TCR2ds-huFc proteins and human Fc$\gamma$ receptors on the T2 cells, the human IgG1 hinge and Fc domains were replaced with their murine IgG2a counterparts to create TCR2ds-mFc constructs, which achieved similar yields and purity as the TCR2ds-huFc format (FIG. 9A). Human T2 antigen presenting cells were incubated overnight with 100 µM purified NLV or HCV peptide, stained with 1 µM purified TCR2ds-mFc followed by anti-mouse Fc-Alexa647 and analyzed by flow cytometry. Cells incubated with the HCV control peptide showed no shift in fluorescence as compared to cells incubated only with the anti-mouse Fc-AF647. A clear correlation in fluorescence shift with TCR affinity was observed, which increased from no detectable staining for RA14 to a distinct population for $\alpha$V2.$\beta$V8 (FIG. 9B). Finally, to determine the peptide detection sensitivity, the peptide dose was serially diluted before incubation with T2 cells and staining with 1 µM $\alpha$2$\beta$8 TCR2ds$\Delta$gly-mFc. Signals did not saturate at high peptide concentrations, as is expected for these TAP-deficient cells which upregulate MHC levels in the presence of peptide and were detectable down to 0.5 µM peptide (FIG. 9C).

Example 9—Further Improved RA14 TCR Variant, 341

Using nearly the same method described above, a variant with further increased affinity due to changes in CDR1 was identified. For this library, the alpha chain was appended with the PDGFR transmembrane anchor, which allowed us to select for enhanced alpha-beta chain pairing with an anti-beta chain antibody (FIG. 11). Additionally, the five predicted glycosylation sites were eliminated with amino acid substitutions at positions V$\alpha$:N20Q, C$\alpha$:N90Q, $\alpha$:N109Q, V$\beta$:N77Q and C$\beta$:N85.6Q, since these changes improved assembly of purified TCR-Fc protein and are expected to also enhance TCR assembly when expressed on the eukaryotic cell surface. To generate this library, four residues in CDR 1$\beta$ and 1$\alpha$ of the deglycosylated $\alpha$2.$\beta$8 were randomized using degenerate oligonucleotides (red residues in FIG. 11). Finally, instead of the KLV control peptide complexed with HLA A2, a similar peptide from influenza was used to monitor promiscuous peptide binding, here called GIL (full sequence: GILGFVFTL (SEQ ID NO: 51)), also complexed with HLA A2. Three rounds of FACS selection, performed as above, resulted in clone 341 with a single residue change at position V$\alpha$N29D and 7.8-fold enhanced binding over wild-type when displayed on CHO cells (Table 5 and FIG. 12). In the same experiment, $\alpha$2.$\beta$8 was 3-fold better than wild-type and clone 341-2.5-fold better than $\alpha$2.$\beta$8 (Table 5). Quantification of the flow data corresponding to FIG. 12 is shown below in Table 5 as well as in FIG. 13.

TABLE 5

Quantification of flow data from FIG. 12 to document improved binding to the NLN/A2 tetramer of TCR variants expressed on the CHO cell surface.
Ratio of NLN/A2 binding:TCR beta chain display (A647:PE)

|  | Stain with 10 nM NLN/A2 | Stain with 5 nM NLV/A2 | Stain with 10 nM GIL/A2 control |
|---|---|---|---|
| WT | 0.24 | 0.15 | 0.032 |
| $\alpha$2.$\beta$8 | 0.72 | 0.4 | 0.049 |
| 341 | 1.86 | 0.97 | 0.043 |
|  | Fold better than WT | | |
| $\alpha$2.$\beta$8 | 3.00 | 2.67 | |
| 341 | 7.75 | 6.47 | |
|  | Fold better than $\alpha$2.$\beta$8 | | |
| $\alpha$2.$\beta$8 | 1.00 | 1.00 | |
| 341 | 2.58 | 2.43 | |

None of the clones (wild-type RA14, $\alpha$2.$\beta$8, nor 341) binds to the control peptide when complexed with HLA-A2. Controlling for display level, there is an absolute improvement in binding.

Example 10: Further Development of Sub-Nanomolar TCR-Fc Variants

Additional affinity maturation of pp65/HLA-A2-specific TCRs was performed. Further mutations in CDR3$\alpha$, CDR3$\beta$, and CDR1$\alpha$ that have resulted in 300-fold improvements in affinity, down to ~10 nM Kd. These variants were used to create a final "shuffled" library comprising selected mutations or wild-type residue to remove detrimental or neutral mutations and identify beneficial or synergistic mutations. This library was generated using degenerate oligonucleotides and subjected to three additional rounds of FACS sorting after expression on the CHO cell surface and staining with fluorescent pMHC-tetramer-AF647. This resulted in identification of variants 2S-16, which has an affinity of 0.6 nM, as measured by SPR (see FIGS. 15-17). This represents a 1000-fold improved affinity as compared to the wild-type RA14 and improves the complex half-life from 2.3 seconds to 39 minutes. The affinity improved variants, especially the highest affinity 2S-16 variant, show an improved ability to detect pp65-pulsed human cells and exhibit decreased signal: noise (FIG. 18). When expressed on the surface of T cells with endogenous TCR transmembrane regions and exposed to human T2 cells pulsed with either the pp65 or a control peptide, the TCRs retain the ability to activate the T cell (FIG. 19).

Example 11: Antibody Fc Variants that Escape Capture by CMV Viral Fc Receptors (vFcR)

HCMV has evolved an impressive array of immune evasion strategies[7] that allow the virus to infect and establish latency at some point in the majority of humans. It is clear that HCMV infection stimulates a robust adaptive immune response, [8] but spread of clinical strains of HCMV is not inhibited by antibodies from seropositive individuals,[9] about 1% of seropositive mothers still transmit HCMV to their fetuses,[10] the best attempts at immunization are only ~50% effective,[11, 12] and prophylactic IVIG administration of HCMV-specific antibodies to pregnant women have not provided particularly impressive fetal protection.[13] For example, the neutralizing anti-HCMV monoclonal antibody MSL-109 prevented hCMV infection in vitro, but not in the clinic. This antibody binds the glycoprotein gH on the surface of infected cells, but HCMV quickly became resistant to the antibody.[14]

The ability of antibodies to eliminate hCMV-infected cells and prevent cell-to-cell spread [9] appears to be hampered by expression of viral Fc gamma receptors (vFcγRs). HCMV induces the expression of vFcγRs in infected cells, which causes capture and degradation of antibodies targeting HCMV.[15] In theory, antibody-cellular cytotoxicity (ADCC) and antibody-dependent cellular phagocytosis (ADCP) should be important components of an immune response to viral infection, but data supporting this role is limited. Data suggest that previously tested antibody therapeutics such as the anti-gH MSL-109 have been negatively impacted by the immune evasion mediated by vFcγRs.[14] When vFcγRs are expressed on the infected cell's surface, antibodies that bind exposed antigens, such as a pMHC complex or gH, are then bound by vFcγRs and internalized via bipolar bridging[15, 16] for degradation or repackaging for further evasion.[14] In HCMV strains lacking the vFcγRs gp34 and gp68, HCMV antibodies were much more potently able to bind human FcγRs and induce ADCC in vitro.[17] This immune response blunts the ability of antibodies to initiate ADCC and stimulate local immune responses.

Human Fc receptors in the FcγRI, FcγRII, and FcγRIII families all have overlapping binding sites on the human IgG1 Fc hinge, while FcRn binds between CH2 and CH3. To determine whether the binding sites of the human and viral Fc receptors can be uncoupled, gp34 and gp68 proteins were first cloned and purified. The gp34 protein (residues 24-182) and a truncated version of gp68 (tgp68; residues 68-289) were expressed, purified, and characterized (FIG. 20). The genes encoding the vFcγRs were amplified from the AD169/GFP[18] BAC (with an added strep tag for purification and detection and expressed in CHO cells. After purification, both proteins are homogeneous and monodisperse. Gp34 expresses as a homodimer of ~30 kDa glycosylated monomers, while gp68 expresses as a monomer of ~68 kDa.

The human and viral Fc receptors were used in competition ELISAs to determine that gp34 competitively inhibits FcgRIIIa binding while tgp68 competitively inhibits FcRn binding (FIG. 21). These data show that gp34 likely shares a partially overlapping epitope with FecγRIIIA, while gp68 likely binds near the FcRn binding site, and the two vFcγRs do not share an epitope. Prior mutagenesis studies support the conclusions that gp68 binds in the CH2-CH3 hinge.[19]

Figure 22:
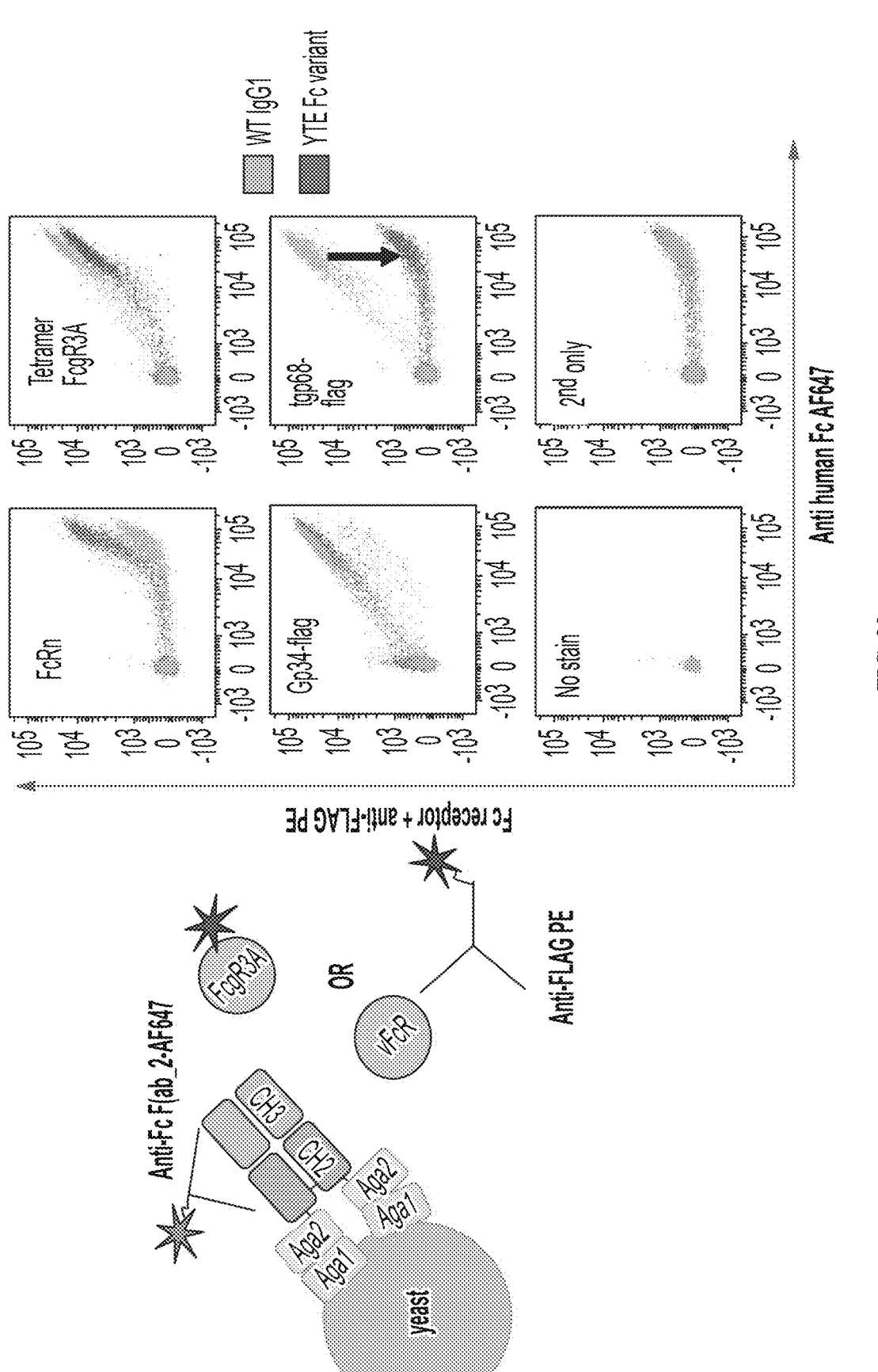

Additional ELISAs evaluated binding of the Fc receptors to multiple established Fc variants. The vFcγRs were minimally impacted by mutations known to impact FcRn and FecγRIIIA binding, with the exception of YTE,[20] which improves binding to FcRn, but abolishes binding to tgp68 (FIG. 22). This indicates that the vFcγRs do not bind identical epitopes to either FcRn or FcγRIIIA.

Using yeast Fc display, additional antibody Fc variants were identified that have lost the ability to bind two vFecγRs but retain native binding to the host Fcγ receptors, including FcgRIIIA which is required for ADCC and FcRn which mediates antibody recycling and is crucial for the long antibody half-life in serum. The human IgG1 Fc region was mutagenized and screened by yeast display to identify variants with reduced binding to HCMV vFecγRs but retain binding to host FcRn and FcgRIIIa. Libraries were created by error prone PCR on the CH2 domain with a 0.25% error rate to yield a final library of $1.6 \times 10^6$ variants. The hinge region was excluded from mutagenesis as it includes the FegR3A binding site. The library was initially sorted by flow cytometry to select variants that maintain binding to FcγRIIIA. After regrowth, they were then sorted for variants which lost gp34 binding by staining with 20 nM FcγRIIIa-PE in the presence of an excess (1.5 μM) of unlabeled, purified gp34 as competitor. Selected sequences are shown in FIG. 23 and binding to viral and host Fc receptors in FIG. 24.

Example 12: Expression of Additional TCR Constructs in CHO Cells

To demonstrate the generality of this CHO cell system for expression and engineering of TCRs, other than the RA14 TCR, additional TCR constructs were studied.

Figure 14:
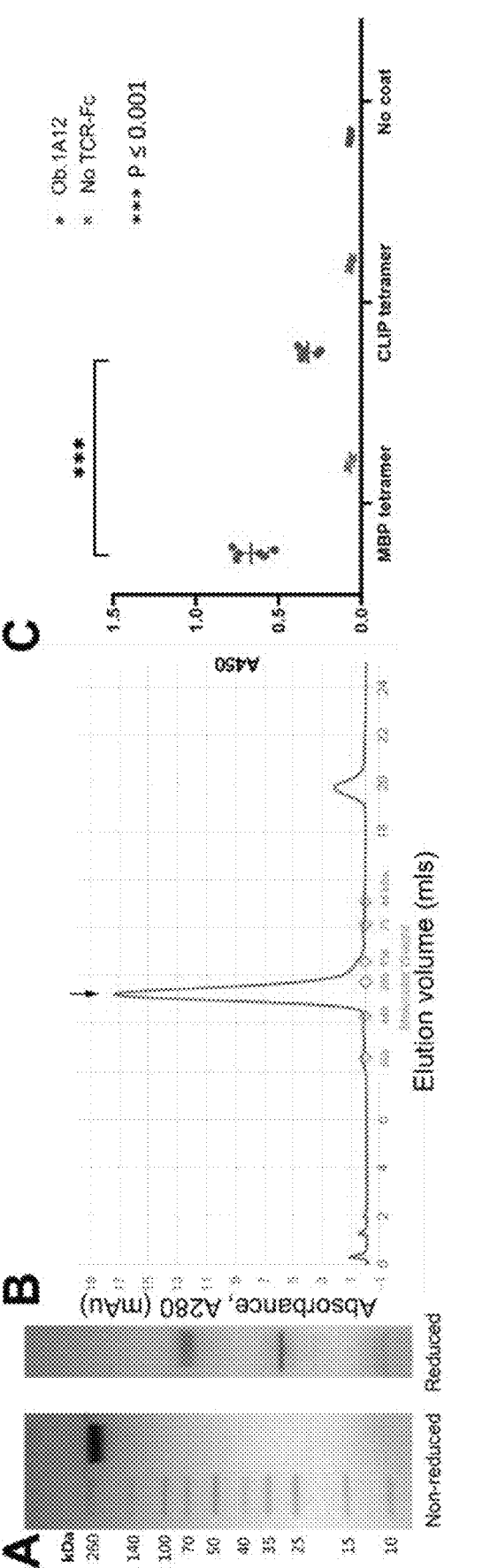

The Ob.1A12 human TCR recognizing the myelin basic protein peptide formed by residues 85-99 when presented by the class II DRB1*1501 MHC molecule was derived from a patient with relapsing-remitting multiple sclerosis (Wucherpfennig et al., 1994). Notably, as an autoimmune-associated TCR, this exhibits a very low affinity (estimated at Kd>100 μM) for its pMHC ligand. This TCR was expressed in CHO cells as a TCR-Fc fusion protein with the alpha chain fused to the human Fc domain and purified using protein A chromatography. Protein gel shows the protein purity, while size exclusion chromatography shows that the protein is monodisperse (FIG. 14).

Two classic mouse TCRs were also used as model systems. The OT-II and the DO11.10 mouse TCRs both bind the same ovalbumin peptide (residues 323-339) when bound by the class II MHC I-Ab (OT-II) or I-Ad (DO11.10). These T cell hybridomas, originally elicited by vaccination of mice with hen egg white ovalbumin (OVA) (White et al., 1983), are well understood model system used to study CD4+ T cell responses (Scott et al., 1998). Class II MHCs present exogenous peptides and are thus important for infection resistance and autoimmunity. Data presented in FIGS. 26-28 demonstrate that these TCR-Fc fusion constructs produced in CHO cells could likewise be successfully, expressed and purified and displayed the selective binding to target peptide.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aggen et al., (2011) Identification and engineering of human variable regions that allow expression of stable single-chain T cell receptors. *Protein Eng Des Sel* 24, 361-372.

Anikeeva et al., (2009) Can oligomeric T-cell receptor be used as a tool to detect viral peptide epitopes on infected cells? *Clin Immunol* 130, 98-109.

Bossi et al., (2013) Examining the presentation of tumor-associated antigens on peptide-pulsed T2 cells. *Oncoimmunology* 2, e26840.

Bossi et al., (2014) ImmTAC-redirected tumour cell killing induces and potentiates antigen cross-presentation by dendritic cells. *Cancer Immunol Immunother* 63, 437-448.

Boulter et al., (2003) Stable, soluble T-cell receptor molecules for crystallization and therapeutics. *Protein Eng* 16, 707-711.

Chervin et al., (2008) Engineering higher affinity T cell receptors using a T cell display system. *J Immunol Methods* 339, 175-184.

Chng et al., (2015) Cleavage efficient 2A peptides for high level monoclonal antibody expression in CHO cells. *MAbs* 7, 403-412.

Cohen et al., (2006) Enhanced antitumor activity of murine-human hybrid T-cell receptor (TCR) in human lymphocytes is associated with improved pairing and TCR/CD3 stability. *Cancer Res* 66, 8878-8886.

Colby et al., (2004) Engineering antibody affinity by yeast surface display. *Methods Enzymol* 388, 348-358.

Cole et al., (2013) Increased Peptide Contacts Govern High Affinity Binding of a Modified TCR Whilst Maintaining a Native pMHC Docking Mode. *Front Immunol* 4, 168.

Feuchtinger et al., (2010) Adoptive transfer of pp65-specific T cells for the treatment of chemorefractory cytomegalovirus disease or reactivation after haploidentical and matched unrelated stem cell transplantation. *Blood* 116, 4360-4367.

Foss et al., (2016) Enhanced FcRn-dependent transepithelial delivery of IgG by Fc-engineering and polymerization. *J Control Release* 223, 42-52.

Gakamsky et al., (2007) Kinetic evidence for a ligand-binding-induced conformational transition in the T cell receptor. *Proc Natl Acad Sci USA* 104, 16639-16644.

Goyarts et al., (1998) Point mutations in the beta chain CDR3 can alter the T cell receptor recognition pattern on an MHC class I/peptide complex over a broad interface area. *Mol Immunol* 35, 593-607.

Gras et al., (2009) Structural bases for the affinity-driven selection of a public TCR against a dominant human cytomegalovirus epitope. *J Immunol* 183, 430-437.

Gregoire et al., (1991) Engineered secreted T-cell receptor alpha beta heterodimers. *Proc Natl Acad Sci USA* 88, 8077-8081.

Gunnarsen et al., (2013) Chaperone-assisted thermostability engineering of a soluble T cell receptor using phage display. *Scientific reports* 3, 1162.

Harris & Kranz, (2016) Adoptive T Cell Therapies: A Comparison of T Cell Receptors and Chimeric Antigen Receptors. *Trends Pharmacol Sci* 37, 220-230.

Ho et al., (1998) Rapid cytomegalovirus pp65 antigenemia assay by direct erythrocyte lysis and immunofluorescence staining. *J Clin Microbiol* 36, 638-640.

Holler et al., (2000) In vitro evolution of a T cell receptor with high affinity for peptide/MHC. *Proc Natl Acad Sci USA* 97, 5387-5392.

Holler et al., (2003) TCRs with high affinity for foreign pMHC show self-reactivity. *Nat Immunol* 4, 55-62.

Irving et al., (2012) Interplay between T cell receptor binding kinetics and the level of cognate peptide presented by major histocompatibility complexes governs CD8+ T cell responsiveness. *J Biol Chem* 287, 23068-23078.

Kageyama et al., (1995) Variations in the number of peptide-MHC class I complexes required to activate cytotoxic T cell responses. *J Immunol* 154, 567-576.

Kessels et al., (2000) Changing T cell specificity by retro-viral T cell receptor display. *Proc Natl Acad Sci USA* 97, 14578-14583.

Kuball et al., (2009) Increasing functional avidity of TCR-redirected T cells by removing defined N-glycosylation sites in the TCR constant domain. *J Exp Med* 206, 463-475.

Lebowitz et al., (1999) Soluble, high-affinity dimers of T-cell receptors and class II major histocompatibility complexes: biochemical probes for analysis and modulation of immune responses. *Cell Immunol* 192, 175-184.

Li et al., (2005) Directed evolution of human T-cell receptors with picomolar affinities by phage display. *Nat Biotechnol* 23, 349-354.

Liddy et al., (2012) Monoclonal TCR-redirected tumor cell killing. *Nat Med* 18, 980-987.

Lunde et al., (2010) Stabilizing mutations increase secretion of functional soluble TCR-Ig fusion proteins. *BMC Biotechnol* 10, 61.

Makler et al., (2010) Direct visualization of the dynamics of antigen presentation in human cells infected with cytomegalovirus revealed by antibodies mimicking TCR specificity. *Eur J Immunol* 40, 1552-1565.

Malecek et al., (2013) Engineering improved T cell receptors using an alanine-scan guided T cell display selection system. *J Immunol Methods* 392, 1-11.

Maynard et al., (2005) High-level bacterial secretion of single-chain αβ T-cell receptors. *Journal of Immunological Methods* 306, 51-67.

Mosquera et al., (2005) In vitro and in vivo characterization of a novel antibody-like single-chain TCR human IgG1 fusion protein. *J Immunol* 174, 4381-4388.

Nguyen et al., (2015) A cocktail of humanized anti-pertussis toxin antibodies limits disease in murine and baboon models of whooping cough. *Sci Transl Med* 7, 316ra195.

Nguyen et al., (2018) Identification of high affinity HER2 binding antibodies using CHO Fab surface display. *Protein Eng Des Sel* 31, 91-101.

Oates et al., (2015) ImmTACs for targeted cancer therapy: Why, what, how, and which. *Mol Immunol* 67, 67-74.

Ozawa et al., (2012) The binding affinity of a soluble TCR-Fc fusion protein is significantly improved by cross-linkage with an anti-Cbeta antibody. *Biochem Biophys Res Commun* 422, 245-249.

Plotkin & Boppana, (2018) Vaccination against the human cytomegalovirus. *Vaccine, published online Apr.* 2, 2018.

Riddell et al., (1991) Class I MHC-restricted cytotoxic T lymphocyte recognition of cells infected with human cytomegalovirus does not require endogenous viral gene expression. *J Immunol* 146, 2795-2804.

Rossjohn et al., (2015) T cell antigen receptor recognition of antigen-presenting molecules. *Annu Rev Immunol* 33, 169-200.

Sami et al., (2007) Crystal structures of high affinity human T-cell receptors bound to peptide major histocompatibility complex reveal native diagonal binding geometry. *Protein Eng Des Sel* 20, 397-403.

Saulquin et al., (2000) A global appraisal of immunodominant CD8 T cell responses to Epstein-Barr virus and cytomegalovirus by bulk screening. *Eur J Immunol* 30, 2531-2539.

Scott, et al., Crystal structures of two I-Ad-peptide complexes reveal that high affinity can be achieved without large anchor residues. *Immunity,* 1998. 8(3): p. 319-29

Shusta et al., (1999) Yeast polypeptide fusion surface display levels predict thermal stability and soluble secretion efficiency. *J Mol Biol* 292, 949-956.

Shusta et al., (2000) Directed evolution of a stable scaffold for T-cell receptor engineering. *Nat Biotechnol* 18, 754-759.

Sibener et al., (2018) Isolation of a Structural Mechanism for Uncoupling T Cell Receptor Signaling from Peptide-MHC Binding. *Cell* 174, 672-687 e627.

Smith et al., (2009) Rapid generation of fully human monoclonal antibodies specific to a vaccinating antigen. *Nat Protoc* 4, 372-384.

Sykulev et al., (1996) Evidence that a single peptide-MHC complex on a target cell can elicit a cytolytic T cell response. *Immunity* 4, 565-571.

Trautmann et al., (2005) Selection of T cell clones expressing high-affinity public TCRs within Human cytomegalovirus-specific CD8 T cell responses. *J Immunol* 175, 6123-6132.

van Boxel et al., (2009) Some lessons from the systematic production and structural analysis of soluble (alpha)(beta) T-cell receptors. *J Immunol Methods* 350, 14-21.

Varela-Rohena et al., (2008) Control of HIV-1 immune escape by CD8 T cells expressing enhanced T-cell receptor. *Nat Med* 14, 1390-1395.

Walseng et al., (2015) Soluble T-cell receptors produced in human cells for targeted delivery. *PLoS One* 10, e0119559.

Wang et al., (2012) T cell receptor alphabeta diversity inversely correlates with pathogen-specific antibody levels in human cytomegalovirus infection. *Sci Transl Med* 4, 128ra142.

Wang et al., (2015) CMVpp65 Vaccine Enhances the Antitumor Efficacy of Adoptively Transferred CD19-Redirected CMV-Specific T Cells. *Clin Cancer Res* 21, 2993-3002.

White et al., Use of I region-restricted, antigen-specific T cell hybridomas to produce idiotypically specific anti-receptor antibodies. *J Immunol,* 1983. 130(3): p. 1033-7.

Wills et al., (1996) The human cytotoxic T-lymphocyte (CTL) response to cytomegalovirus is dominated by structural protein pp65: frequency, specificity, and T-cell receptor usage of pp65- specific CTL. *J Virol* 70, 7569-7579.

Wucherpfennig et al., Clonal expansion and persistence of human T cells specific for an immunodominant myelin basic protein peptide. *J Immunol,* 1994. 152(11): p. 5581-92.

Wulfing & Pluckthun, (1994) Correctly folded T-cell receptor fragments in the periplasm of *Escherichia coli*. Influence of folding catalysts. *J Mol Biol* 242, 655-669.

Yang et al., (2015) Structural Basis for Clonal Diversity of the Public T Cell Response to a Dominant Human Cytomegalovirus Epitope. *J Biol Chem* 290, 29106-29119.

Yang et al., (2016) Elimination of Latently HIV-infected Cells from Antiretroviral Therapy-suppressed Subjects by Engineered Immune-mobilizing T-cell Receptors. *Mol Ther* 24, 1913-1925.

---

What is claimed is:

1. An engineered T-cell receptor (TCR) comprising an alpha chain comprising the CDR1, CDR2, and CDR3 from one of SEQ ID NOs: 19-26 and 74-76 and a beta chain comprising the CDR1, CDR2, and CDR3 from one of SEQ ID NOs: 28-38 and 67-68.

2. The engineered TCR of claim 1, wherein the engineered TCR is HLA-A2 restricted.

3. The engineered TCR of claim 1, wherein the engineered TCR is HLA-A2*02:01 restricted.

4. The engineered TCR of claim 1, wherein the engineered TCR specifically recognizes a peptide comprising the amino acid sequence of NLVPMVATV (SEQ ID NO: 41) in complex with HLA-A2*02:01.

5. The engineered TCR of claim 1, wherein the engineered TCR comprises an alpha chain CDR3 having the amino acid sequence of SEQ ID NO: 2 and a beta chain CDR3 having the amino acid sequence of SEQ ID NO: 15.

6. The engineered TCR of claim 1, wherein the engineered TCR comprises an alpha chain variable domain having at least 90% identity to the amino acid sequence of any one of SEQ ID NOs: 19-26 and 74-76 and a beta chain variable domain having at least 90% identity to the amino acid sequence of any one of SEQ ID NOs: 28-38 and 67-68.

7. The engineered TCR of claim 1, wherein the engineered TCR comprises an alpha chain variable domain of any one of SEQ ID NOs: 19-26 and 74-76 and a beta chain variable domain of any one of SEQ ID NOs: 28-38 and 67-68.

8. The engineered TCR of claim 1, wherein the engineered TCR comprises an alpha chain variable domain of SEQ ID NO: 19 and a beta chain variable domain of SEQ ID NO: 32.

9. The engineered TCR of claim 1, wherein the engineered TCR is further defined as a soluble TCR, wherein the soluble TCR does not comprise a transmembrane domain.

10. The engineered TCR of claim 9, wherein the soluble TCR is linked to a CD3-specific antibody.

11. The engineered TCR of claim 9, wherein an extracellular domain of the TCR is fused to an antibody Fc domain.

12. The engineered TCR of claim 11, wherein the alpha chain of the TCR extracellular domain is fused to the antibody Fc domain.

13. The engineered TCR of claim 11, wherein the Fc domain is a human or mouse Fc domain.

14. The engineered TCR of claim 11, further comprising an antibody hinge region.

15. A polynucleotide encoding the engineered TCR of claim 1.

16. An expression vector comprising a polynucleotide encoding the engineered TCR of claim 1.

17. The expression vector of claim 16, wherein the polynucleotide further encodes a linker domain positioned between the alpha chain and the beta chain.

18. The expression vector of claim 17, wherein the linker domain comprises one or more cleavage sites.

19. The expression vector of claim 18, wherein the one or more cleavage sites are a Furin cleavage site, T2A cleavage site and/or a P2A cleavage site.

20. A cell comprising the expression vector of claim 16.

* * * * *